(12) United States Patent
Tani et al.

(10) Patent No.: US 9,564,274 B2
(45) Date of Patent: *Feb. 7, 2017

(54) METAL COMPLEX DYE, PHOTOELECTRIC CONVERSION ELEMENT, DYE-SENSITIZED SOLAR CELL, DYE SOLUTION, AND COMPOUND

(71) Applicant: FUJIFILM Corporation, Minato-Ku, Tokyo (JP)

(72) Inventors: Yukio Tani, Kanagawa (JP); Katsumi Kobayashi, Kanagawa (JP); Kimiatsu Nomura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 29 days.

This patent is subject to a terminal disclaimer.

(21) Appl. No.: 14/301,796

(22) Filed: Jun. 11, 2014

(65) Prior Publication Data

US 2014/0290746 A1    Oct. 2, 2014

Related U.S. Application Data

(63) Continuation of application No. PCT/JP2012/079563, filed on Nov. 14, 2012.

(30) Foreign Application Priority Data

| Dec. 15, 2011 | (JP) | 2011-275129 |
| Mar. 29, 2012 | (JP) | 2012-078148 |
| Oct. 19, 2012 | (JP) | 2012-232400 |

(51) Int. Cl.
*H01G 9/20* (2006.01)
*C07D 213/79* (2006.01)
(Continued)

(52) U.S. Cl.
CPC .......... *H01G 9/2059* (2013.01); *C07D 213/79* (2013.01); *C07D 401/04* (2013.01);
(Continued)

(58) Field of Classification Search
CPC ................ H01G 9/20–9/2095; C07F 15/0026; C07F 15/0053; C09B 23/105; C09B 57/10; H01L 51/0086
See application file for complete search history.

(56) References Cited

U.S. PATENT DOCUMENTS

| 2010/0258175 A1 | 10/2010 | Chi et al. |
| 2011/0076539 A1* | 3/2011 | Kobayashi .......... H01L 51/0061 429/111 |

(Continued)

FOREIGN PATENT DOCUMENTS

| JP | 2001-006760 A | 1/2001 |
| JP | 2001-291534 A | 10/2001 |

(Continued)

OTHER PUBLICATIONS

Bo-So Chen et al., "Neutral, panchromatic Ru(II) terpyridine sensitizers bearing pyridine pyrazolate chelates with superior DSSC performance", Chem Commun., 2009, pp. 5844-5846.

(Continued)

*Primary Examiner* — William E McClain
(74) *Attorney, Agent, or Firm* — Sughrue Mion, PLLC

(57) ABSTRACT

A photoelectric conversion element, having: an electrically-conductive support; a photoconductor layer having a semiconductor fine-particle layer adsorbed a dye; a charge transfer layer containing an electrolyte; and a counter electrode; which are provided on one side of the support in this order, in which the dye has at least one terdentate ligand having at least one acidic group; at least one ligand coordinating to a metal atom M has an sp2 carbon atom; a cyclic group binds (Continued)

to the sp2 carbon atom; a specific substituent R is substituted at an atom of α- or β-position to the atom of the cyclic group directly binding to the sp2 carbon atom; and with the metal atom M, an atom G1 of the α- or β-position, and an atom G2 of the substituent R, an angle θ (∠MG1G2) is 150° or less.

11 Claims, 4 Drawing Sheets

(51) Int. Cl.
*C07D 401/04* (2006.01)
*C07D 409/14* (2006.01)
*C09B 57/10* (2006.01)

(52) U.S. Cl.
CPC ............ *C07D 409/14* (2013.01); *C09B 57/10* (2013.01); *Y02E 10/542* (2013.01)

(56) References Cited

U.S. PATENT DOCUMENTS

| | | | |
|---|---|---|---|
| 2011/0277841 | A1 | 11/2011 | Chi et al. |
| 2012/0073660 | A1 | 3/2012 | Chi et al. |
| 2012/0247561 | A1 | 10/2012 | Chi et al. |
| 2012/0253043 | A1* | 10/2012 | Nazeeruddin ....... H01L 51/0086 546/2 |
| 2013/0160855 | A1* | 6/2013 | Gibson ............... H01L 51/0083 136/263 |
| 2014/0209172 | A1* | 7/2014 | Tani ........................ C09B 57/10 136/263 |
| 2015/0248969 | A1* | 9/2015 | Watanabe ........... C07F 15/0046 136/256 |
| 2016/0012977 | A1* | 1/2016 | Tani ...................... C09B 23/005 136/263 |
| 2016/0042875 | A1* | 2/2016 | Watanabe ............ H01G 9/2059 136/263 |

FOREIGN PATENT DOCUMENTS

| | | | | |
|---|---|---|---|---|
| JP | 2002-025636 | A | 1/2002 | |
| JP | EP 1231619 | A2 * | 8/2002 | ......... H01L 51/0086 |
| JP | 2007-277166 | A | 10/2007 | |
| JP | 2012-084250 | A | 4/2012 | |
| SE | WO 2012001033 | A1 * | 1/2012 | ......... H01L 51/0083 |
| WO | 2011/152318 | A1 | 12/2011 | |

OTHER PUBLICATIONS

International Search Report for PCT/JP2012/079563 dated Feb. 19, 2013.

Communication dated Jun. 26, 2015, issued by the European Patent Office in counterpart Application No. 12857608.9.

Chou et al., Ruthenium(II) Sensitizers with Heteroleptic Tridentate Chelates for Dye-Sensitized Solar Cells, Angewandte Chemie International Edition, 2011, vol. 50, Issue 9, p. 2054-2058.

* cited by examiner

METAL COMPLEX DYE, PHOTOELECTRIC CONVERSION ELEMENT, DYE-SENSITIZED SOLAR CELL, DYE SOLUTION, AND COMPOUND

CROSS-REFERENCE TO RELATED APPLICATIONS

This application is a Continuation of PCT International Application No. PCT/JP2012/079563 filed on Nov. 14, 2012, which claims priority under 35 U.S.C. §119(a) to Japanese Patent Application No. 2011-275129 filed on Dec. 15, 2011, Japanese Patent Application No. 2012-078148 filed on Mar. 29, 2012, and Japanese Patent Application No. 2012-232400 filed on Oct. 19, 2012. Each of the above applications is hereby expressly incorporated by reference, in its entirely, into the present application.

TECHNICAL FIELD

The present invention relates to a metal complex dye, a photoelectric conversion element, a dye-sensitized solar cell, a dye solution, and a compound.

BACKGROUND ART

Photoelectric conversion elements are used in various photosensors, copying machines, solar cells, and the like. These photoelectric conversion elements have adopted various systems to be put into use, such as elements utilizing metals, elements utilizing semiconductors, elements utilizing organic pigments or dyes, or combinations of these elements. In particular, solar cells that make use of non-exhaustive solar energy do not necessitate fuels, and full-fledged practicalization of solar cells as an inexhaustible clean energy is being highly expected. Among these, research and development of silicon-based solar cells have long been in progress. Many countries also support policy-wise considerations, and thus dissemination of silicon-based solar cells is still in progress. However, silicon is an inorganic material, and has limitations per se in terms of throughput and molecular modification.

Under such circumstances, research is being vigorously carried out on dye-sensitized solar cells. Especially, to have built momentum toward such research is research results by Graetzel et al. of École Polytechnique Fédérale de Lausanne in Switzerland. They employed a structure in which a dye formed from a ruthenium complex was fixed at the surface of a porous titanium oxide thin film, and realized a conversion efficiency that was comparable to that of amorphous silicon. Thus, the dye-sensitized solar cells instantly attracted the attention of researchers all over the world.

Hetherto, as metal complex dyes to be used in photoelectric conversion elements, N3, N719, Z907, and J2 have been developed. However, it was often the case that conventional dye-sensitized solar cells generally were low in photoelectric conversion efficiency and poor in durability.

Recently, as a metal complex dye which is excellent in terms of absorption coefficient in the wavelength range of 450 to 550 nm, photoelectric conversion efficiency, and stability, ruthenium metal complex dyes having terpyridyl and 3-trifluoromethyl-5-[4-(p-substituted phenylethenyl)-2-pyridyl]pyrazole, as ligands, were developed (see Non-Patent Literature 1). More recently in particular, solar sells get attention to and raise expectation for energy sources in place of nuclear power generation, and more improvement in performance of the solar sell has been required.

CITATION LIST

Non-Patent Literature

Non-Patent Literature 1: Chemical Communications, 2009, pp. 5844-5846

SUMMARY OF THE INVENTION

Technical Problem

The revel of performance required for dye-sensitized solar sells is going on increasing year by year. As a result, conventional techniques including metal complex dyes disclosed in the Non-Patent Literature 1 are not always satisfactory. In particular, it has been found that ruthenium metal complex dyes developed in the Non-Patent Literature 1 improve durability thereof as compared with conventional ones, but that they are likely to cause association between two molecules of the dye and adsorption of the dye on two or more layers, and tend to cause variation in performance, as described below. As a result, it has been understood that it is necessary to improve such variation in performance and to achieve further improvement in performance without lowering other performances, such as photoelectric conversion efficiency and durability. Further, dyes which hardly associate are required, from the viewpoint that short-circuit current density (Jsc) is lowered because electron injection into semiconductor fine-particles is inhibited, by association between two molecules of the dye or multilayer adsorption of the dye.

Thus, the present invention is contemplated for providing: metal complex dyes balancing reduction of variation in performance, with improvement in both of photoelectric conversion efficiency ($\eta$) and durability, thereby showing excellent performance; photoelectric conversion elements and dye-sensitized solar sells utilizing the metal complex dye, thereby showing excellent performance; dye solutions containing the metal complex dye; and compounds which are useful as a ligand of the metal complex dye.

Solution to Problem

In order to improve photoelectric conversion efficiency ($\eta$), it is necessary to improve both of short-circuit current density (Jsc) and open-circuit voltage (Voc). However, in the conventional ruthenium metal complex dye, because a covering of the dye on the semiconductor fine-particle surface is unsatisfactory, the resultant open-circuit voltage (Voc) is lost, due to reverse electron transfer of electrons having been injected to the semiconductor fine-particles into a redox system (for example, $I_3^-$) in the electrolyte. The present inventors have therefore thought that in order to minimize a portion of the semiconductor fine-particle surface which has not been covered with a dye yet, it is effective to give the dye a substituent which extends in a direction parallel to the semiconductor fine-particle surface, when the dye adsorbs thereon. For example, we supposed that if a dye molecule having a parasol-like structure adsorbs on semiconductor fine-particles at a handle portion of the parasol, all over the semiconductor fine-particle surface can be covered with the parasol, and access of the redox system (for example, $I_3^-$) in the electrolyte to the semiconductor fine-particle surface can be kept to minimum, and as a result, reverse electron transfer can be minimized.

As a result of studies based on this supposition, in addition to the above-described effects, variation in performance has been reduced by the use of a metal complex dye of the present invention. The cause is assumed because association between dye molecules and adsorption of the dye extended into two or more layers are suppressed by a specific parasol-type molecular structure, and as a result, the dye has become easy to adsorb homogeneously, which is different from, for example, the ruthenium metal complex dye developed by the Non-Patent Literature 1.

Further, by giving a specific structure to the dye, the resultant dye has excellent properties, each of adsorptive power, short-circuit current density (Jsc), solution stability or adsorption rate. As for the short-circuit current density (Jsc), it is assumed that suppression of association is accelerated by introduction of a substituent, and as a result, electron injection has been efficiently caused.

That is, the tasks of the present invention can be achieved by the following means.

(1) A photoelectric conversion element, having:
an electrically-conductive support;
a photoconductor layer having a layer of semiconductor fine-particles that have adsorbed a dye;
a charge transfer layer containing an electrolyte; and
a counter electrode;
which are provided on one side of the electrically-conductive support in this order,
wherein the dye has at least one terdentate ligand having at least one acidic group; at least one ligand coordinating to a metal atom M has an sp2 carbon atom; a cyclic group binds to the sp2 carbon atom; in a circle position connecting through a carbon atom(s) from an atom of the cyclic group directly binding to the sp2 carbon atom, a substituent R is substituted at an atom of an α-position or β-position to the atom of the cyclic group directly binding to the sp2 carbon atom, with the substituent R being selected from a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, or a silyloxy group; and when the atom of the α-position or β-position to which the substituent R binds is defined as G1 and an atom of the substituent R which directly binds to the atom G1 is defined as G2, an angle θ (∠MG1G2) formed by the metal atom M, the atom G1 and the atom G2, which is centered on the atom G1, is 150° or less.

(2) The photoelectric conversion element described in item (1), wherein the sp2 carbon atom is a ring-constituting carbon atom, or a carbon atom in an ethylene structure conjugated to an aromatic ring.

(3) The photoelectric conversion element described in item (1) or (2), wherein a maximum linking chain number $N_R$ of linking chain numbers (bond numbers) of a linking chain linking the atom G1 with an atom located at the furthest position through a linkage of the substituent R is more than ½ times of a minimum linking chain number $N_{M-G1}$ of linking chain numbers (bond numbers) of a linking chain linking from the metal atom M to the atom G1.

(4) The photoelectric conversion element described in item (3), wherein the maximum linking chain number $N_R$ is more than 1 time of the minimum linking chain number $N_{M-G1}$.

(5) The photoelectric conversion element described in any one of items (1) to (4), wherein the angle θ is an acute angle, and wherein the substituent R is bonded at the α-position of the cyclic group.

(6) The photoelectric conversion element described in any one of items (1) to (5), wherein the metal complex dye is represented by formula (I):

M(LD)m1(LA)m2(X)m3.CI     Formula (I)

wherein, in formula (I), M represents Ru or Os; LD represents a bidentate or terdentate ligand represented by formula (A); LA represents a terdentate ligand represented by formula (B); X represents a monodentate ligand; CI represents a counter ion in the case where the counter ion is necessary to neutralize a charge in formula (I); m1 represents 1 or 2; m2 represents 1; and m3 represents 0 or 1;

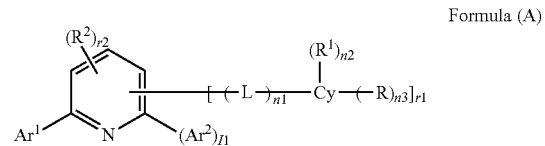

Formula (A)

wherein, in formula (A), Cy represents a cyclic group; R represents a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, or a silyloxy group; $R^1$ represents a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, a silyloxy group, an aryl group, or a heteroaryl group; $R^2$ represents a substituent;
$Ar^1$ and $Ar^2$ each independently represent a carbocyclic aromatic group having an anion, a nitrogen-containing aromatic group having a lone electron pair, or a nitrogen-containing aromatic group having an anion;
L represents an ethenylene group, an ethynylene group, an arylene group, or a heteroarylene group;
n1 represents an integer of 0 to 3; n2 represents an integer of 0 to 4; n3 represents 1 or 2; r1 represents an integer of 1 to 3; r2 represents an integer of 0 to 2; and l1 represents 0 or 1;

Formula (B)

wherein, in formula (B), Za, Zb and Zc each independently represent a group of atoms for forming a 5- or 6-membered ring, in which at least one of the rings formed by Za, Zb and Zc has an acidic group;
$Q^1$ to $Q^3$ each independently represent a nitrogen atom having a lone electron pair, a nitrogen atom having an anion, or a carbon atom having an anion; and
$D^1$ to $D^4$ each independently represent a carbon atom or a nitrogen atom.

(7) The photoelectric conversion element described in item (6), wherein Cy in formula (A) is represented by formula (A-1) or (A-2):

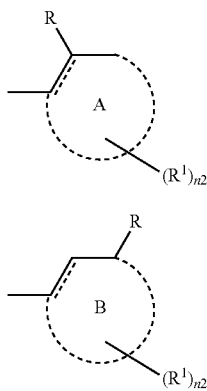

Formula (A-1)

Formula (A-2)

wherein, in formulas (A-1) and (A-2), R and $R^1$ have the same meaning as those in formula (A), respectively; a ring A and a ring B each represent a 5- or 6-membered cyclic group; in which R and $R^1$ do not bind together to form a ring; when there are a plurality of $R^1$'s, these may be bonded to each other to form a condensed ring structure; and a broken line described between the atom of a bonding hand in the above-described group and the binding position of R means that this portion may be a single bond or a double bond.

(8) The photoelectric conversion element described in item (6) or (7), wherein Cy in formula (A) is represented by formula (A-1).

(9) The photoelectric conversion element described in any one of items (6) to (8), wherein LD in formula (I) is represented by formula (A-3):

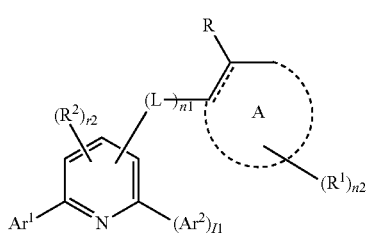

Formula (A-3)

wherein, in formula (A-3), $Ar^1$, $Ar^2$, R, $R^1$, $R^2$, L, l1, n1, n2, r2, and the ring A have the same meaning as those in formulas (A) and (A-1), respectively.

(10) The photoelectric conversion element described in any one of items (6) to (9), wherein the ligand represented by formula (B) is represented by any one of formulas (B1) to (B8):

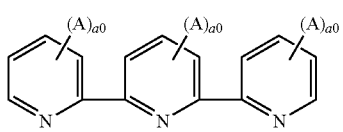

Formula (B1)

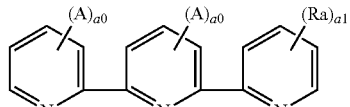

Formula (B2)

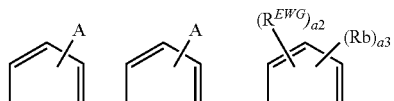

Formula (B3)

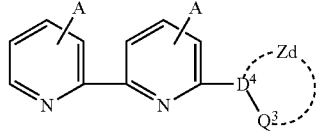

Formula (B4)

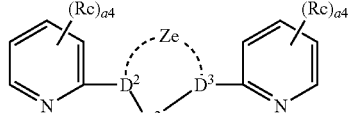

Formula (B5)

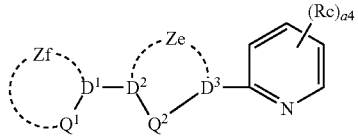

Formula (B6)

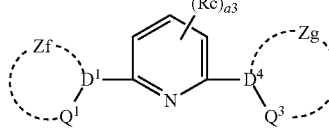

Formula (B7)

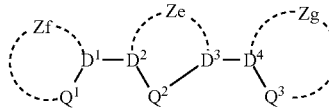

Formula (B8)

wherein, in formulas (B1) to (B8), $Q^1$ to $Q^3$ and $D^1$ to $D^4$ have the same meaning as those in formula (B), respectively; Zd represent a group of atom for forming a benzene ring, a naphthalene ring, an anthracene ring, a phenanthrene ring, a pyrene ring, a perylene ring, a pyrrole ring, an indole ring, an imidazole ring, a benzoimidazole ring, a pyrazole ring, a pyrazine ring, a pyrimidine ring, a benzopyrimidine ring, a pyridazine ring, a benzopyridazine ring, a triazole ring, a benzotriazole ring, a tetrazole ring, an indazole ring, a triazine ring, a purine ring, a quinoline ring, an isoquinoline ring, a quinazoline ring, a thiazole ring, a benzothiazole ring, an isothiazole ring, an oxazole ring, an isoxazole ring, a benzoxazole ring, a furan ring, a benzo[b]furan ring, a thiophene ring, a benzo[b]thiophene ring, a pyrrolidine ring, a piperidine ring, a morpholine ring, a piperazine ring, a tetrahydrofuran ring, a tetrahydropyran ring, a 4H-pyran ring, a 1,4-dihydropyridine ring, a tetradehydromorpholine ring, or a tetradehydrothiomorpholine ring;

Ze to Zg represent a group of atoms for forming a 5- or 6-membered ring other than a pyridine ring;

A represents an acidic group;

Ra represents an aryl group, a heteroaryl group, an alkyl group, a cycloalkyl group, an alkoxy group, or a cycloalkoxy group; in which the alkyl group has a tertiary or quaternary carbon atom, and the alkoxy group has a tertiary or quaternary carbon atom, or a carbon atom directly binding to an oxygen atom of the alkoxy group is a secondary or tertiary carbon atom;

$R^{EWG}$ represents an electron-withdrawing group;

Rb and Rc represent a substituent;

a0 represents an integer of 0 to 2; in which at least one of a0's in each of formulas (B1) and (B2) is 1 or 2;

a1 represents an integer of 1 or 2;

a2 represents an integer of 1 to 4; a3 represents an integer of 0 to 3; a4 represents an integer of 0 to 4; in which the sum of a2 and a3 is an integer of 1 to 4; and the ligands represented by any one of formulas (B5) to (B8) each have at least one acidic group.

(11) The photoelectric conversion element described in item (10), wherein LD in formula (I) is represented by formula (A-3), and LA in formula (I) is represented by formula (B1).

(12) The photoelectric conversion element described in item (10), wherein LD in formula (I) is represented by formula (A-3), and LA in formula (I) is represented by formula (B2).

(13) The photoelectric conversion element described in item (10), wherein LD in formula (I) is represented by formula (A-3), and LA in formula (I) is represented by formula (B3) or (B4).

(14) The photoelectric conversion element described in item (10), wherein LD in formula (I) is represented by formula (A-3), and LA in formula (I) is represented by any one of formulas (B5) to (B8).

(15) The photoelectric conversion element described in any one of items (6) to (14), wherein LD in formula (I) is a ligand represented by formula (A-4):

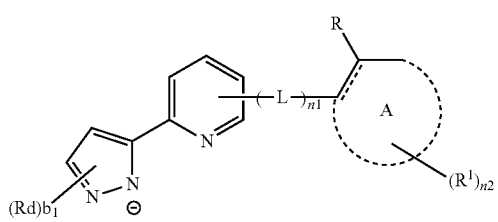

Formula (A-4)

wherein, in formula (A-4), R, $R^1$, n1, and n2 have the same meaning as those in formula (A), respectively; the ring A has the same meaning as that in formulas (A) and (A-1); Rd represents an alkyl group, a cycloalkyl group, an alkoxy group, a cycloalkoxy group, an alkylthio group, a cycloalkylthio group, an amino group, an alkylamino group, a cycloalkylamino group, an arylamino group, a heterocyclic amino group, a halogen atom, a cyano group, an alkoxycarbonyl group, a cycloalkoxycarbonyl group, or an aromatic group;

b1 represents an integer of 0 to 2; and when b1 is 2, two Rd's may be bonded to each other to form a ring.

(16) The photoelectric conversion element described in any one of items (6) to (14), wherein LD in formula (I) is a ligand represented by formula (A-5):

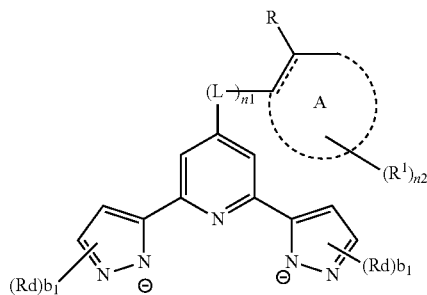

Formula (A-5)

wherein, in formula (A-5), R, $R^1$, n1, and n2 have the same meaning as those in formula (A), respectively; the ring A has the same meaning as that in formulas (A) and (A-1);

Rd represents an alkyl group, a cycloalkyl group, an alkoxy group, a cycloalkoxy group, an alkylthio group, a cycloalkylthio group, an amino group, an alkylamino group, a cycloalkylamino group, an arylamino group, a heterocyclic amino group, a halogen atom, a cyano group, an alkoxycarbonyl group, a cycloalkoxycarbonyl group, or an aromatic group;

b1 represents an integer of 0 to 2; and when b1 is 2, two Rd's may be bonded to each other to form a ring.

(17) The photoelectric conversion element described in any one of items (7) to (16), wherein the ring A or the ring B is a thiophene ring or a benzene ring.

(18) The photoelectric conversion element described in any one of items (1) to (17), wherein a co-adsorbent having one or more acidic groups is carried on the semiconductor fine-particles.

(19) The photoelectric conversion element described in item (18), wherein the co-adsorbent is represented by formula (CA):

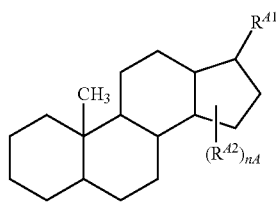

Formula (CA)

wherein, in formula (CA), $R^{41}$ represents a substituent having an acidic group; $R^{42}$ represents a substituent; and nA represents an integer of 0 or more.

(20) The photoelectric conversion element described in any one of items (1) to (19), wherein a redox-based compound contained in the electrolyte is a cobalt complex.

(21) A dye-sensitized solar cell, comprising the photoelectric conversion element described in any one of items (1) to (20).

(22) A metal complex dye, which has at least one terdentate ligand having at least one acidic group; wherein at least one ligand coordinating to a metal atom M has an sp2 carbon atom; a cyclic group binds to the sp2 carbon atom; in a circle position connecting through a carbon atom(s) from an atom of the cyclic group directly binding to the sp2 carbon atom, a substituent R is substituted at an atom of an α-position or β-position to the atom of the cyclic group directly binding to the sp2 carbon atom, with the substituent R being selected from a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, or a silyloxy group; and when the atom of the α-position or β-position to which the substituent R binds is defined as G1 and the atom of the substituent R which directly binds to the atom G1 is defined as G2, an angle θ (∠MG1G2) formed by the metal atom M, the atom G1 and the atom G2, which is centered on the atom G1, is 150° or less.

(23) A metal complex dye, which is represented by formula (I):

wherein, in formula (I), M represents Ru or Os; LD represents a bidentate or terdentate ligand represented by formula (A); LA represents a terdentate ligand represented by formula (B); X represents a monodentate ligand; CI represents a counter ion in the case where the counter ion is necessary to neutralize a charge in formula (I); m1 represents 1 or 2; m2 represents 1; and m3 represents 0 or 1;

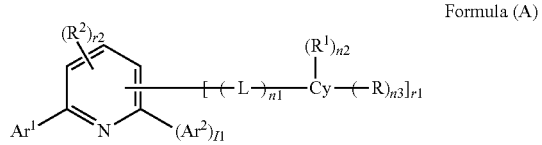
Formula (A)

wherein, in formula (A), Cy represents a cyclic group; R represents a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, or a silyloxy group; $R^1$ represents a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, a silyloxy group, an aryl group, or a heteroaryl group; $R^2$ represents a substituent;
$Ar^1$ and $Ar^2$ each independently represent a carbocyclic aromatic group having an anion, a nitrogen-containing aromatic group having a lone electron pair, or a nitrogen-containing aromatic group having an anion;
L represents an ethenylene group, an ethynylene group, an arylene group, or a heteroarylene group;
n1 represents an integer of 0 to 3; n2 represents an integer of 0 to 4; n3 represents 1 or 2; r1 represents an integer of 1 to 3; r2 represents an integer of 0 to 2; and l1 represents 0 or 1;

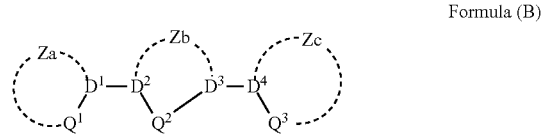
Formula (B)

wherein, in formula (B), Za, Zb and Zc each independently represent a group of atoms for forming a 5- or 6-membered ring; in which at least one of the rings formed by Za, Zb and Zc has an acidic group;

$Q^1$ to $Q^3$ each independently represent a nitrogen atom having a lone electron pair, a nitrogen atom having an anion, or a carbon atom having an anion; and
$D^1$ to $D^4$ each independently represent a carbon atom or a nitrogen atom.

(24) The metal complex dye described in item (23), wherein LD in formula (I) is represented by formula (A-3), and wherein LA in formula (I) is represented by any one of formulas (B1) to (B8):

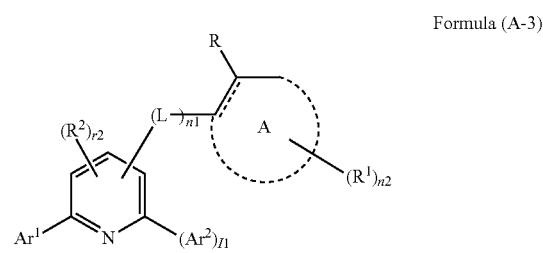
Formula (A-3)

wherein, in formula (A-3), R represents a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, or a silyloxy group; $R^1$ represents a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, a silyloxy group, an aryl group, or a heteroaryl group; $R^2$ represents a substituent;
$Ar^1$ and $Ar^2$ each independently represent a carbocyclic aromatic group having an anion, a nitrogen-containing aromatic group having a lone electron pair, or a nitrogen-containing aromatic group having an anion;
L represents an ethenylene group, an ethynylene group, an arylene group, or a heteroarylene group;
l1 represents 0 or 1; n1 represents an integer of 0 to 3; n2 represents an integer of 0 to 4;
r2 represents an integer of 0 to 2; when there are a plurality of $R^1$'s, these may be bonded to each other to form a condensed ring structure;
a ring A represents a 5- or 6-membered cyclic group; in which R and $R^1$ do not bind together to form a ring; and a broken line described between an atom of a bonding hand in the group and the binding position of R means that this portion may be a single bond or a double bond;

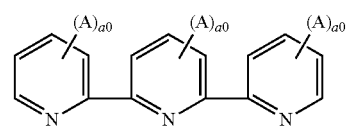
Formula (B1)

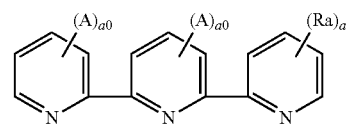
Formula (B2)

-continued

Formula (B3)
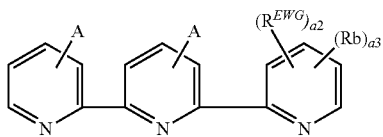

Formula (B4)
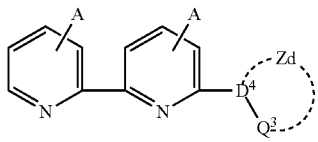

Formula (B5)
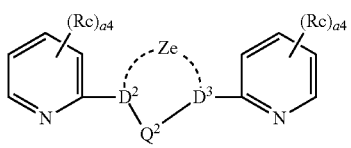

Formula (B6)
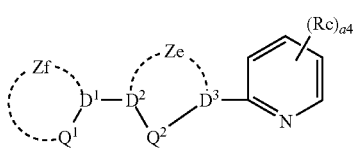

Formula (B7)
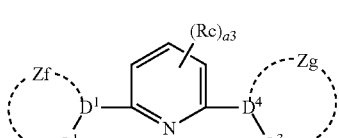

Formula (B8)
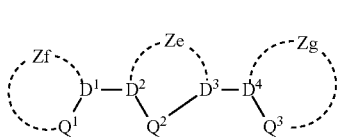

wherein, in formulas (B-1) to (B-8), $Q^1$ to $Q^3$ and $D^1$ to $D^4$ have the same meaning as those in formula (B), respectively;

Zd represent a group of atom for forming a benzene ring, a naphthalene ring, an anthracene ring, a phenanthrene ring, a pyrene ring, a perylene ring, a pyrrole ring, an indole ring, an imidazole ring, a benzoimidazole ring, a pyrazole ring, a pyrazine ring, a pyrimidine ring, a benzopyrimidine ring, a pyridazine ring, a benzopyridazine ring, a triazole ring, a benzotriazole ring, a tetrazole ring, an indazole ring, a triazine ring, a purine ring, a quinoline ring, an isoquinoline ring, a quinazoline ring, a thiazole ring, a benzothiazole ring, an isothiazole ring, an oxazole ring, an isoxazole ring, a benzoxazole ring, a furan ring, a benzo[b]furan ring, a thiophene ring, a benzo[b]thiophene ring, a pyrrolidine ring, a piperidine ring, a morpholine ring, a piperazine ring, a tetrahydrofuran ring, a tetrahydropyran ring, a 4H-pyran ring, a 1,4-dihydropyridine ring, a tetradehydromorpholine ring, or a tetradehydrothiomorpholine ring;

Ze to Zg represent a group of atom for forming a 5- or 6-membered ring other than a pyridine ring;

A represents an acidic group;

Ra represents an aryl group, a heteroaryl group, an alkyl group, a cycloalkyl group, an alkoxy group, or a cycloalkoxy group; in which the alkyl group has a tertiary or quaternary carbon atom, and the alkoxy group has a tertiary or quaternary carbon atom, or a carbon atom directly binding to an oxygen atom of the alkoxy group is a secondary or tertiary carbon atom;

$R^{EWG}$ represents an electron-withdrawing group;

Rb and Rc represent a substituent;

a0 represents an integer of 0 to 2; in which at least one of a0's in each of formulas (B1) and (B2) is 1 or 2;

a1 represents an integer of 1 or 2;

a2 represents an integer of 1 to 4; a3 represents an integer of 0 to 3; a4 represents an integer of 0 to 4; in which the sum of a2 and a3 is an integer of 1 to 4; and the ligands represented by any one of formulas (B5) to (B8) each have at least one acidic group.

(25) A dye solution, dissolved therein the metal complex dye described in any one of items (22) to (24).

(26) The dye solution described in item (25), wherein, in an organic solvent, the metal complex dye is contained in an amount of from 0.001 to 0.1% by mass, and water is limited to 0.1% by mass or less.

(27) The dye solution described in item (25) or (26), further containing a co-adsorbent.

(28) The dye solution described in item (27), wherein the co-adsorbent is represented by formula (CA):

Formula (CA)
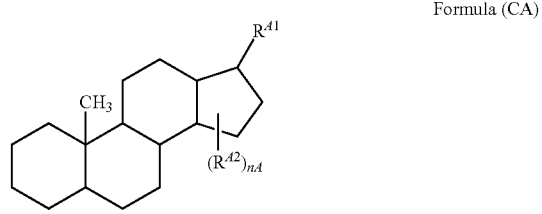

wherein, in formula (CA), $R^{41}$ represents a substituent having an acidic group; $R^{42}$ represents a substituent; and nA represents an integer of 0 or more.

(29) A compound, represented by formula (A-3):

Formula (A-3)
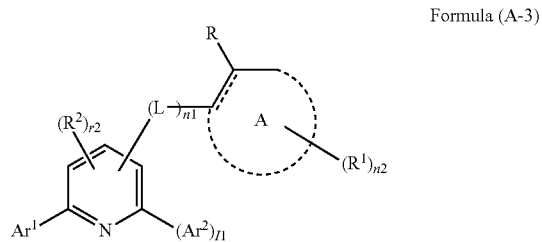

wherein, in formula (A-3), R represents a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, or a silyloxy group; $R^1$ represents a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, a silyloxy group, an aryl group, or a heteroaryl group; $R^2$ represents a substituent;

$Ar^1$ and $Ar^2$ each independently represent a carbocyclic aromatic group having an anion, a nitrogen-containing aromatic group having a lone electron pair, or a nitrogen-containing aromatic group having an anion;

L represents an ethenylene group, an ethynylene group, an arylene group, or a heteroarylene group;

l1 represents 0 or 1; n1 represents an integer of 0 to 3; n2 represents an integer of 0 to 4;

r2 represents an integer of 0 to 2;

a ring A represents a 5- or 6-membered cyclic group; in which R and $R^1$ do not bind together to form a ring; and a broken line described between an atom of a bonding hand in the group and the binding position of R means that this portion may be a single bond or a double bond.

(30) The compound described in item (29), which is a compound represented by formula (A-4'):

Formula (A-4')

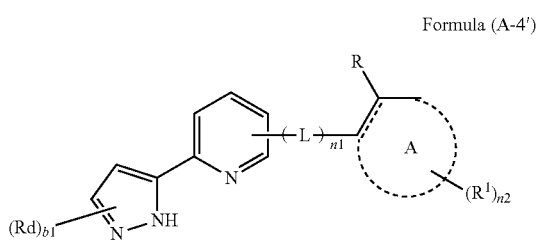

wherein, in formula (A-4), R, $R^1$, Rd, L, b1, n1, n2, and the ring A have the same meaning as those in formula (A-3), respectively.

(31) The compound described in item (29), which is a compound represented by formula (A-5'):

Formula (A-5')

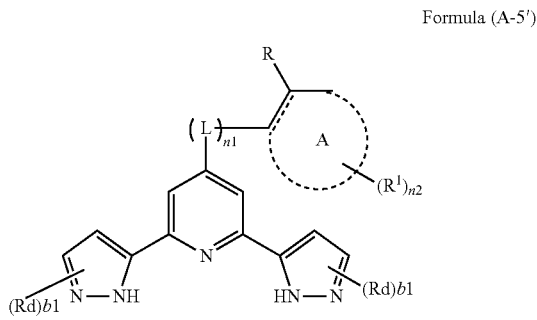

wherein, in formula (A-5'), R, $R^1$, Rd, L, b1, n1, n2, and the ring A have the same meaning as those in formula (A-3), respectively.

In the present specification, unless otherwise specified, with respect to the carbon-carbon double bond, in a case where the E configuration or the Z configuration exists in the molecule, it may be either one of the two configurations or a mixture thereof. When there are two or more substituents, linking groups, ligands or the like (hereinafter referred to as substituents or the like) represented by a specific symbol, or when two or more substituents or the like are defined at the same time or alternatively, each of the substituents or the like may be the same or different from one another, unless otherwise specified. This is also applied to definition of the number of substituents or the like. Further, when a plurality of substituents or the like are close to one another (particularly adjacent to each other), they may be linked to one another to form a ring, unless otherwise specified. Further, a ring, for example, an aliphatic ring, an aromatic ring, or a heterocycle, may be ring-fused to form a fused ring.

In the present specification, each substituent may be further substituted with another substituent, unless otherwise specified.

Advantageous Effects of Invention

According to the present invention, by balancing: reduction of variation in performance, and improvement of both of photoelectric conversion efficiency and durability, a metal complex dye excellent in performances can be provided; and the use of this metal complex dye makes it possible to provide: a photoelectric conversion element and a dye-sensitized solar cell, each of which is excellent in performances; and a dye solution containing the metal complex dye and a compound which is useful as a ligand of the metal complex dye.

Other and further features and advantages of the invention will appear more fully from the following description, appropriately referring to the accompanying drawings.

MODE FOR CARRYING OUT THE INVENTION

The present invention resides in, as shown below: a metal complex dye having at least one terdentate ligand having at least one acidic group; a photoelectric conversion element and a dye-sensitized solar cell, each of which has the metal complex dye; a dye solution containing the metal complex dye; and a compound which is useful as a ligand of the metal complex dye. Firstly, the metal complex dye is explained in detail.

<<Metal Complex Dye>>

The metal complex dye of the present invention has at least one terdentate ligand having at least one acidic group; wherein at least one ligand coordinating to a metal atom M has an sp2 carbon atom; a cyclic group binds to the sp2 carbon atom; in the circle position connecting through a carbon atom(s) from an atom of the cyclic group directly binding to the sp2 carbon atom, a substituent R is substituted at an atom of the α-position or β-position to the atom of the cyclic group directly binding to the sp2 carbon atom, with the substituent R being selected from a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, or a silyloxy group; and when the atom of the α-position or β-position to which the substituent R binds is defined as G1 and the atom of the substituent R which directly binds to the atom G1 is defined as G2, an angle θ formed by the metal atom M, the atom G1 and the atom G2, which is centered on the atom G1 (∠MG1G2) is 150° or less. Herein, as a value of the ∠MG1G2, the angle which is 180° or less (but not the angle over 180°) is employed.

The metal complex dye of the present invention is preferably a metal complex dye having a parasol-type molecular shape. The parasol-type metal complex dye means a metal complex dye, which has a cyclic group on an sp2 carbon atom of a basic skeleton of the ligand (a minimum skeleton enough to coordinate) or an sp2 carbon atom of a conjugated system (conjugated chain) with the basic skeleton, and which has a substituent at an atom of α-position or β-position with respect to the atom of the cyclic group directly binding to the sp2 carbon atom, with the substituent being oriented not in a direction of getting away from a central metal atom, but so as to cover the central metal atom. For example, when sunlight is irradiated from the substituent side, the substituent is oriented so as to shade the light which shines on the central metal atom, like a fully open, or partially open, or one-side open parasol, rather than a closed parasol.

Figure 5:
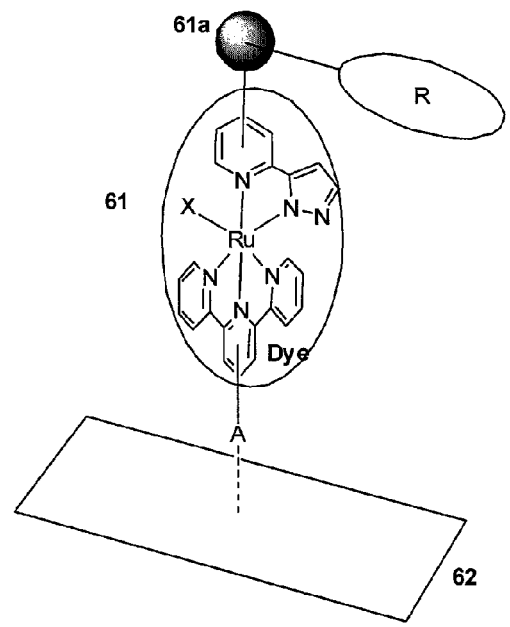
FIG. 5 is a schematic view of the state in which the metal complex dye is adsorbed on a semiconductor fine-particle surface through an acidic group.

In showing this orientation schematically, for example, in the case of a metal complex dye having an octahedral structure, in which a terpyridine of a terdentate ligand having an acidic group, a ligand of a 5-(2-pyridyl)pyrazole skeleton of a bidentate ligand, and a monodentate ligand (X), each coordinate to a Ru metal, this outlines a structure as shown in FIG. 5.

In this structure, the ligand of the 5-(2-pyridyl)pyrazole skeleton has a cyclic group (61a) having a substituent R.

This metal complex dye 61 having the substituent R on the cyclic group 61a, is adsorbed on a semiconductor fine-particle plane surface 62 through the acidic group.

Figure 6:
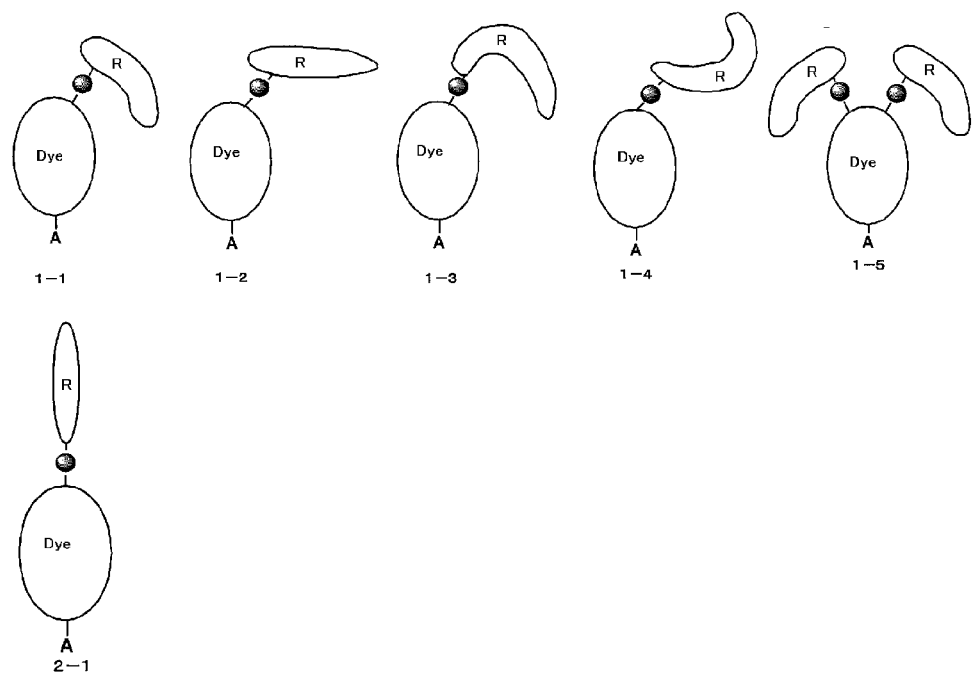
FIG. 6 is schematic views showing various kinds of orientation of substituents which bind to a cyclic group.

In the present invention, preferred metal complex dyes have a structure, for example, of any one of 1-1 to 1-5 as shown schematically in FIG. 6. Contrary to the above, one of a structure of 2-1 is the closed parasol, and even if the sunlight is shined from the tip of the parasol, the central metal atom is not substantially shadowed.

In this way, due to the substituent (substituent R in the above), because the substituent does not extend right above, but extends at an angle, the metal complex dye molecule can inhibit effectively for the redox system (for example, $I_3^-$) from access to semiconductor fine-particles, whereby reverse electron transfer from the redox system can be prevented.

—Angle θ (∠MG1G2)—

Figure 7:
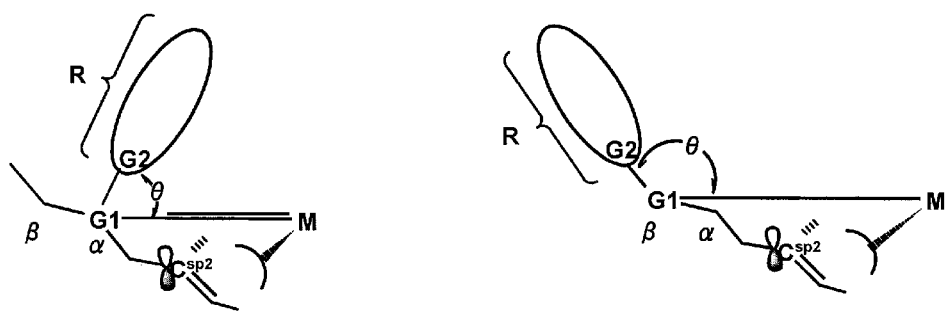
FIG. 7 is schematic views showing angles θ (∠MG1G2) at the α-position or β-position of the cyclic group.

The angle θ (∠MG1G2) formed by the metal atom M, the atom G1, and the atom G2, is shown specifically as in FIG. 7. The atom G2 which binds to the cyclic group at the α-position thereof is shown in the left side of FIG. 7, while the atom G2 at the β-position thereof in the right side. In FIG. 7, the sp2 carbon atom is shown by $C^{sp2}$.

Further, the α-position and the β-position of the cyclic group indicate a position of an atom binding adjacently to the carbon atom of the cyclic group which binds to the sp2 carbon atom, and next to the carbon atom of the cyclic group binding to the sp2 carbon atom is the α-position, and next to the next is the β-position, and further next to the next is the γ-position.

In the present invention, the α-position and the β-position are located at a circle position connecting through a carbon atom(s) from the atom of the cyclic group which directly binds to the sp2 carbon atom, and a connection between the atom of the cyclic group which binds directly to the sp2 carbon atom and the atom having the substituent thereon is a carbon atom or a linking of a carbon atom and a carbon atom.

Specifically, formula (A-1) has the substituent R at the α-position of the cyclic group, while formula (A-2) has the substituent R at the β-position of the cyclic group, and the connecting portion ranging, from the position of a bonding hand of the cyclic group which binds to the sp2 carbon atom to the atom at which the substituent R is substituted, comprises one carbon atom or two carbon atoms.

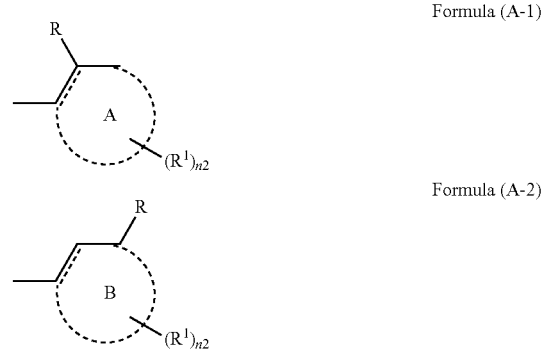

Formula (A-1)

Formula (A-2)

In formulae, R is a specific substituent R on which the present invention focuses attention.

Details of formulae (A-1) and (A-2) are explained in relation to formula (A).

The angle θ (∠MG1G2) formed by the metal atom M, the atom G1, and the atom G2 can be measured according to various kinds of methods. It is easy to determine the angle from a molecular structure obtained by optimization of the structure according to density-functional-theory calculation (DFT calculation).

In the present invention, calculation is carried out using lan l2 dz as a base function, according to density-functional-theory calculation. Thus, the most stable structure is determined, and from the thus-determined most stable structure, the angle θ (∠MG1G2) can be obtained. In the present invention, Gaussian 09 (manufactured by Gaussian) is used.

In the present invention, the angle θ (∠MG1G2) is 150° or less. The maximum angle is 180° because it is not a vectorial angle.

In the present invention, the angle θ (∠MG1G2) is preferably 120° or less, and more preferably an acute angle (90° or less).

Further, in the present invention, in consideration to makes the angle θ (∠MG1G2) small, those in which the substituent R binds at the α-position of the cyclic group are preferred.

—Relationship to Length of Substituent R—

In the present invention, more preferable molecular structure is the case that a length of the substituent R in the present invention is preferably longer than ½ times of the length from the metal atom M to the atom (G1) of the cyclic group at which the substituent R is substituted, and more preferably longer than 1 time thereof. When the length of the substituent R is long as described above, inhibition of the redox system (e.g. $I_3^-$) from access to the semiconductor fine-particles becomes more effective.

The relationship of the length can be expressed by the number of liking chains which link those atoms.

That is, in the present invention, preferred is the case where the maximum linking chain number $N_R$ of the linking chain numbers (bond numbers) of a linking chain linking the atom G1 with the atom located at the furthest position through a linkage of the substituent R is more than ½ times of the minimum linking chain number $N_{M-G1}$ of the linking chain numbers (bond numbers) of a linking chain linking from the metal atom M to the atom G1, more preferred is the case of more than 0.8 times, and particularly preferred is the case of more than 1 time. In the ring structure, although the linking chain number differs depending on a right-hand turn or a left-hand turn, a shorter linking chain number is employed. Further, the substituent R is not ring-fused with the cyclic group. This cause is due to the reason that if the substituent R is ring-fused, dye-covering effect decreases drastically.

—Substituent R—

In the present invention, the cyclic group has a specific substituent R.

The substituent R is a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, or a silyloxy group.

The linear or branched alkyl group may have a substituent. The linear or branched alkyl group has preferably 1 to 30 carbon atoms, more preferably 4 to 30 carbon atoms, further preferably 5 to 26 carbon atoms, and particularly preferably 6 to 20 carbon atoms.

Examples thereof include methyl, ethyl, n-butyl, n-pentyl, n-hexyl, n-octyl, 2-ethylhexyl, n-decyl, isodecyl, s-decyl, n-dodecyl, n-hexadecyl, isohexadecyl, n-eicosyl, n-hexacosyl, isooctacosyl, trifluoromethyl, and pentafluoroethyl.

The cycloalkyl group may have a substituent. The cycloalkyl group has preferably 3 to 30 carbon atoms, more preferably 5 to 30 carbon atoms, further preferably 6 to 26 carbon atoms, and particularly preferably 6 to 20 carbon atoms.

Examples thereof include cyclopropyl, cyclopentyl, cyclohexyl, cycloheptyl, and cyclooctyl. The cycloalkane which is a ring of this group may be ring-fused with an aliphatic ring, an aromatic ring, or a heterocycle.

The alkoxy group may have a substituent. The alkoxy group has preferably 1 to 30 carbon atoms, more preferably 4 to 30 carbon atoms, further preferably 5 to 26 carbon atoms, and particularly preferably 6 to 20 carbon atoms.

Examples thereof include methoxy, ethoxy, n-butoxy, n-pentoxy, n-hexyloxy, n-octyloxy, 2-ethylhexyloxy, n-decyloxy, isodecyloxy, s-decyloxy, n-dodecyloxy, n-hexadecyloxy, isohexadecyloxy, n-eicosyloxy, n-hexacosyloxy, and isooctacosyloxy.

The cycloalkoxy group may have a substituent. The cycloalkoxy group has preferably 3 to 30 carbon atoms, more preferably 5 to 30 carbon atoms, further preferably 6 to 26 carbon atoms, and particularly preferably 6 to 20 carbon atoms.

Examples thereof include cyclopropyloxy, cyclopentyloxy, cyclohexyloxy, cycloheptyloxy, and cyclooctyloxy. The cycloalkane which is a ring of this group may be ring-fused with an aliphatic ring, an aromatic ring, or a heterocycle.

The aryloxy group includes those having a heteroaromatic ring in which an aryl ring is an aromatic ring, that is, it includes a carbocyclic aromatic ring and a heteroaromatic ring. Thus, the aryloxy group includes a carbocyclic aryloxy group and a heteroaryloxy group. The aryloxy group may have a substituent. The aryloxy group has preferably 5 to 30 carbon atoms, more preferably 5 to 25 carbon atoms, further preferably 5 to 20 carbon atoms, and particularly preferably 5 to 16 carbon atoms. Examples thereof include phenoxy, naphthoxy, imidazoyloxy, benzimidazoyloxy, pyridine-4-yloxy, pyrimidinyloxy, quinazolynyloxy, purinyloxy, and thiophene-3-yloxy.

As a hetero ring of the heteroaryloxy group, a thiophene ring is preferred.

The alkylthio group may have a substituent. The alkylthio group has preferably 1 to 30 carbon atoms, more preferably 4 to 30 carbon atoms, further preferably 5 to 26 carbon atoms, and particularly preferably 6 to 20 carbon atoms.

Examples thereof include methylthio, ethylthio, n-butylthio, n-pentylthio, n-hexylthio, n-octylthio, 2-ethylhexylthio, n-decylthio, isodecylthio, s-decylthio, n-dodecylthio, n-hexadecylthio, isohexadecylthio, n-eicosylthio, n-hexacosylthio, and isooctacosylthio.

The cycloalkylthio group may have a substituent. The cycloalkylthio group has preferably 3 to 30 carbon atoms, more preferably 5 to 30 carbon atoms, further preferably 6 to 26 carbon atoms, and particularly preferably 6 to 20 carbon atoms.

Examples thereof include cyclopropylthio, cyclopentylthio, cyclohexylthio, cycloheptylthio, and cyclooctylthio. The cycloalkane which is a ring of this group may be ring-fused with an aliphatic ring, an aromatic ring, or a heterocycle.

The arylthio group includes those having a heteroaromatic ring in which an aryl ring is an aromatic ring, that is, it includes a carbocyclic aromatic ring and a heteroaromatic ring. Thus, the arylthio group includes a carbocyclic arylthio group and a heteroarylthio group. The arylthio group may have a substituent. The arylthio group has preferably 5 to 30 carbon atoms, more preferably 5 to 25 carbon atoms, further preferably 5 to 20 carbon atoms, and particularly preferably 5 to 16 carbon atoms.

Examples thereof include phenylthio, naphthylthio, imidazoylthio, benzimidazoylthio, pyridine-4-ylthio, pyrimidinylthio, quinazolynylthio, purinylthio, and thiophene-3-ylthio.

As a hetero ring of the heteroarylthio group, a thiophene ring is preferred.

Among the amino group, the alkylamino group, the cycloalkylamino group, the arylamino group and the heterocyclic amino group, the alkylamino group may have a substituent. The alkylamino group has preferably 1 to 30 carbon atoms, and more preferably 2 to 30 carbon atoms. Examples thereof include ethylamino, diethylamino, 2-ethylhexylamino, bis(2-ethylhexyl)amino, n-octadecylamino, and n-octadecylamino.

The cycloalkylamino group may have a substituent. The cycloalkylamino group has preferably 3 to 30 carbon atoms, more preferably 5 to 30 carbon atoms, further preferably 6 to 26 carbon atoms, and particularly preferably 6 to 20 carbon atoms.

Examples thereof include cyclopropylamino, dicyclopropylamino, N-cyclopropyl-N-ethylamino, cyclopentylamino, dicyclopentylamino, N-cyclopentyl-N-methylamino, cyclohexylamino, dicyclohexylamino, cycloheptylamino, and cyclooctylamino. The cycloalkane which is a ring of this group may be ring-fused with an aliphatic ring, an aromatic ring, or a heterocycle.

The arylamino group includes those having a heteroaromatic ring in which an aryl ring is an aromatic ring, that is, it includes a carbocyclic aromatic ring and a heteroaromatic ring. Thus, the arylamino group includes a carbocyclic arylamino group and a heteroarylamino group. The arylamino group may have a substituent. The arylamino group has preferably 5 to 30 carbon atoms, more preferably 5 to 25 carbon atoms, further preferably 5 to 20 carbon atoms, and particularly preferably 5 to 16 carbon atoms.

Examples thereof include phenylamino, N-phenyl-N-ethylamino, naphthylamino, imidazoylamino, benzimidazoylamino, pyridine-4-ylamino, pyrimidinylamino, quinazolynylamino, purinylamino, and thiophene-3-ylamino.

The heterocyclic amino group is a heterocyclic amino group other than the heteroarylamino group. The heterocyclic amino group may have a substituent. The heterocyclic amino group has preferably 0 to 30 carbon atoms, more preferably 1 to 25 carbon atoms, further preferably 2 to 20 carbon atoms, and particularly preferably 2 to 16 carbon atoms. Further, as the hetero ring, those in which a ring-constituting hetero atom is selected from an oxygen atom, a sulfur atom, and a nitrogen atom are preferred, and as the number of ring members, a 5- to 7-numbered ring is preferred, and a 5- or 6-numbered ring is more preferred.

Examples thereof include pyroridine-3-ylamino, imidazolidinylamino, benzimidazolidinylamino, piperidine-4-ylamino, and tetrahydrothiophene-3-ylamino.

The silyl group includes an alkylsilyl group, a cycloalkylsilyl group, an arylsilyl group, an alkyloxysilyl group, a cycloalkyloxysilyl group, and an aryloxysilyl group. The silyl group has preferably 3 to 30 carbon atoms, more preferably 3 to 24 carbon atoms, further preferably 3 to 20 carbon atoms, and particularly preferably 3 to 18 carbon atoms.

Of the silyl group, preferred are an alkylsilyl group, a cycloalkylsilyl group, or an arylsilyl group.

Examples thereof include trimethylsilyl, triethylsilyl, t-butyldimethylsilyl, cyclohexyldimethylsilyl, triisopropylsilyl, t-butyldiphenylsilyl, methyldimethoxysilyl, phenyldimethoxysilyl, and phenoxyldimethylsilyl.

The silyloxy group includes an alkylsilyloxy group, a cycloalkylsilyloxy group, and an arylsilyloxy group. The silyloxy group has preferably 3 to 30 carbon atoms, more preferably 3 to 24 carbon atoms, further preferably 3 to 20 carbon atoms, and particularly preferably 3 to 18 carbon atoms.

Examples thereof include trimethylsilyloxy, triethylsilyloxy, t-butyldimethylsilyloxy, triisopropylsilyloxy, cyclohexyldimethylsilyloxy, and t-butyldiphenylsilyloxy.

Of the substituent R, preferred are a straight chain or branched alkyl group, a cycloalkyl group, an alkoxy group, a cycloalkoxy group, an alkylthio group, a cycloalkylthio group, an amino group, an alkylamino group, a cycloalkylamino group, and an arylamino group, and more preferred are a straight chain or branched alkyl group, a cycloalkyl group, an alkoxy group, a cycloalkoxy group, an alkylamino group, a cycloalkylamino group, and an arylamino group, and further preferred are a straight chain or branched alkyl group, an alkoxy group, and an alkylamino group, and particularly preferred are a straight chain or branched alkyl group, and an alkoxy group.

Those which have two or more substituents R on the cyclic group are also preferred, and when there are a plurality of α-positions or β-positions, those which have substituents R at a plurality of α-positions or β-positions are preferred. The substituent R is not ring-fused with the cyclic group.

—Cyclic Group—

In the present invention, the substituent R is located at the α-position or the β-position of the cyclic group which binds to the sp2 carbon atom.

Examples of the cyclic group include a saturated, unsaturated, or aromatic ring-carbocycle, and a hetero ring including a heteroaromatic ring. Further, as for the hetero ring, the hetero atom as a ring-constituent atom thereof is preferably a nitrogen atom, a sulfur atom, and an oxygen atom. The cyclic group is preferably a cycloalkyl group, a cycloalkenyl group, an aryl group, and a heterocyclic group, each of which may have a substituent, and may be ring-fused with another ring or the same ring.

In the cyclic group, a direction of the substituent R, that is, the angle θ (∠MG1G2) is fixed, and as a result, a probability of obtaining a desirable angle is improved and it can be designed freely.

As a cycloalkyl group, a cycloalkyl group having a 3- to 7-membered ring is preferred, and examples thereof include cyclopropyl, cyclopentyl, cyclohexyl, and cycloheptyl.

As a cycloalkenyl group, a cycloalkenyl group having a 3- to 7-membered ring is preferred, and examples thereof include cyclopentenyl, cyclohexenyl, and cycloheptenyl.

Examples of the aryl group include phenyl and naphthyl.

As a heterocyclic group, those which have at least one oxygen atom, sulfur atom, or nitrogen atom as a ring-constituent atom are preferred, and a 5- to 7-membered heterocyclic group is preferred.

Examples of a hetero ring of the heterocyclic group include a thiophene ring, a furan ring, a pyrrole ring, an imidazole ring, a pyrazole ring, a pyridine ring, a pyrazine ring, a pyridazine ring, a tetrahydrothiophene ring, a tetrahydrofuran ring, a pyrrolidine ring, a pyrroline ring, an imidazolidine ring, a pyrazolidine ring, a piperidine ring, a piperazine ring, and a morpholine ring.

In the present invention, the cyclic group is preferably an aromatic ring, and more preferably an aryl group (a carbocyclic aromatic ring group) and a heteroaromatic ring group.

As a preferable specific group, preferred are cyclohexyl, pheny, and a group in which a hetero ring is thiophene (2-thieny in particular), more preferred are pheny and thiophene, and pheny is particularly preferred.

—Ligand Having Sp2 Carbon Atom—

In the present invention, a basic skeleton of the ligand has at least one sp2 carbon atom, and the sp2 carbon atom is preferably a ring-forming atom, or a carbon atom of a conjugated linking group which links an aromatic ring with the cyclic group (for example, an ethenylene group, an ethynylene group, an arylene group, a heteroarylene group, or a linking group in which these groups are repeated), and more preferably a ring-forming atom from a viewpoint of durability to nucleophilic species. The conjugated linking group is preferably an ethenylene group, and more preferred is a carbon atom at a terminal of ethylene which directly binds to an aromatic ring ($C_2$ in the aromatic ring-$C_1$=$C_2$).

The sp2 carbon atom-constituting ring may be that the sp2 carbon atom forms an unsaturated bond together with another constituting atom in the ring, or may be that the sp2 carbon atom forms a double bond together with an atom substituted on the ring, which is not a ring-constituting atom (for example, $>C^{sp2}$=$CH_2$ in fulvalene, and methine $>C^{sp2}$=N—: in which, the symbol ">" represents a ring). It is preferred that the sp2 carbon atom forms an unsaturated bond together with another constituting atom in the ring.

The ring which is formed together with the sp2 carbon atom includes the above-described cyclic group.

The cyclic group is that the thus-formed ring contains an atom which coordinates to the metal atom M, or that the thus-formed ring has a substituent which coordinates the ring (for example, an amino group, a hydroxyl group, an anionic group, or the like). In the present invention, it is preferred that the formed ring contains an atom which coordinates to the metal atom M.

As the cyclic group in which the formed ring contains an atom which coordinates to the metal atom M, a heterocyclic group is preferred, a 5- or 6-membered heterocyclic group is more preferred, and a hetero ring in which the atom which coordinates to the metal atom M is a nitrogen atom is further preferred.

As such a hetero ring, an aromatic nitrogen-containing hetero ring is preferred, and examples thereof include a pyrrole ring, an imidazole ring, a pyrazole ring, a triazole ring, a tetrazole ring, a pyridine ring, a pyrazine ring, an indol ring, and an indazole ring.

As for these rings, one in which two hetero rings are bonded, and one in which three hetero rings are bonded, are preferred as a ligand. Furthermore, one in which the hetero ring(s) is/are bonded with another aromatic ring, is preferred.

Examples of the another aromatic ring include an aryl ring, a heteroaromatic ring, or an aryl ring or heteroaromatic ring each having an anion which is formed from any of these. Especially, one in which an aromatic nitrogen-containing hetero ring and at least one of an aryl ring anion or aromatic hetero ring anion (the anion is an anion of a cyclic constituent atom, to coordinates to the metal atom M) are bonded, is particularly preferred.

That is, in the present invention, a bidentate ligand or a terdentate ligand is preferred, and from the viewpoint of suppressing elimination of the ligand, more preferred is a terdentate ligand.

In the present invention, in the case where the ligand having at least one sp2 carbon atom has a plurality of sp2 carbon atoms, the plurality of sp2 carbon atoms may have the cyclic group. In the present invention, the number of sp2 carbon atoms having such a cyclic group is preferably 1 or 2, and more preferably 1.

Further, in the present invention, the above-described sp2 carbon atom is preferably a ring-constituent carbon atom, or an ethylene carbon atom in the ethylene structure conjugated with an aromatic ring.

—Acidic Group—

The acidic group represents a substituent having a dissociative proton and having a pKa of 11 or lower. Examples thereof include: an acid group which shows an acid property, such as a carboxyl group, a phosphonyl group, a phosphoryl group, a sulfo group, and a boric acid group; or a group having any of these groups, and from the viewpoint of electron injection, a carboxyl group or a group having the same is preferred. Further, the acidic group may be in a dissociation form due to release of a proton, or may be a salt thereof.

The acidic group may be a group in which an acid group connects via a linking group, and the linking group includes an alkylene group, an alkynylene group, an alkenylene group, an arylene group, a divalent heterocyclic group, and a group in which these groups are combined. The alkylene group preferably has 1 to 4 carbon atoms, the alkenylene group preferably has 2 to 4 carbon atoms, the alkynylene group preferably has 2 to 4 carbon atoms, the arylene group preferably has 6 to 12 carbon atoms, and the divalent heterocycle group preferably has 0 to 12 carbon atoms.

Further, in a case where the acidic group is a salt thereof, a counter ion which forms the salt is not limited in particular. Examples thereof include a positive ion which is represented by a counter ion CI in formula (I).

In the present invention, from the viewpoint of electron transfer, an acidic group having no linking group is preferred, and a carboxyl group is preferred in particular.

The center metal in the metal complex dye is a metal that is capable of tetracoordination or hexacoordination; preferably Ru, Fe, Os, Cu, W, Cr, Mo, Ni, Pd, Pt, Co, Ir, Rh, Re, Mn, or Zn; further preferably Ru, Os, Fe, or Cu; particularly preferably Ru or Os; and most preferably Ru.

<Metal Complex Dye Represented by Formula (I)>

The metal complex dye of the present invention is preferably a metal complex dye represented by formula (I).

$$M(LD)m1(LA)m2(X)m3 \cdot CI \quad \text{Formula (I)}$$

In formula (I), M represents Ru or Os, LD represents a bidentate or terdentate ligand represented by formula (A), LA represents a terdentate ligand represented by formula (B), X represents a monodentate ligand, CI represents a counter ion in the case where the counter ion is necessary to neutralize a charge in formula (I), m1 represents 1 or 2, m2 represents 1, and m3 represents 0 or 1.

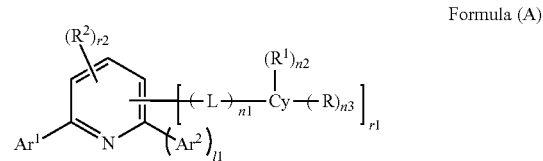

Formula (A)

In formula (A), Cy represents a cyclic group; R represents a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, or a silyloxy group; $R^1$ represents a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, a silyloxy group, an aryl group, or a heteroaryl group; and $R^2$ represents a substituent.

$Ar^1$ and $Ar^2$ each independently represent a carbocyclic aromatic group having an anion, a nitrogen-containing aromatic group having a lone electron pair, or a nitrogen-containing aromatic group having an anion.

L represents an ethenylene group, an ethynylene group, an arylene group, or a heteroarylene group. n1 represents an integer of 0 to 3, n2 represents an integer of 0 to 4, n3 represents 1 or 2, r1 represents an integer of 1 to 3, r2 represents an integer of 0 to 2, and l1 represents 0 or 1.

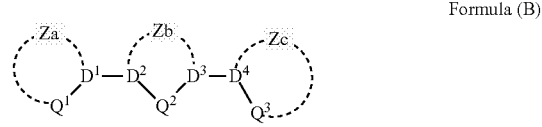

Formula (B)

In formula (B), Za, Zb and Zc each independently represent a group of atoms for forming a 5- or 6-membered ring, and at least one of the rings formed by Za, Zb and Zc has an acidic group;

$Q^1$ to $Q^3$ each independently represent a nitrogen atom having a lone electron pair, a nitrogen atom having an anion, or a carbon atom having an anion.

$D^1$ to $D^4$ each independently represent a carbon atom or a nitrogen atom.

—Ligand LD—

In the present invention, the ligand LD is categorized as a donor ligand, and is represented by formula (A).

Hereinafter, the ligand (compound) represented by formula (A) is explained in detail.

R represents the substituent R in the present invention, and Cy represents the cyclic group. When n1 is 0, the sp2 carbon atom is a carbon atom on the pyridine ring at which Cy is substituted. When n1 is from 1 to 3, the sp2 carbon atom is an sp2 carbon atom in L.

Examples of a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, a silyloxy group, each of which is represented by $R^1$, include those groups explained about R. Further, the aromatic group includes a carbon ring and a heteroaromatic ring, and is preferably a phenyl group or a thienyl group, each of which may have a substituent.

The cyclic group represented by Cy is the cyclic group and a 3- to 8-membered ring is preferred. As for the ring, cycloalkane, cycloalkene, aryl ring, and hetero ring are preferred, and these rings may have a substituent and may be ring-fused with another ring or the same ring. As a ring, an aromatic ring (carbon-based aromatic ring and hetero aromatic ring) is preferred. A benzene ring and a thiophene ring are preferred in particular. The ring also preferably includes these rings with which a hetero ring or an aromatic ring is ring-fused.

Cy is preferably a group represented by formula (A-1) or (A-2).

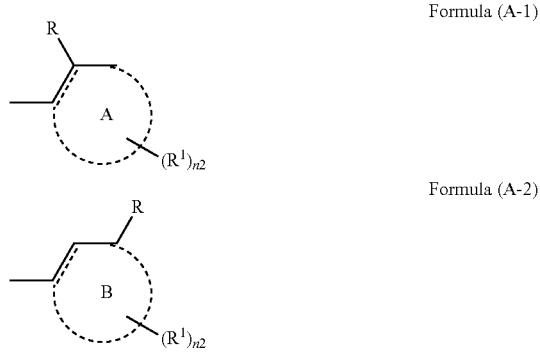

Formula (A-1)

Formula (A-2)

In formulas (A-1) and (A-2), R and $R^1$ have the same meaning as those in formula (A), respectively; the ring A and the ring B each represent a 5- or 6-membered cyclic group; in which R and $R^1$ do not bind together to form a ring. When there are a plurality of $R^1$'s, these may be bonded to each other to form a condensed ring structure; and the broken line described between the atom of a bonding hand in the above-described group and the binding position of R means that this portion may be a single bond or a double bond.

The ring A and ring B each are preferably a thiophene ring or a benzene ring.

Among the groups represented by formula (A-1) or (A-2), the group represented by formula (A-1) is preferable in the present invention.

L represents an ethenylene group, an ethynylene group, an arylene group, or a heteroarylene group. The arylene group is a divalent aromatic carbocyclic group and includes phenylene and naphthylene. As for the heteroaryl ring of the heteroarylene group, the ring-constituent hetero atom thereof includes an oxygen atom, a sulfur atom (—S—, —SO—, —SO$_2$—), a nitrogen atom, a silicon atom, and a selenium atom, and the number of ring-constituting atoms is preferably a 5- to 7-membered ring. The heteroaryl ring may be ring-fused with an alicyclic ring, an aromatic ring, or a hetero ring, and examples thereof include a thiophene ring, a benzothiophene ring, a furan ring, a pyridine ring, and those rings described about the heteroaryl rings among rings formed by Za to Zc in formula (B), or rings formed by Zd in formula (B4).

$Ar^1$ and $Ar^2$ each are preferably a nitrogen-containing aromatic group having an anion or a nitrogen-containing aromatic group having a lone electron pair, more preferably a nitrogen-containing aromatic group having an anion.

As for the ring of these cyclic groups, the aromatic carbocyclic ring includes a benzene ring and a naphthalene ring, and the nitrogen-containing aromatic ring may contain, as a ring-constituent hetero atom, either only a nitrogen atom or a nitrogen atom together with any of an oxygen atom, a sulfur atom (—S—, —SO—, —SO$_2$—), a silicon atom, and a selenium atom, and the number of ring-constituting atoms is preferably a 5- to 7-membered. The nitrogen-containing aromatic ring may be ring-fused with an alicyclic ring, an aromatic ring, or a hetero ring, and examples thereof include a thiophene ring, a benzothiophene ring, a furan ring, a pyridine ring, and those rings described about the nitrogen-containing heteroaryl rings among rings formed by Za to Zc in formula (B), or rings formed by Zd in formula (B4).

As a carbocyclic aromatic group having an anion and a nitrogen-containing aromatic group having an anion, those in which at least one of the ring-constituent atoms is an anion are preferred. These anions which coordinate to a metal atom M, or which is able to coordinate thereto are preferred.

Also note that the lone electron pair of the nitrogen-containing aromatic group having a lone electron pair means a lone electron pair which does not attribute to bond rather than π electron on an aromatic ring. At least one nitrogen atom of the nitrogen-containing aromatic ring is a nitrogen atom having a lone electron pair, and examples thereof include a nitrogen atom derived from an imidazole ring, a thiazole ring, a benzimidazole ring, a benzothiazole ring, a pyridine ring, and a quinoline ring, and a pyridine ring is preferred.

Further, these rings may be ring-fused with an alicyclic ring, an aromatic ring, or a hetero ring.

The nitrogen-containing aromatic group having an anion is preferably a group represented by any one of formulas (a-1) to (a-5); more preferably a group represented by any one of formulas (a-1), (a-2) and (a-5); and particularly preferably a group represented by formula (a-2).

(a-1)

-continued

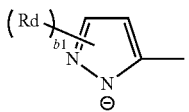
(a-2)

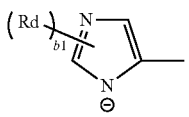
(a-3)

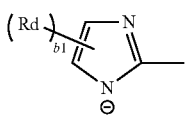
(a-4)

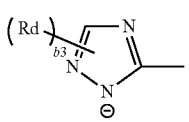
(a-5)

In formulas (a-1) to (a-5), Rd represents an alkyl group, a cycloalkyl group, an alkoxy group, a cycloalkoxy group, an alkylthio group, a cycloalkylthio group, an amino group, an alkylamino group, a cycloalkylamino group, an arylamino group, a heterocyclic amino group, a halogen atom, a cyano group, an alkoxycarbonyl group, a cycloalkoxycarbonyl group, or an aromatic group. b1 represents an integer of 0 to 2. b2 represents an integer of 0 to 3. b3 represents an integer of 0 or 1. When b1 is 2 or more, or when b2 is 2, Rd's may be bonded to each other to form a ring.

Examples of an alkyl group, a cycloalkyl group, an alkoxy group, a cycloalkoxy group, an alkylthio group, a cycloalkylthio group, an amino group, an alkylamino group, a cycloalkylamino group, an arylamino group, a heterocyclic amino group, each of which is represented by Rd, include those groups explained about the substituent R. The halogen atom is preferably a fluorine atom, a chlorine atom, or a bromine atom. The alkoxycarbonyl group is preferably an alkoxycarbonyl group having 2 to 30 carbon atoms, and examples thereof include methoxycarbonyl, ethoxycarbonyl, n-butoxycarbonyl, isopropoxycarbonyl, 3-ethylhexyloxycarbonyl, and n-octadecyloxycarbonyl. The cycloalkoxycarbonyl group is preferably a cycloalkoxycarbonyl group having 6 to 30 carbon atoms, and examples thereof include cyclopentyloxycarbonyl, cyclohexyloxycarbonyl, cycloheptyloxycarbonyl. The aromatic group includes a carbocyclic aromatic group and a heteroaryl group, and includes rings of the groups enumerated with respect to the arylene groups and the heteroarylene group both of which are represented by L in formula (A). Also note that although L is a divalent group, the rings enumerated in L have been modified to monovalent groups.

As Rd, preferred are a straight chain or branched alkyl group, a cycloalkyl group, an aromatic group, a halogen atom, an alkoxycarbonyl group, and a cycloalkoxycarbonyl group, more preferred are a straight chain or branched alkyl group, a cycloalkyl group, and an aromatic group, and particularly preferred are a straight chain or branched alkyl group, and a cycloalkyl group.

These groups may have a substituent. Examples of the substituent include substituent T described below.

Preferable examples of the alkyl group include methyl, butyl, hexyl, 2-ethylhexyl, t-butyl, and trifluoromethyl groups.

Preferable examples of the aromatic group include phenyl, pentafluorophenyl, 1-naphthyl, and 2-thienyl.

In formulae (a-1) to (a-5), groups having the following structures are enumerated including the case where Rd's which are adjacent to each other are combined to form a ring.

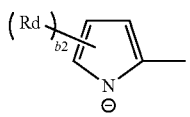
(a-1)

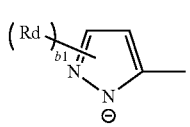
(a-2)

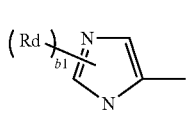
(a-3)

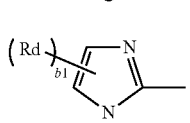
(a-4)

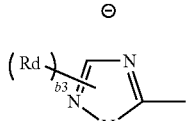
(a-5)

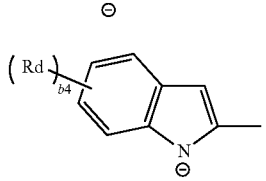
(a-1a)

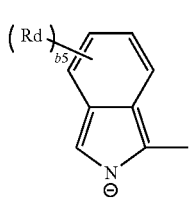
(a-1b)

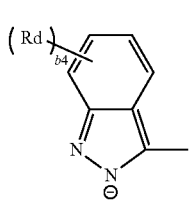
(a-2a)

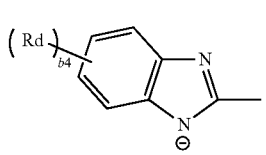
(a-4a)

In the above formulas, Rd and b1 to b3 have the same meaning as those in formulas (a-1) to (a-5), respectively, and the preferable ranges thereof are also the same. b4 represents an integer of 0 to 4. b5 represents an integer of 0 to 5. In formulae (a-1a) and (a-1b), Rd may bind to not only a benzene ring, but also a pyrrol ring.

In formula (A), l1 is preferably 1.

In the present invention, a ligand (compound) represented by formula (A) is preferably the ligand (compound) in which l 1 is 1 and each of $Ar^1$ and $Ar^2$ is a heteroamomatic group having an anion, and the ligand (compound) in which $Ar^1$ is a nitrogen-containing aromatic ring group having a lone electron pair and l 1 is 0, and is more preferably a compound in which l 1 is 1 and each of $Ar^1$ and $Ar^2$ is a heteroamomatic group having an anion. In this case, it is particularly preferably that each of $Ar^1$ and $Ar^2$ is one represented by formula (a-2).

The ligand (compound) represented by formula (A) is preferably a ligand (compound) represented by formula (A-3), more preferably a ligand (compound) represented by formula (A-4) or (A-5), and further preferably a ligand (compound) represented by formula (A-5) from the viewpoint of heat resistance.

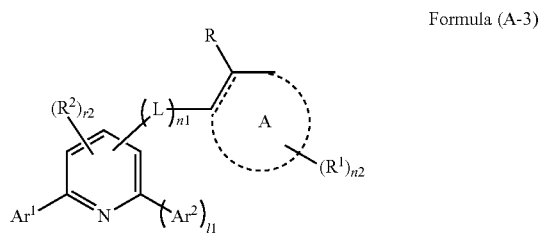

Formula (A-3)

In formula (a-3), $Ar^1$, $Ar^2$, R, $R^1$, $R^2$, L, l1, n1, n2, r2, and the ring A have the same meaning as those in formulas (A) and (A-1), respectively.

Formula (A-4)

In formula (a-4), R, $R^1$, n1, and n2 have the same meaning as those in formula (A), respectively. The ring A has the same meaning as that in formulas (A) and (A-1).

Rd represents an alkyl group, a cycloalkyl group, an alkoxy group, a cycloalkoxy group, an alkylthio group, a cycloalkylthio group, an amino group, an alkylamino group, a cycloalkylamino group, an arylamino group, a heterocyclic amino group, a halogen atom, a cyano group, an alkoxycarbonyl group, a cycloalkoxycarbonyl group, or an aromatic group.

b1 represents an integer of 0 to 2. When b1 is 2, two Rd's may be bonded to each other to form a ring.

Formula (A-5)

In formula (a-5), R, $R^1$, n1, and n2 have the same meaning as those in formula (A), respectively. The ring A has the same meaning as that in formulas (A) and (A-1). Rd and b1 have the same meaning as those in formula (A-4), respectively.

The ligand (compound) represented by formula (A-4) is obtained by anionizing a compound represented by formula (A-4').

Formula (A-4')

In formula (A-4'), R, $R^1$, Rd, L, b1, n1, n2, and the ring A have the same meaning as those in formula (A-3), respectively.

Further, the ligand (compound) represented by formula (A-5) is obtained by anionizing a compound represented by formula (A-5').

Formula (A-5')

In formula (A-5'), R, $R^1$, Rd, L, b1, n1, n2, and the ring A have the same meaning as those in formula (A-3), respectively.

The ligand LD is preferably one that has no acidic group in the compound.

Specific examples of the ligand (compound) represented by formula (A) are shown below, but the present invention is not limited to these. In a case where in the following structures, they are incorporated as a ligand of a metal complex dye, the nitrogen atom-NH-portion of the nitrogen-containing hetero ring shows the —N_-portion.

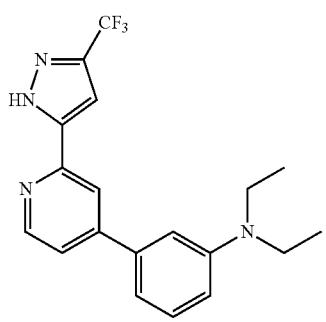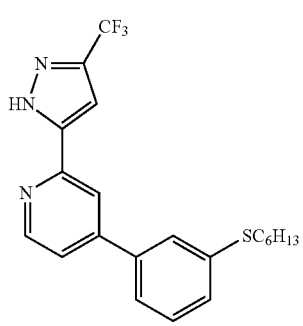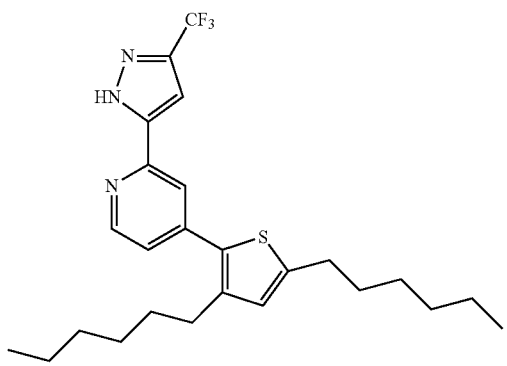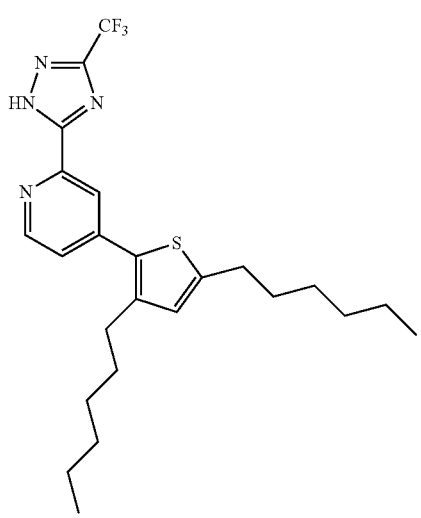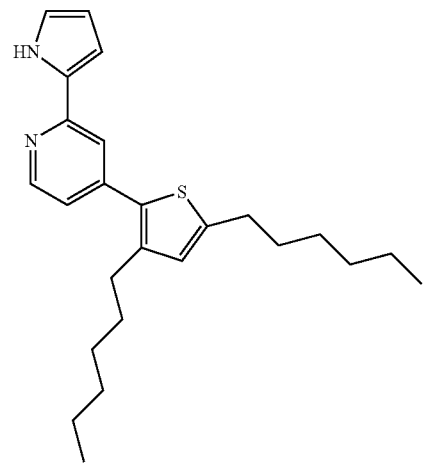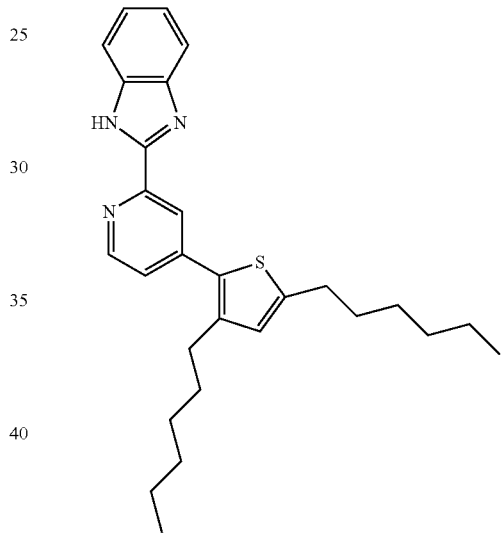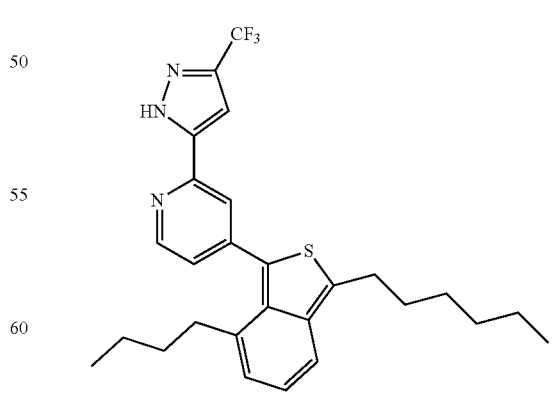

31
-continued
32
-continued
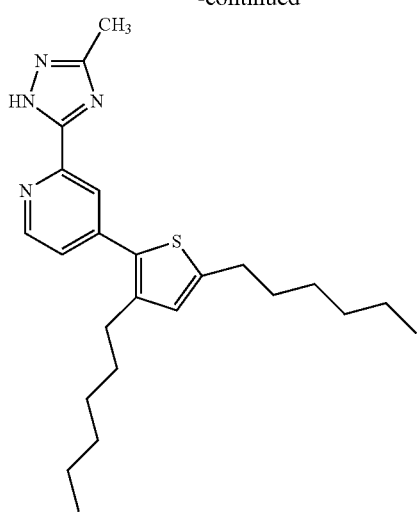
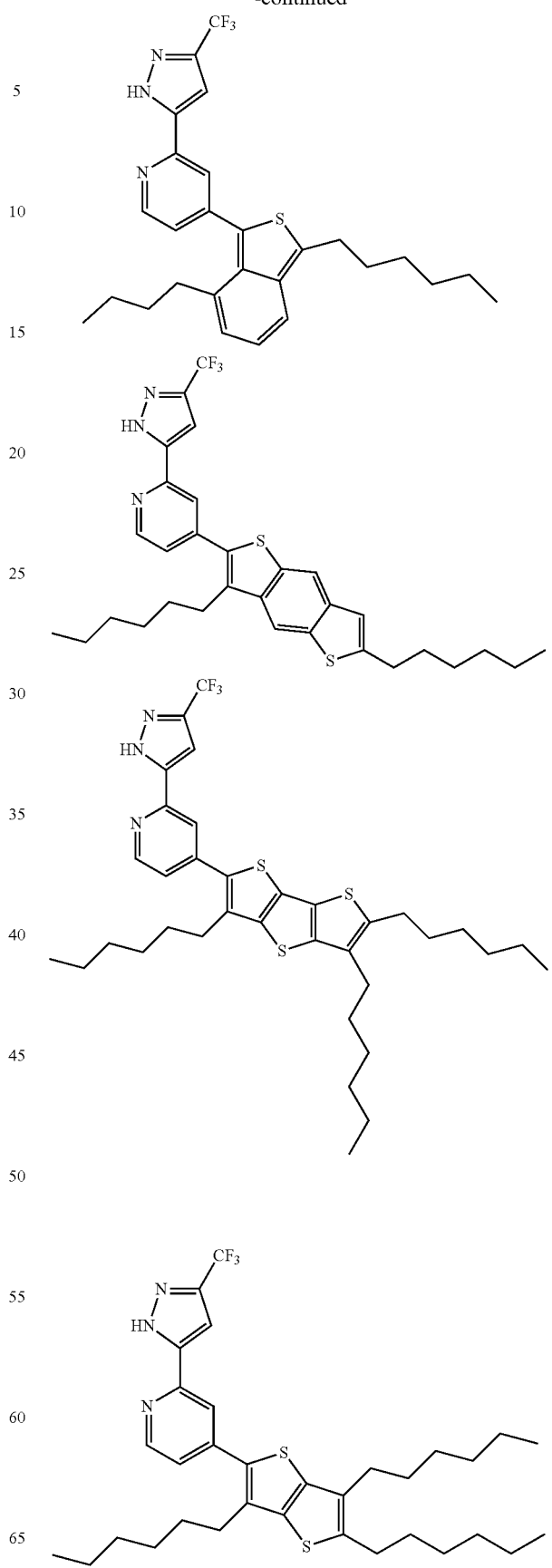

33
-continued
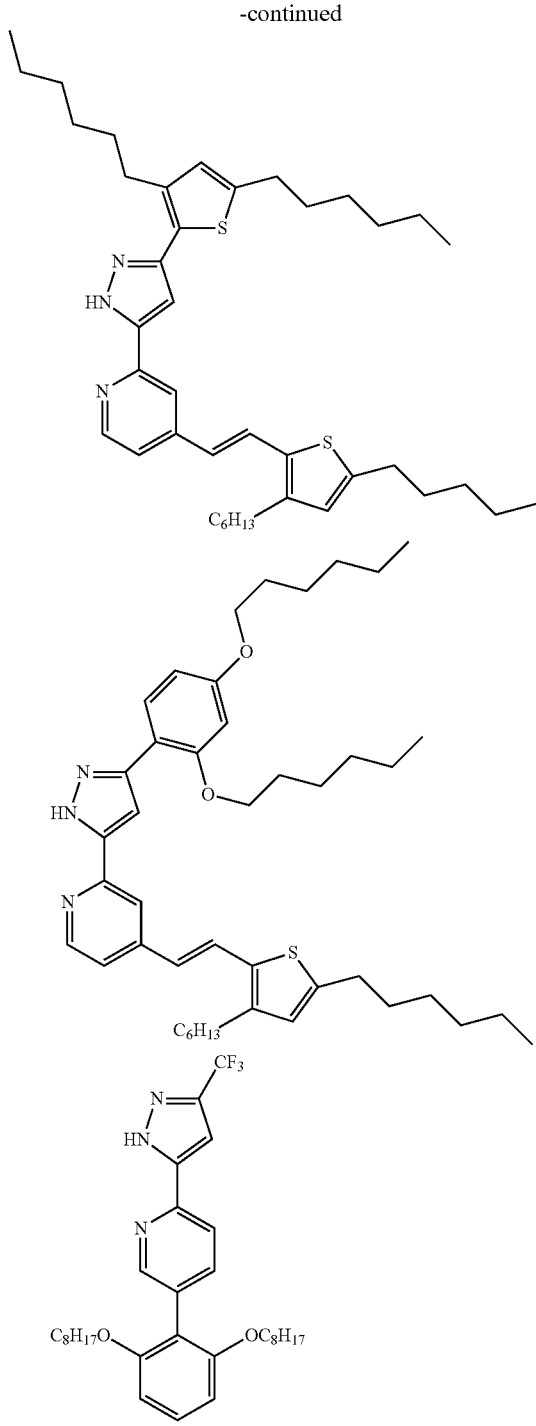
34
-continued
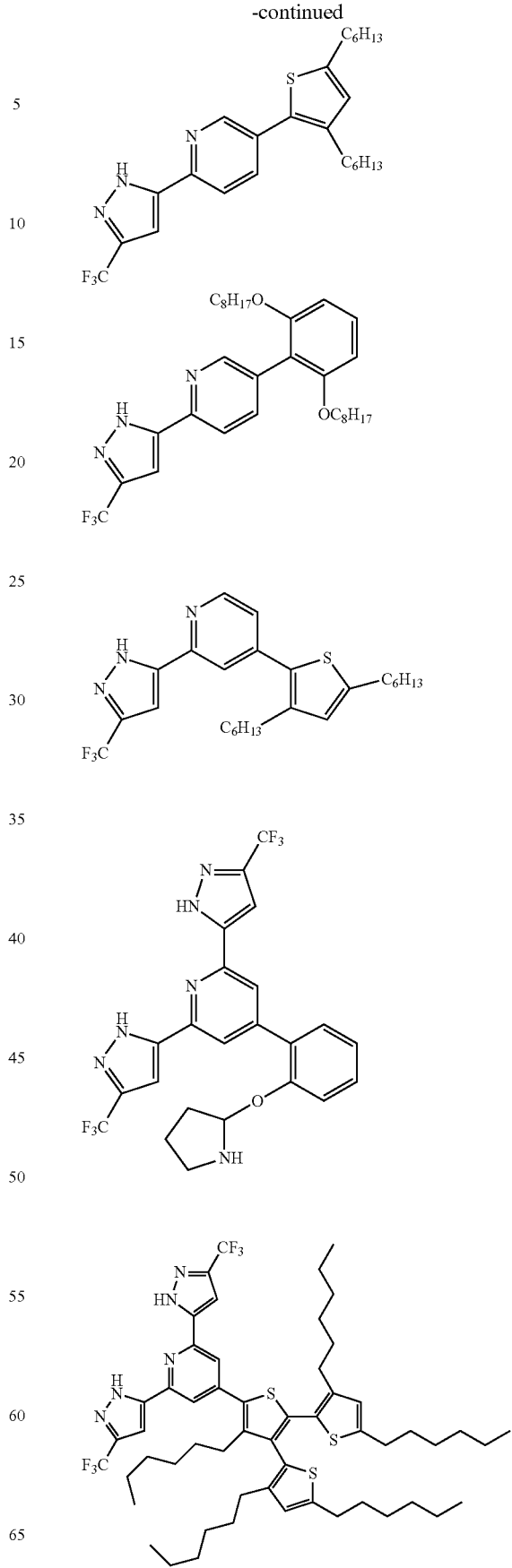

-continued
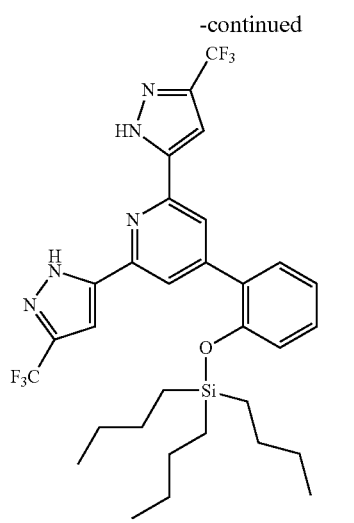
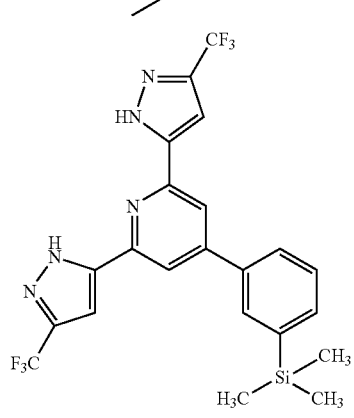
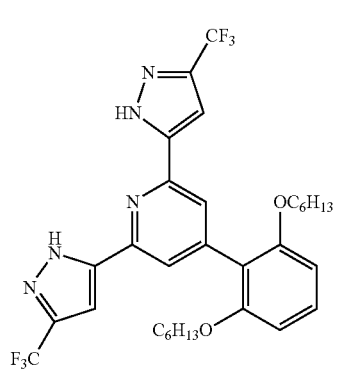
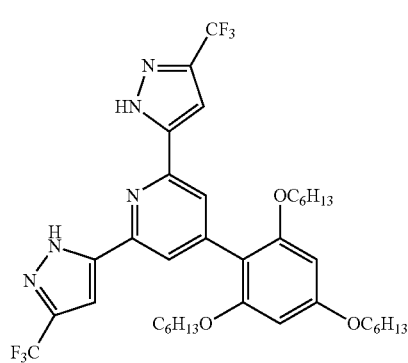
-continued
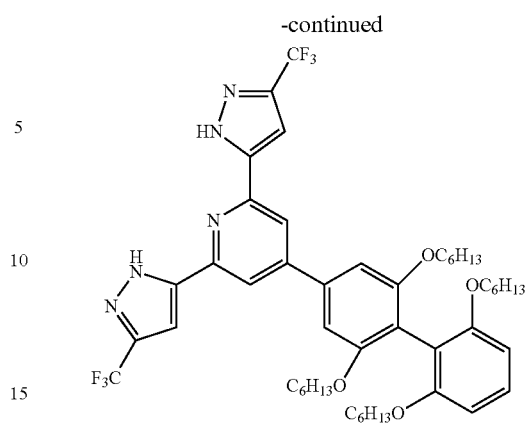
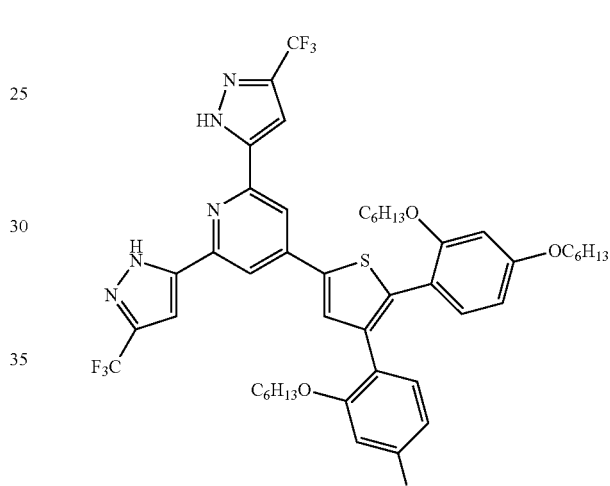
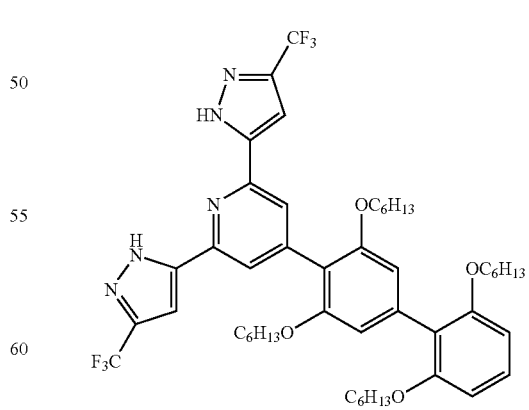

37
-continued
38
-continued
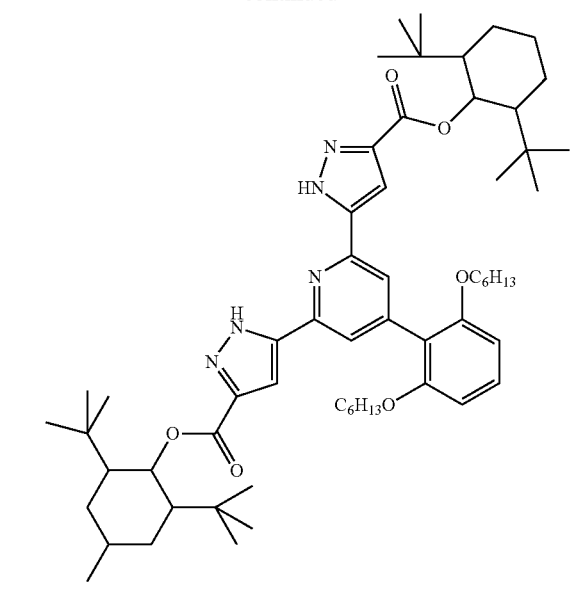
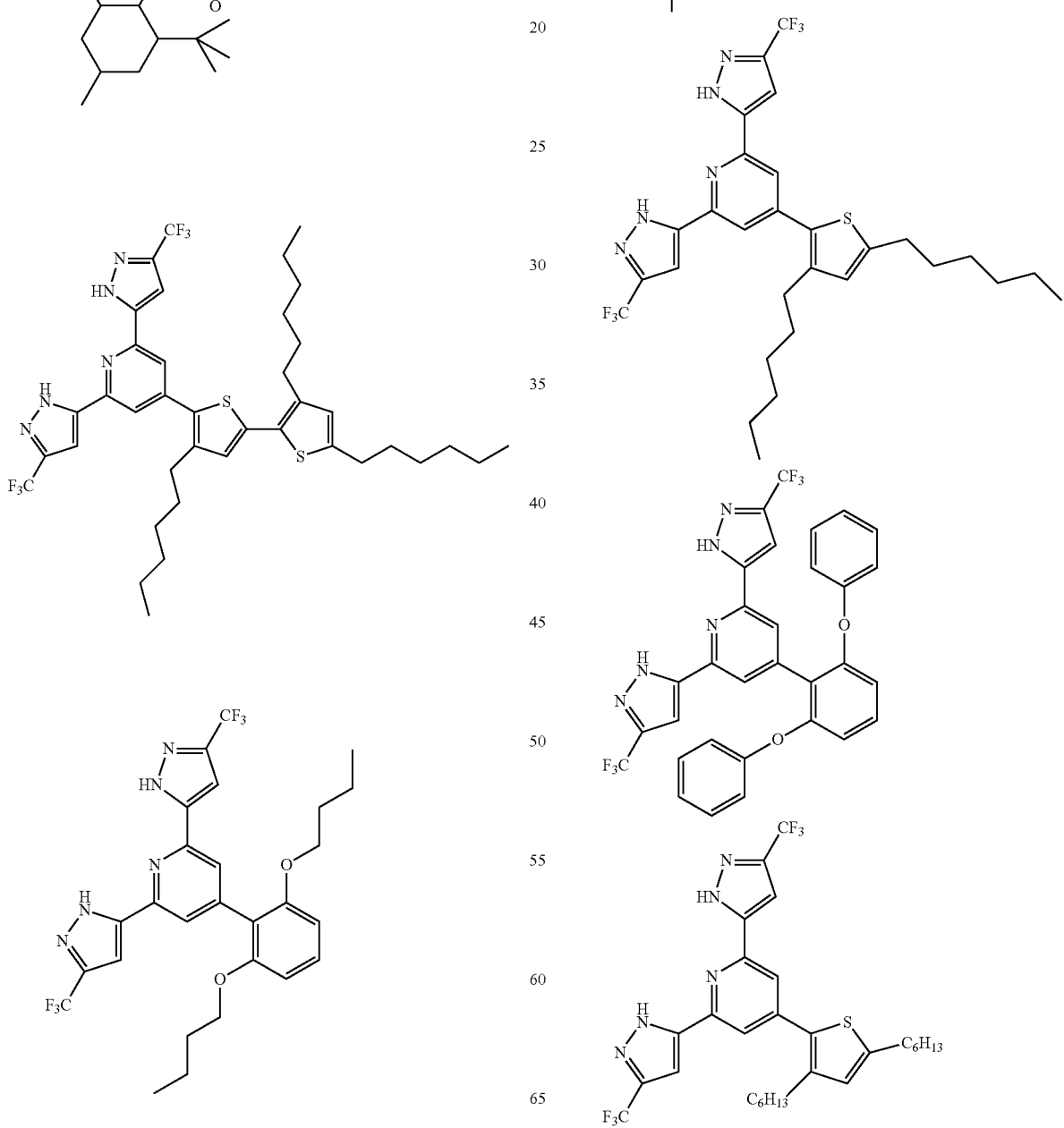

-continued

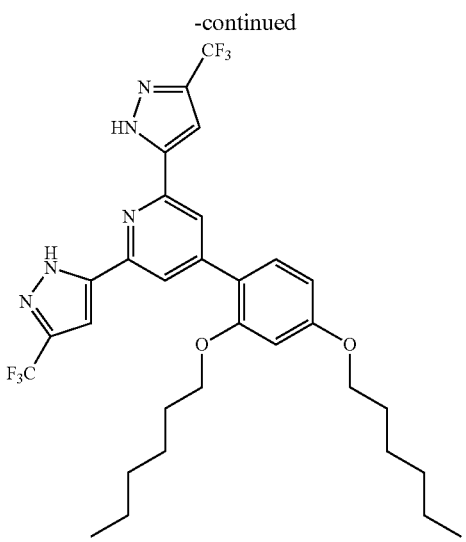

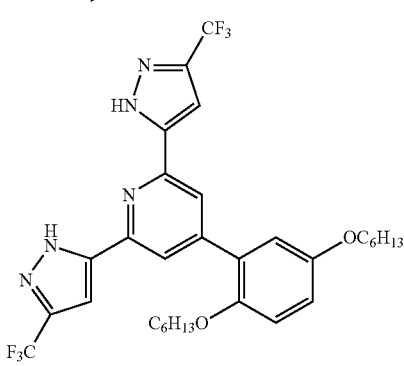

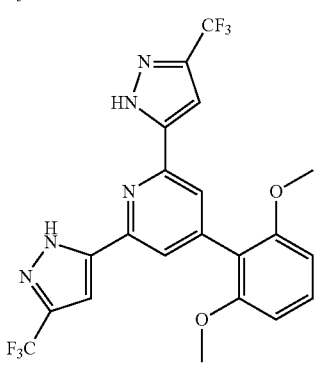

The ligand LD represented by formula (A) can be readily synthesized by methods described in US 2010/0258175 A1, Japanese Patent No. 4298799, and Angew. Chem. Int. Ed., 2011, 50, 2054-2058, methods described in references cited in the literatures, or methods according to these methods.

—Ligand LA—

In the present invention, the ligand LA is categorized as an acceptor ligand, and is represented by formula (B).

Formula (B)

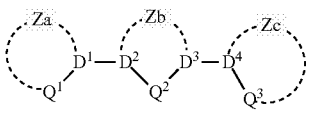

In formula (B), Za, Zb and Zc each independently represent a group of atoms for forming a 5- or 6-membered ring, in which at least one of the rings formed by Za, Zb and Zc has an acidic group.

$Q^1$ to $Q^3$ each independently represent a nitrogen atom having a lone electron pair, a nitrogen atom having an anion, or a carbon atom having an anion.

$D^1$ to $D^4$ each independently represent a carbon atom or a nitrogen atom.

The rings formed by Za, Zb and Zc are a 5-membered ring or a 6-membered ring. The formed ring may be of any form, as long as it is able to coordinate to a metal atom M via $Q^1$ to $Q^3$.

In the above, a bond between $Q^1$-$D^1$, a bond between $D^2$-$Q^2$, a bond between $D^3$-$Q^2$, and a bond between $D^4$-$Q^3$ are indicated by "-" for the sake of convenience. The bonds between these atoms indicate that these atoms bind to one another, and the bond may be a single bond (—) or a double bond (═).

The rings formed by Za, Zb and Zc may be either an aromatic ring or a ring other than an aromatic ring (examples thereof include an aliphatic saturated ring or an unsaturated ring other than an aromatic ring, and a non-aromatic hetero ring), and an aromatic ring is preferred. The aromatic ring includes an aromatic carbocyclic ring and an aromatic hetero ring (heteroaryl ring). Of these, an aromatic hetero ring is preferred.

In a case of the aromatic carbocyclic ring, a 6-membered ring is preferred, while in a case of the aromatic hetero ring, a 5- or 6-membered ring is preferred.

The rings formed by Za, Zb and Zc may either be non-substituted or have a substituent, and at least two of the rings formed by Za, Zb and Zc have an acidic group. Examples of the substituent include substituent T described below.

Further, the rings formed by Za, Zb and Zc may be a single ring, or may be ring-fused with an aliphatic saturated or unsaturated ring or an aromatic ring, or an aromatic or non-aromatic hetero ring.

In a case where any of $Q^1$ to $Q^3$ is a carbon atom having an anion, as for the ring in which the carbon atom having an anion is a ring-constituent atom, an aliphatic ring is preferred, and an aromatic carbocyclic ring is preferred.

The foregoing ring includes a cyclopentadiene ring, a benzene ring, and a naphthalene ring, and a benzene ring is preferred.

Further, the ring includes a hetero ring other than an aliphatic ring and also other than a nitrogen-containing hetero ring, and examples thereof include a furan ring, a benzo[b]furan ring, a thiophene ring, a benzo[b]thiophene ring, a naphthothiophene ring, a thianthrathene ring, a tetrahydrofuran ring, a tetrahydropyran ring, and a 4H-pyran ring.

In a case where any of $Q^1$ to $Q^3$ is a nitrogen atom having a lone electron pair, or a nitrogen anion, the nitrogen-containing hetero ring which is formed together with the nitrogen atom having a lone electron pair, or the nitrogen anion as a ring-constituent atom may be either a ring which has only a nitrogen atom as a ring-constituent atom or a ring which contains an oxygen atom, a sulfur atom (for example, —S—, SO—, —$SO_2$—, a phosphorus atom, a silicon atom, a selenium atom together with the nitrogen atom. Further, the ring to be formed may be either an aromatic ring or a non-aromatic hetero ring, and a hetero aromatic ring is preferred.

Further, in a case where any of $Q^1$ to $Q^3$ is a nitrogen atom having a lone electron pair, the ring to be formed is preferably a 6-membered hetero aromatic ring. In a case where any of $Q^1$ to $Q^3$ is a nitrogen anion, the ring to be formed is preferably a 5-membered hetero aromatic ring. In a case where any of $Q^1$ to $Q^3$ is a nitrogen anion, when the nitrogen anion is incorporated into a metal complex dye as a ligand, the nitrogen anion is incorporated as —N⁻— derived from —NH—.

Examples of the nitrogen-containing heteroaromatic ring include a pyrrole ring, a pyrazole ring, an imidazole ring, a triazole ring, a tetrazole ring, an oxazole ring, a thiazole ring, an isoxazole ring, an isothiazole ring, a furazan ring, a pyridine ring, a pyridazine ring, a pyrimidine ring, a pyrazine ring, a triazine ring, an indole ring, a benzopyrrol ring, an isoindole ring, a benzimidazole ring, a benzotriazole ring, a benzoxazole ring, a benzothiazole ring, a quinoline ring, an isoquinoline ring, a phthalazine ring, a cinnoline ring, a quinazoline ring, a phenanthridine ring, a phenanthroline ring, a quinoxaline ring, a naphthyridine ring, a purine ring, a pteridine ring, and a β-carboline ring.

Examples of the nitrogen-containing hetero ring other than the heteroaromatic ring includes a pyrrolidine ring, a pyrroline ring, a pyrazoline ring, a pyrazoline ring, an imodazolidine ring, an imodazoline ring, a piperazine ring, a piperidine ring, a morpholine ring, a phenothiazine ring, a phenoxazine ring, a 1,4-dihydropyridine ring, a tetradehydromorpholine ring, or a tetradehydrothiomorpholine ring.

The nitrogen-containing hetero ring (including a heteroaromatic ring) may coordinate to a metal atom M via an anion derived from a ring-constituent carbon atom thereof, without coordinating thereto via a nitrogen atom or an anion thereof.

In a case where any of $Q^1$ to $Q^3$ is a nitrogen atom having a lone electron pair or a nitrogen anion, the nitrogen-containing hetero ring which is formed together with the nitrogen atom having the lone electron pair or the nitrogen anion as a ring-constituent atom is preferably a benzimidazole ring, a benzothiazole ring, a pyrrole ring, a pyrazole ring, a triazole ring, a pyridine ring, a pyrimidine ring, a pyridazine ring, a pyrazine ring, or a quinoline ring, more preferably a benzothiazole ring, a benzimidazole ring, a quinoline ring, a pyrazole ring, or a pyridine ring, still more preferably a pyridine ring, or a quinoline ring, and most preferably a pyridine ring.

At least one of the rings formed by Za, Zb and Zc has an acidic group. The number of acidic groups is preferably from 2 to 6, more preferably from 2 to 4, still more preferably from 2 to 3, and most preferably 3.

The acidic group has the same meaning as described in the above and a preferable range thereof is also the same. The acidic group may be substituted directly at the ring formed by any of Za to Zc, or may be a group which binds to the ring via a linking group.

In a case where the ring formed by any of Za to Zc is a pyridine ring, the pyridine ring having an acidic group at the p-position with respect to the nitrogen atom thereof is preferred.

l2 is preferably 1.

$D^1$ to $D^4$ each represent a carbon atom or a nitrogen atom, and each of $D^2$ and $D^3$ is preferably a carbon atom. In a case where each of $D^2$ and $D^3$ is a carbon atom, $D^1$ and/or $D^4$ are preferably a nitrogen atom. In the present invention, it is particularly preferred that all of $D^1$ to $D^4$ are a carbon atom.

In a case where $D^1$ and/or $D^4$ is or are a nitrogen atom, the ring to be formed by Za and $Q^1$, and/or Zc and $Q^4$ is preferably a pyrazole ring, a triazole ring, or a pyridine ring.

The ligand LA represented by formula (B) is preferably a compound represented by any one of formulas (B1) to (B8).

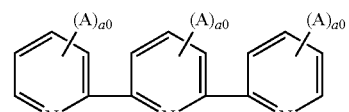

Formula (B1)

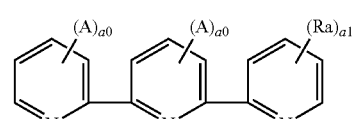

Formula (B2)

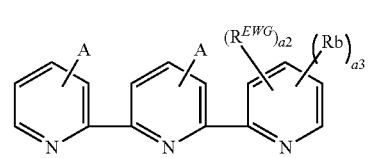

Formula (B3)

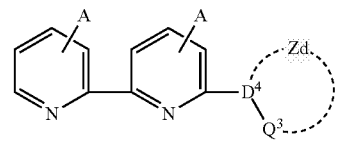

Formula (B4)

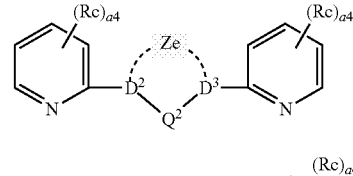

Formula (B5)

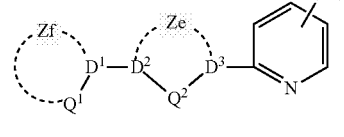

Formula (B6)

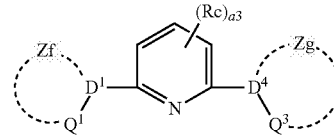

Formula (B7)

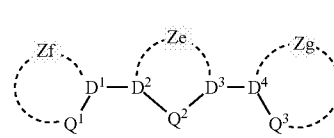

Formula (B8)

In formulas (B1) to (B8), $Q^1$ to $Q^3$ and $D^1$ to $D^4$ have the same meaning as those in formula (B), respectively;

Zd represent a group of atom for forming a benzene ring, a naphthalene ring, an anthracene ring, a phenanthrene ring, a pyrene ring, a perylene ring, a pyrrole ring, an indole ring, an imidazole ring, a benzimidazole ring, a pyrazole ring, a pyrazine ring, a pyrimidine ring, a benzopyrimidine ring, a pyridazine ring, a benzopyridazine ring, a triazole ring, a benzotriazole ring, a tetrazole ring, an indazole ring, a triazine ring, a purine ring, a quinoline ring, an isoquinoline ring, a quinazoline ring, a thiazole ring, a benzothiazole ring, an isothiazole ring, an oxazole ring, an isoxazole ring, a benzoxazole ring, a furan ring, a benzo[b]furan ring, a thiophene ring, a benzo[b]thiophene ring, a pyrrolidine ring, a piperidine ring, a morpholine ring, a piperazine ring, a tetrahydrofuran ring, a tetrahydropyran ring, a 4H-pyran ring, a 1,4-dihydropyridine ring, a tetradehydromorpholine ring, or a tetradehydrothiomorpholine ring.

The ring formed by Zd is preferably an aromatic ring (an aromatic carbon ring or a heteroaromatic ring). The aromatic ring is preferably a benzimidazole ring, a benzothiazole ring, a thiophene ring, a pyrrole ring, a pyrazole ring, a triazole ring, a pyrimidine ring, a pyridazine ring, a pyrazine ring, a quinoline ring, or a benzene ring; more preferably a benzothiazole ring, a benzimidazole ring, a quinoline ring, a pyrazole ring, a triazole ring, or a benzene ring; particularly preferably a benzothiazole ring, a benzimidazole ring, a triazole ring, or a triazine ring; and most preferably a quinoline ring.

Ze to Zg represent a group of atom for forming a 5- or 6-membered ring other than a pyridine ring.

Preferable ranges of Zf and Zg are the same as that of Zd.

The ring formed by Ze is preferably an aromatic ring, and as an aromatic ring, preferred is a benzene ring, a naphthalene ring, a thiophene ring, a pyrrol ring, a pyrazole ring, a triazole ring, a pyrazine ring, or a triazine ring, especially preferred is a pyrimidine ring, a pyrazine ring, a pyrazole ring, a triazole ring, or a benzene ring, particularly preferred is a triazole ring or a benzene ring, and most preferred is a triazole ring.

The ring formed by Zd to Zg may have a substituent. Examples of the substituent include substituent T described below.

A represents an acidic group.

The acidic group has the same meaning as described above, and a preferable range thereof is also the same.

Ra represents an aryl group, a heteroaryl group, an alkyl group, a cycloalkyl group, an alkoxy group, or a cycloalkoxy group.

Ra is preferably an aryl group, a heteroaryl group, an alkyl group, or a cycloalkyl group, more preferably an aryl group having the substituent R, or a heteroaryl group having the substituent R, and particularly preferably a heteroaryl group having the substituent R. It is presumed that association of dyes is suppressed due to such a bulky Ra, and as a result, electron injunction into semiconductor fine-particles progresses efficiently and short-circuit current density (Jsc) is improved.

The number of carbon atoms of an aryl group is preferably from 6 to 20, more preferably from 6 to 16, particularly preferably from 6 to 14, and most preferably from 6 to 10, and a benzene ring is most preferred.

The number of atoms other than a hydrogen atom of the heteroaryl group is preferably from 5 to 30, more preferably from 5 to 25, still more preferably from 5 to 20, and particularly preferably from 5 to 12, and a thiophene ring is most preferred.

The alkyl group contains a tertiary or quaternary carbon atom, and from the viewpoint of suppression of association due to bulkiness, preferably contains a quaternary carbon atom. The number of carbon atoms is preferably from 4 to 30, more preferably from 6 to 28, still more preferably from 6 to 26, and particularly preferably from 6 to 20.

The number of carbon atoms of the cycloalkyl group is preferably from 3 to 30, more preferably from 5 to 28, still more preferably from 6 to 26, and particularly preferably from 6 to 20.

Examples of the alkyl group and the cycloalkyl group include t-butyl, i-pentyl, isohexyl, isooctyl, 2-ethylhexyl, isodecyl, isodecyl, isooctacosyl, cyclopropyl, cyclopentyl, cyclohexyl, and adamantyl.

The alkoxy group includes a tertiary or quaternary carbon atom, or a secondary or tertiary carbon atom which binds directly to the oxygen atom of the alkoxy group, and from the viewpoint of suppression of association due to bulkiness, preferred are the case of containing a quaternary carbon atom and the case of containing a tertiary carbon atom which binds directly to the oxygen atom of the alkoxy group. The number carbon atoms of the alkoxy group is preferably from 3 to 30, more preferably from 4 to 30, still more preferably from 4 to 26, and particularly preferably from 4 to 20.

The number carbon atoms of the cycloalkoxy group is preferably from 3 to 30, more preferably from 5 to 28, still more preferably from 6 to 26, and particularly preferably from 6 to 20.

Examples of the alkoxy group and the cycloalkoxy group include i-propoxy, i-butoxy, t-butoxy, i-pentoxy, i-octyloxy, 2-ethylhexyloxy, isodecyloxy, isohexadecyloxy, isooctacosyloxy, cyclopropyloxy, cyclopentyloxy, and cyclohexyloxy.

Rb and Rc represent a substituent. Examples of the substituent include substituent T described below.

$R^{EWG}$ represents an electron-withdrawing group.

The electron-withdrawing group is further described in below.

Examples of the electron-withdrawing group include a substituent having the −I effect or the −M effect.

In general, an electron-withdrawing group attenuates the electron density at a particular position of a molecule. The electron-withdrawing property or electron-donating property cannot be explained only by the difference in the electronegativity. That is, since an inductive effect, a mesomeric effect and the like work together in a composite manner, the manifestation of the electron-withdrawing property or the electron-donating property can vary with the aromaticity, presence of a conjugated system, or a topological positional relationship. As an experimental rule for quantitatively evaluating and predicting these effects on the basis of the acid dissociation constant of para- and meta-substituted benzoic acid, there is known Hammett's rule. In the case of the inductive effect, the electron-withdrawing effect is referred to as the −I effect, while the electron-donating effect is referred to as the +I effect, and an atom having higher electronegativity than carbon exhibits the −I effect. Furthermore, an anion exhibits the +I effect, while a cation exhibits the −I effect. In the case of the mesomeric effect, the electron-withdrawing effect is referred to as the −M effect, while the electron-donating effect is referred to as the +M effect. Examples of the electron-withdrawing group are shown below.

Inductive Effect (−I Effect)

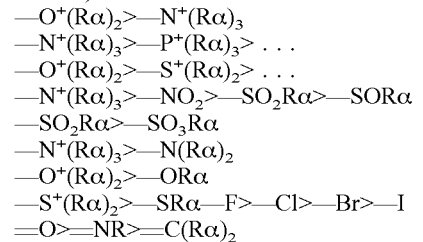

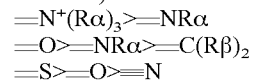

In the above, Rα represents a substituent, and is representatively an alkyl group. Rβ represents a hydrogen atom or a substituent, and the substituent is representatively an alkyl group.

The group may bind directly, or may bind via a conjugated system, for example, an aromatic ring (an aromatic carbon ring, an aromatic hetero ring), an ethynyl group, or an ethenyl group.

Examples of the case of binding via an aromatic ring include a halogenated phenyl group, a cyanopheny group, and a trifluoromethylphenyl group.

Further, of the substituent T described below, groups with σp of 0 or more according to Hammett's rule are enumerated as a specific group. Electron-attracting groups other than an acidic group are preferred, and preferable examples thereof include a fluoroalkyl group (for example, a perfluoroalkyl group, such as trifluoromethyl) and a halogen atom. Especially, a cyano group is preferred.

a0 represents an integer of 0 to 2. Herein, at least one of a0's in each of formulas (B1) and (B2) is 1 or 2;

a1 represents an integer of 1 or 2.

a2 represents an integer of 1 to 4, a3 represents an integer of 0 to 3, and a4 represents an integer of 0 to 4. The sum of a2 and a3 is an integer of 1 to 4.

In each of a1 to a4, in a case where these are an integer of 2 or more, Ra's, Rb's, $R^{EWG}$'s, or Rc's may bind to one another to form a ring. The ring to be formed is preferably an aromatic ring.

The ligands represented by any of formulas (B5) to (B8) each have at least one (1) acidic group, preferably two (2) or three (3) acidic groups.

Of the ligands represented by any of formulae (B1) to (B8), the ligand represented by formula (B1) is preferred, from the viewpoint of adsorption power to the semiconductor fine-particle surface.

The ligand represented by formula (B2) is preferred, from the viewpoint of short-circuit current density (Jsc).

The ligand represented by formula (B3) or (B4) is preferred, from the viewpoint of solution stability of the resultant metal complex dye.

The compounds represented by any of formulae (B5) to (B8) are preferred, from the viewpoint of adsorption rate from the semiconductor fine-particle surface.

Specific examples of the ligand represented by formula (B) are shown below, but the present invention is not limited to these.

Compound represented by Formula (B1)

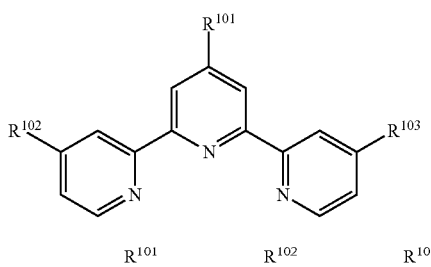

| | $R^{101}$ | $R^{102}$ | $R^{103}$ |
|---|---|---|---|
| LA-1-1 | —COOH | —COOH | —COOH |
| LA-1-2 | —COOH | —COOH | —H |
| LA-1-3 | —PO$_3$H$_2$ | —PO$_3$H$_2$ | —H |
| LA-1-4 | —H | —PO$_3$H$_2$ | —H |
| LA-1-5 | —H | —SO$_3$H | —H |
| LA-1-6 | —H | —CO$_2$H | —H |

Compound represented by Formula (B2)

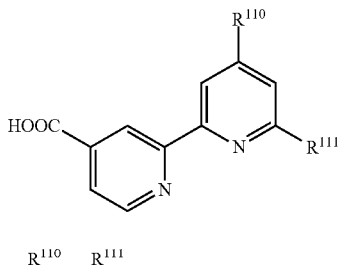

| | $R^{110}$ | $R^{111}$ |
|---|---|---|
| LA-2-1 | —COOH | 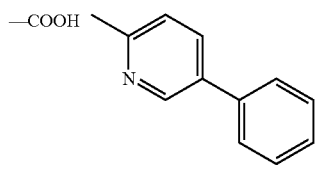 |
| LA-2-2 | —COOH | 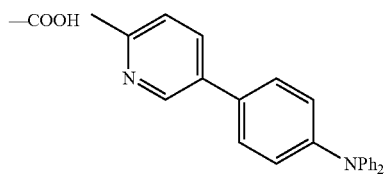 |
| LA-2-3 | —COOH | 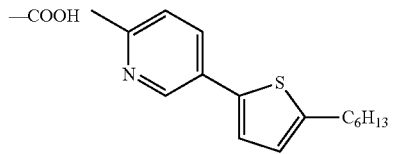 |
| LA-2-4 | —COOH | 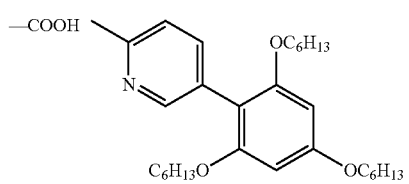 |
| LA-2-5 | —COOH | 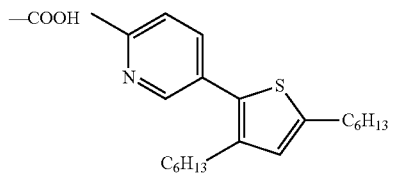 |
| LA-2-6 | —COOH | 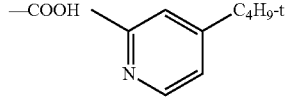 |
| LA-2-7 | —OH | 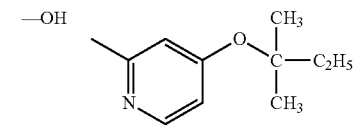 |
| LA-2-8 | —COOH | 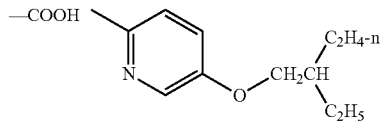 |

| Compound represented by Formula (B2) | | |
|---|---|---|
| | R¹¹⁰ R¹¹¹ | |
| LA-2-9 | —COOH | (6-methylpyridin-3-yl)-thiophene with two 2-hexyloxy-4-hexyloxyphenyl groups |
| LA-2-10 | —COOH | 2-methylpyridin-4-yl-(2,6-bis(hexyloxy)phenyl) |
| LA-2-11 | —COOH | 6-methylpyridin-3-yl-(2,4-bis(hexyloxy)phenyl) |

| Compound represented by Formula (B3) | |
|---|---|
| | R¹¹² |
| LA-3-1 | 6-methylpyridin-3-yl, Br |
| LA-3-2 | 6-methylpyridin-3-yl, CN |
| LA-3-3 | 6-methylpyridin-3-yl, C(O)OCH₃ |
| LA-3-4 | 2-methylpyridin-5-yl, CF₃ |
| LA-3-5 | 2-methylpyridin-4-yl, CF₃ |
| LA-3-6 | 6-methylpyridin-3-yl, I |
| LA-3-7 | 6-methylpyridin-3-yl, F |
| LA-3-8 | 2-methylpyridin-4-yl, F |
| LA-3-9 | 2-methyl-3,5-difluoropyridinyl |
| LA-3-10 | 6-methylpyridin-3-yl-(2,4,6-trifluorophenyl) |
| LA-3-11 | 6-methylpyridin-2-yl, CN |

| Compound represented by Formula (B3) |
|---|

![structure: HOOC-pyridine-pyridine-COOH with R^112]

| | $R^{112}$ |
|---|---|
| LA-3-12 | 2-methyl-5-nitropyridin-6-yl |
| LA-3-13 | 2-methyl-6-acetylpyridinyl (COCH₃) |
| LA-3-14 | 3,5-dichloro-2-methylpyridinyl |
| LA-3-15 | 5-chloro-2-methylpyridinyl |
| LA-3-16 | 4,6-dibromo-2-methylpyridinyl |
| LA-3-17 | 2-methyl-4-CON(CH₃)₂-pyridinyl |
| LA-3-18 | 2-methyl-4-CONHPh-pyridinyl |
| LA-3-19 | 2-methyl-5-SO₂CH₃-pyridinyl |
| LA-3-20 | 2-methyl-4-CN-pyridinyl |
| LA-3-21 | 2-methyl-4-SO₂N(C₂H₅)₂-pyridinyl |
| LA-3-22 | 2-methyl-4-SO₂NHPh-pyridinyl |
| LA-3-23 | 2-methyl-4-SOPhCH₃-pyridinyl |
| LA-3-24 | 2-methyl-4-COPh-pyridinyl |
| LA-3-25 | 2-methyl-4-Ph-pyridinyl |
| LA-3-26 | 2-methyl-4-(4-pyridyl)pyridinyl |
| LA-3-27 | 2-methyl-4-(styryl)pyridinyl |
| LA-3-28 | 2-methyl-4-(phenylethynyl)pyridinyl |
| LA-3-29 | 2-methyl-4-[2-(5-methylthiophen-2-yl)vinyl]pyridinyl |
| LA-3-30 | 2-methyl-3-CF₃-pyridinyl |

| Compound represented by Formula (B3) | |
|---|---|
| 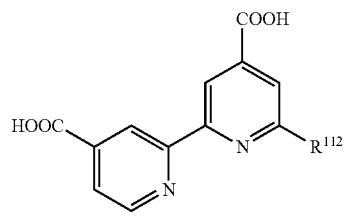 | |
| R¹¹² | |
| LA-3-31 | 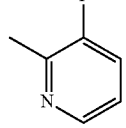 |
| LA-3-32 | 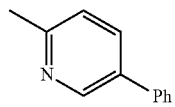 |
| LA-3-33 | 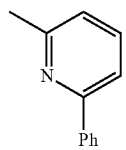 |
| Compound represented by Formula (B4) | |
|---|---|
| 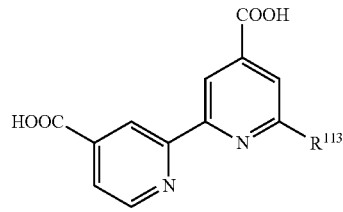 | |
| R¹¹³ | |
| LA-4-1 | 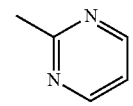 |
| LA-4-2 | 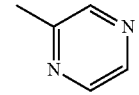 |
| LA-4-3 | 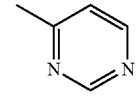 |
| LA-4-4 | 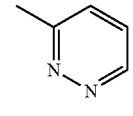 |
| Compound represented by Formula (B4) | |
|---|---|
| 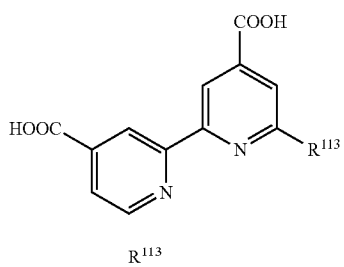 | |
| R¹¹³ | |
| LA-4-5 | 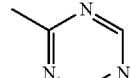 |
| LA-4-6 | 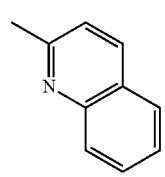 |
| LA-4-7 | 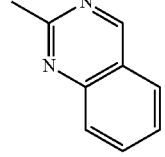 |
| LA-4-8 | 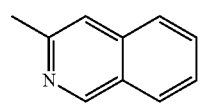 |
| LA-4-9 | 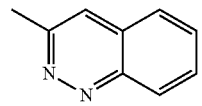 |
| LA-4-10 | 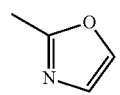 |
| LA-4-11 | 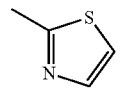 |
| LA-4-12 | 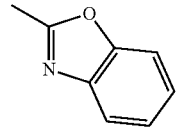 |
| LA-4-13 | 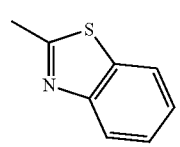 |
| LA-4-14 | 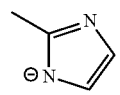 |

-continued

| Compound represented by Formula (B4) |
|---|

[Structure: 2,2'-bipyridine with COOH at 4-position of each ring and R¹¹³ substituent]

| | R¹¹³ |
|---|---|
| LA-4-15 | 2-methylpyrrolide |
| LA-4-16 | methyl-1,2,4-triazolide |
| LA-4-17 | methylpyrazolide |
| LA-4-18 | methyl-1,2,4-triazolide (isomer) |
| LA-4-19 | methyl-CF₃-triazolide |
| LA-4-20 | methyl-CF₃-pyrazolide |
| LA-4-21 | methyl-C₆F₅-pyrazolide |
| LA-4-22 | methyl-tBu-pyrazolide |
| LA-4-23 | methylphenyl anion |
| LA-4-24 | methyl-CF₃-phenyl anion |
| LA-4-25 | methyl-2,4-difluorophenyl anion |

-continued

| Compound represented by Formula (B4) |
|---|

[Structure: 2,2'-bipyridine with COOH at 4-position of each ring and R¹¹³ substituent]

| | R¹¹³ |
|---|---|
| LA-4-26 | methylquinazoline |
| LA-4-27 | methylbenzimidazole |

| Compound represented by Formula (B5) |
|---|

[Structures: Two pyridine-COOH units with R¹¹⁴ substituent]

| | R¹¹⁴ |
|---|---|
| LA-5-1 | 2,5-dimethylpyrrolide |
| LA-5-2 | 3,5-dimethyl-1,2,4-triazolide |
| LA-5-3 | 1,3-dimethylisoindolide |
| LA-5-4 | 3,5-dimethylphenyl anion |
| LA-5-5 | 2,4-dimethylimidazolide |

Compound represented by Formula (B5)
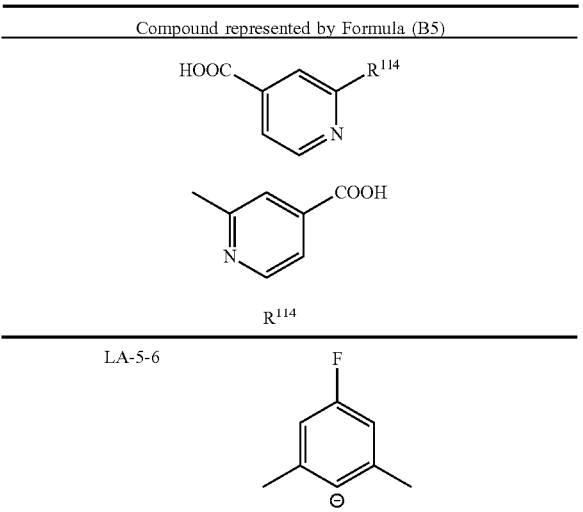
LA-5-6
Compound represented by Formula (B5)
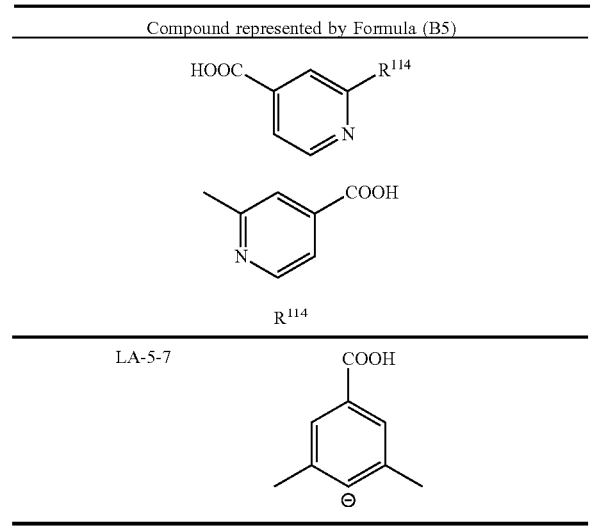
LA-5-7
Compound represented by Formula (B6)
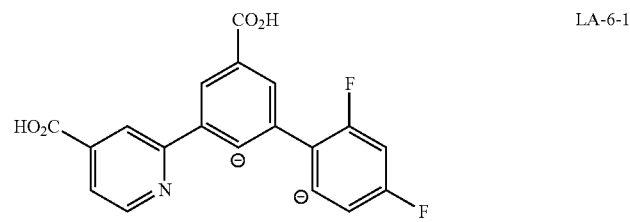
LA-6-1
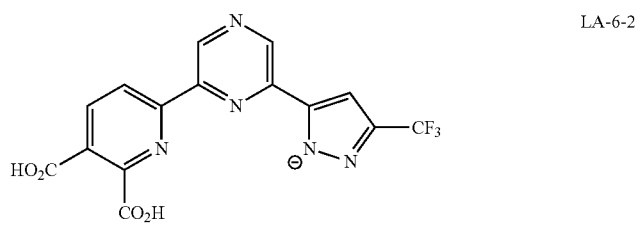
LA-6-2
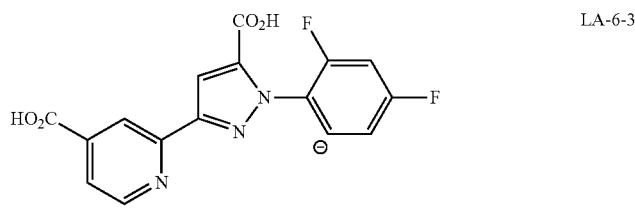
LA-6-3
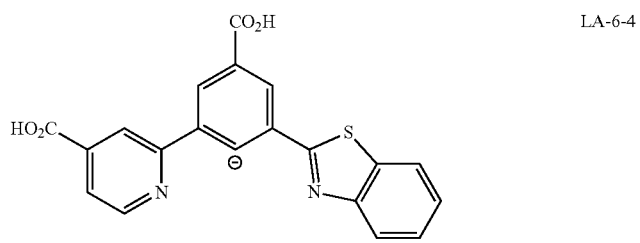
LA-6-4

-continued
| | | | |
|---|---|---|---|
| | 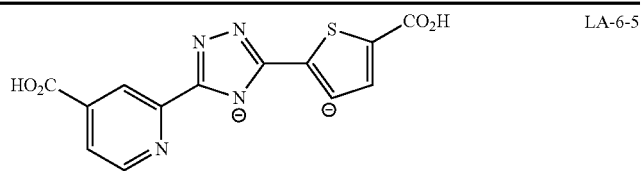 | | LA-6-5 |
| | 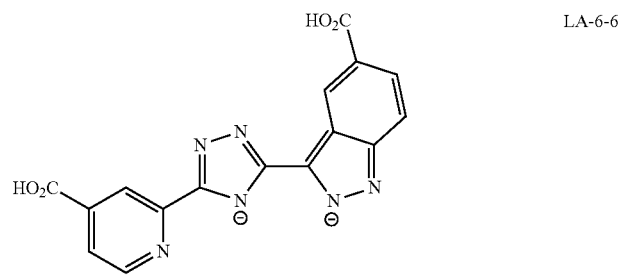 | | LA-6-6 |
| | 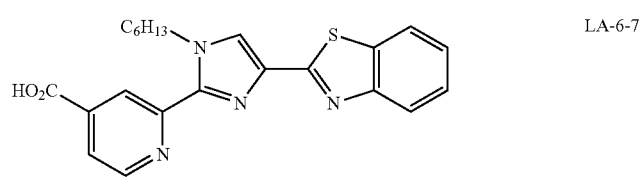 | | LA-6-7 |
| 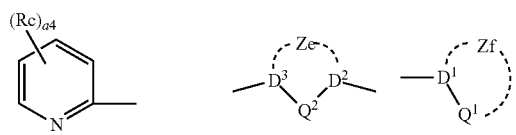 | | | |
| | | | |
|---|---|---|---|
| LA-6-8 | 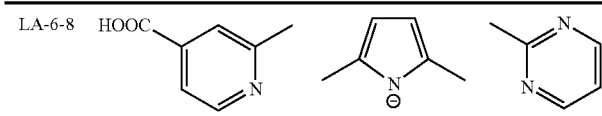 | | |
| LA-6-9 | 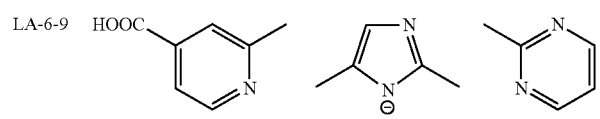 | | |
| LA-6-10 | 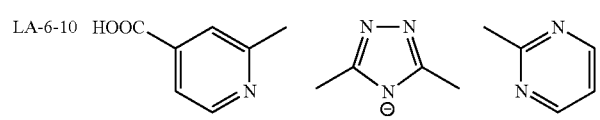 | | |
| LA-6-11 | 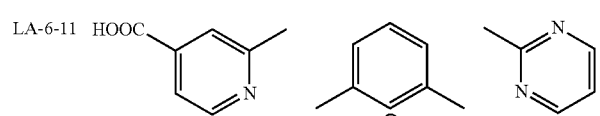 | | |
| LA-6-12 | 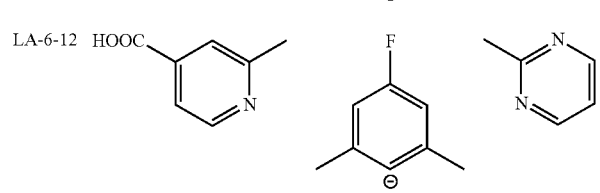 | | |
| LA-6-13 | 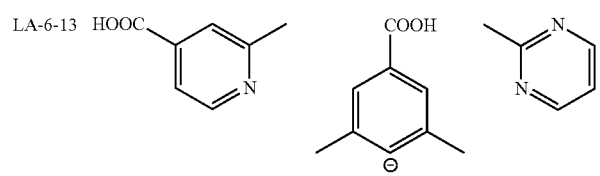 | | |

-continued
LA-6-14 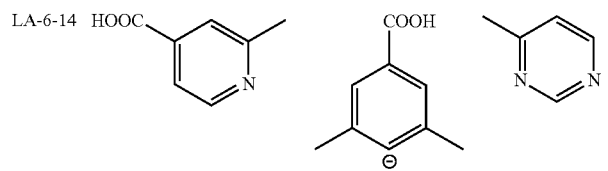
LA-6-15 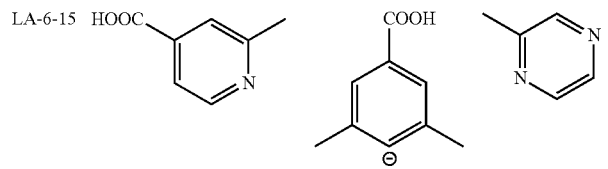
LA-6-16 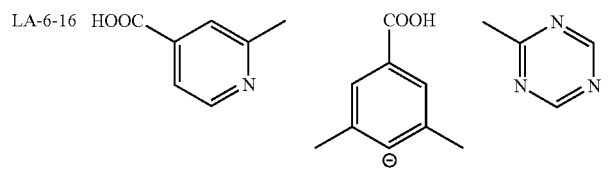
LA-6-17 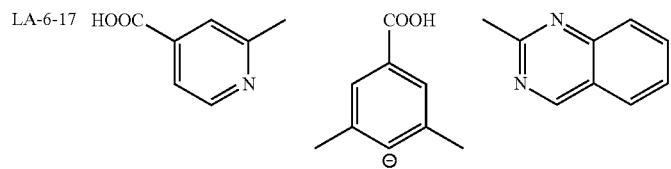
LA-6-18 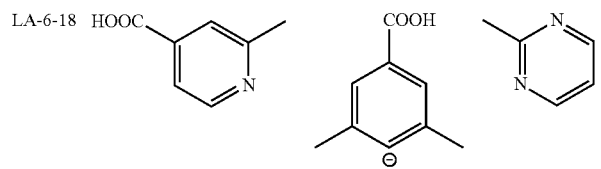
LA-6-19 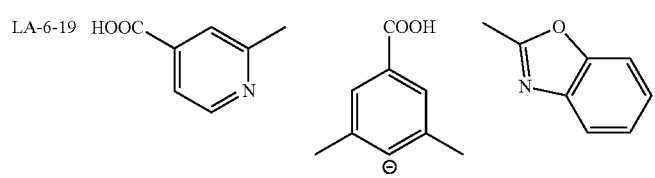
LA-6-20 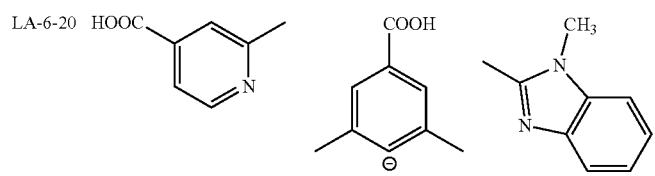

| Compound represented by Formula (B7) | | |
|---|---|---|
| 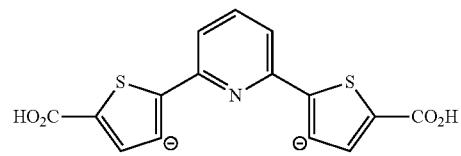 [SMILES: O=C(O)c1c[c-]c(-c2cccc(-c3[c-]cc(C(=O)O)s3)n2)s1] | | LA-7-1 |
| 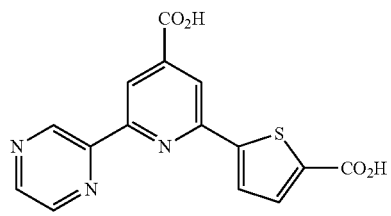 [SMILES: O=C(O)c1cc(-c2cnccn2)nc(-c2ccc(C(=O)O)s2)c1] | | LA-7-2 |
| 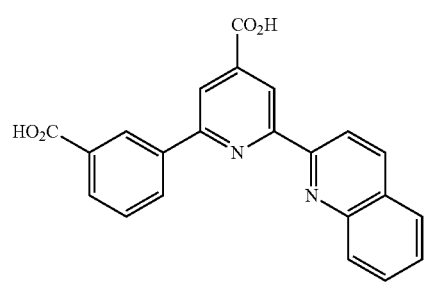 [SMILES: O=C(O)c1cccc(-c2cc(C(=O)O)cc(-c3ccc4ccccc4n3)n2)c1] | | LA-7-3 |
| 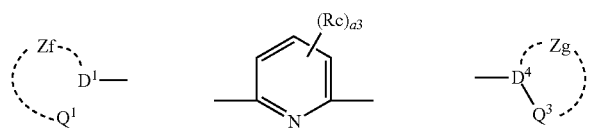 | | |
| LA-7-5 | 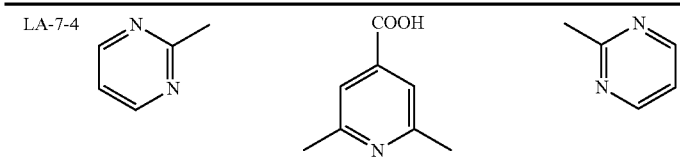 | |
| LA-7-6 | 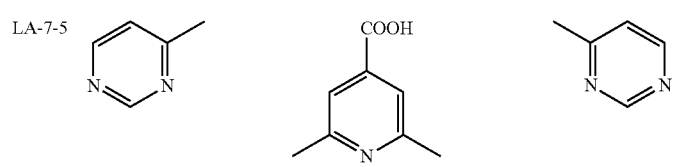 | |
| LA-7-7 | 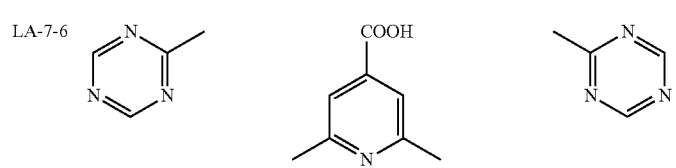 | |
| LA-7-8 | 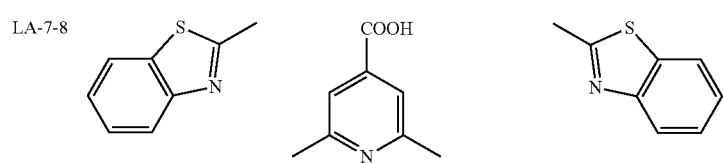 | |
Note: row LA-7-4 and LA-7-5 images combined above; see original for exact arrangement.

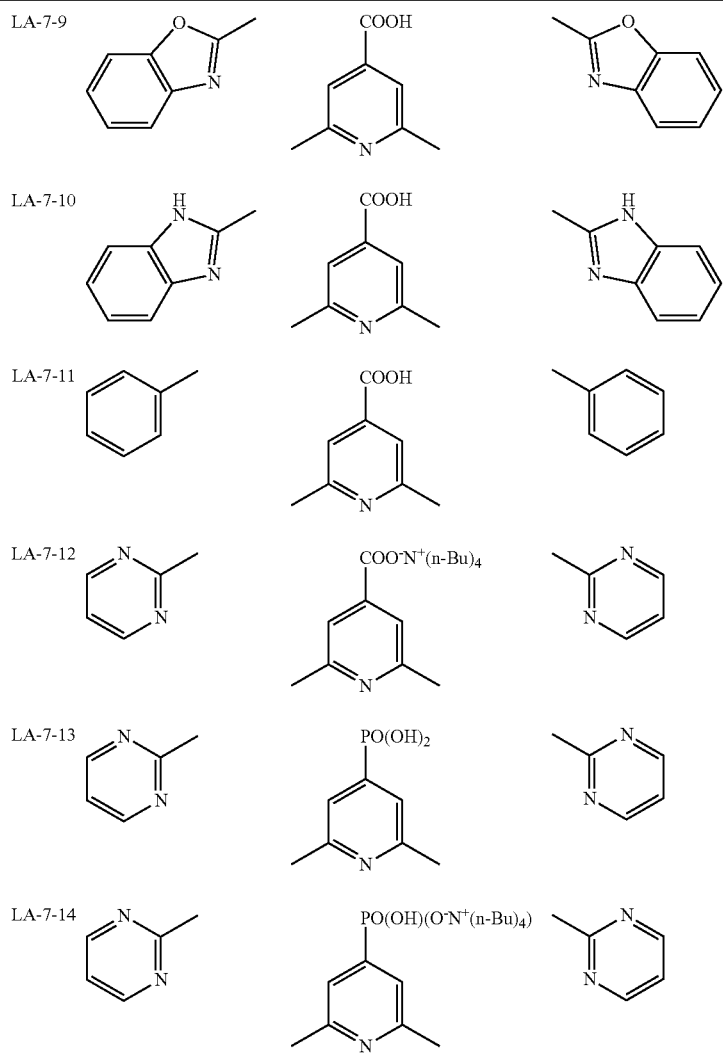
| | Compound represented by Formula (B8) |
|---|---|
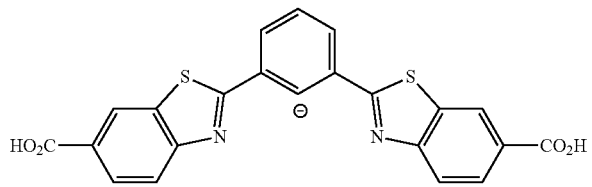 [SMILES: O=C(O)c1ccc2nc(-c3[c-]c(-c4nc5ccc(C(=O)O)cc5s4)ccc3)sc2c1]
LA-8-1
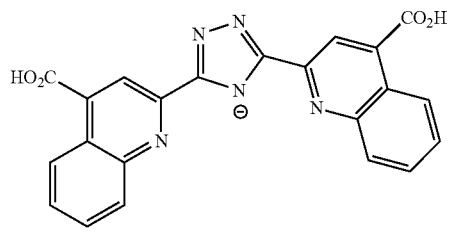 [SMILES: O=C(O)c1cc(-c2nnc(-c3cc(C(=O)O)c4ccccc4n3)[n-]2)nc2ccccc12]
LA-8-2

LA-8-3
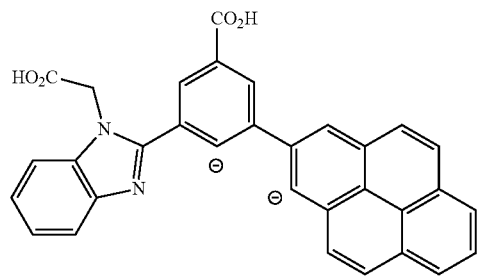 [SMILES: O=C(O)Cn1c(-c2[c-]c(-c3[c-]c4ccc5cccc6ccc(c3)c4c56)cc(C(=O)O)c2)nc2ccccc21]
| | Zf⋯D¹—  ⋯Q¹ | —D²—Q²—D³— ⋯Ze⋯ | —D⁴—Q³ ⋯Zg⋯ |
|---|---|---|---|
| LA-8-4 | | | 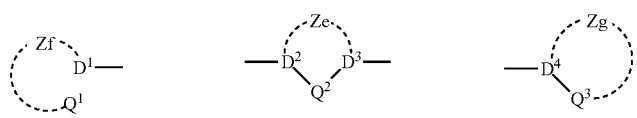 |
| LA-8-5 | | | 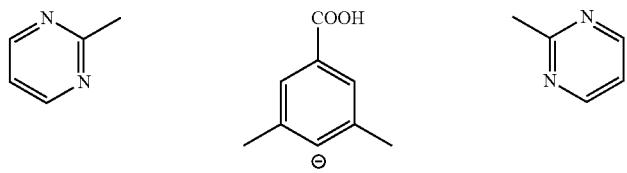 |
| LA-8-6 | | | 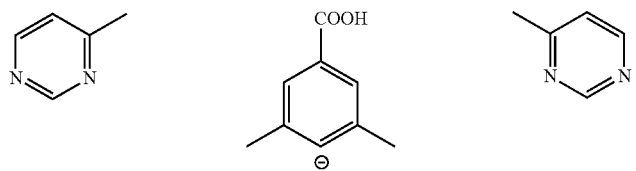 |
| LA-8-7 | | | 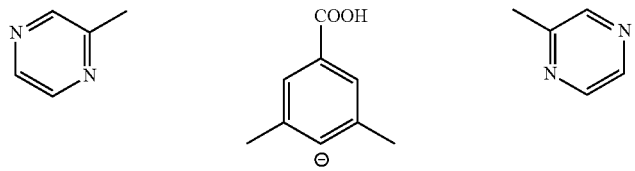 |
| LA-8-8 | | | 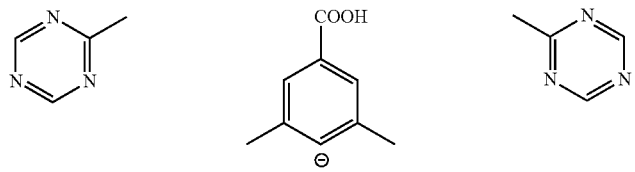 |
| LA-8-9 | | | 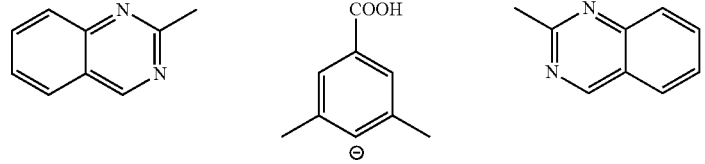 |

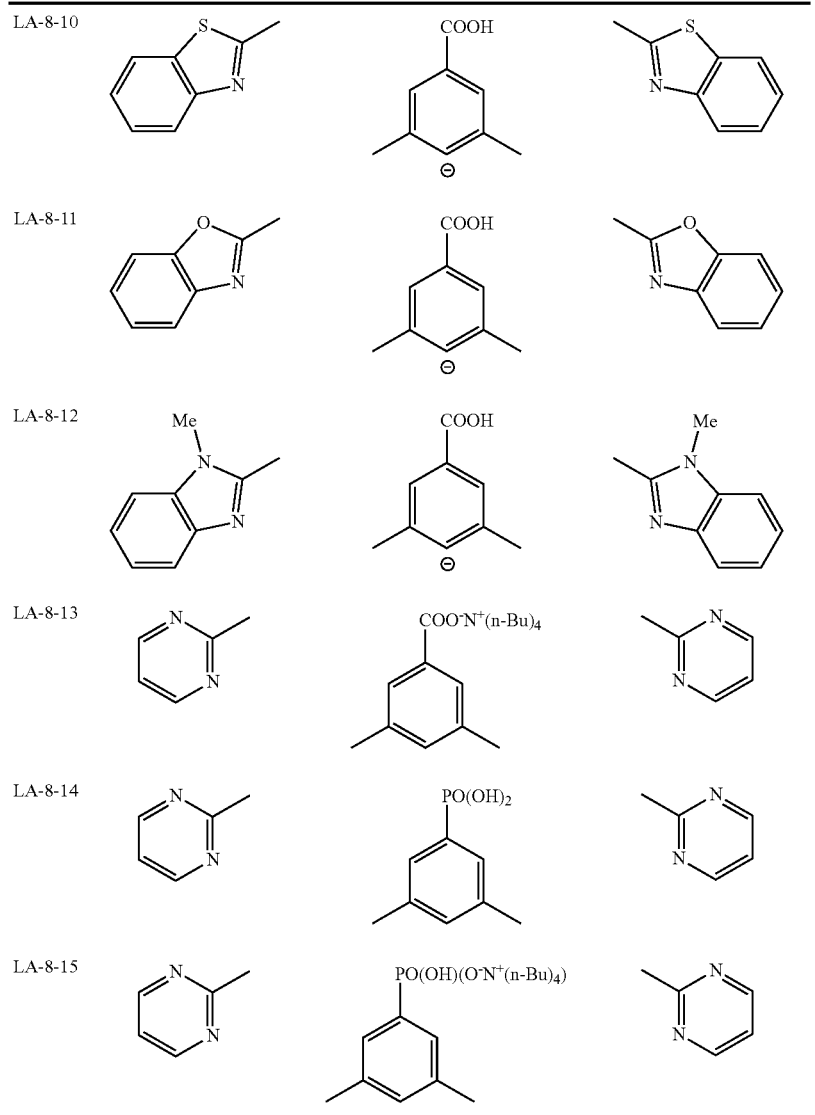

In the above, "tBu" represents a t-butyl group, "n-Bu" represents an n-butyl group, and "Ph" represents a phenyl group (—C$_6$H$_5$).

The ligand LA represented by formula (B) can be readily synthesized in the same manner as the ligand LD represented by formula (A).

—Ligand X—

X represents a monodentate ligand, and examples thereof includes: a monodentate ligand which coordinates by an anion selected from the group consisting of acyloxy anion, acylthio anion, thioacyloxy anion, thioacylthio anion, acylaminooxy anion, thiocarbamate anion, dithiocarbamate anion, thiocarbonate anion, dithiocarbonate anion, trithiocarbonate anion, acyl anion, thiocyanate anion, isothiocyanate anion, cyanate anion, isocyanate anion, cyano anion, alkylthio anion, arylthio anion, alkoxy anion, and aryloxy anion; or a monodentate ligand which coordinates by a group derived from these anions; or a monodentate ligand selected from the group of anions, atoms or compounds (including compounds in which a hydrogen atom is substituted with the anion) consisting of a halogen atom, cyano, carbonyl, dialkylketone, carbonamide, thiocarbonamide, and thiourea. In a case where the ligand X contains an alkyl group, an alkenyl group, an alkynyl group, an alkylene group or the like, these may be a straight chain or a branched chain, and these may be substituted or unsubstituted. Further, in a case where the ligand X contains an aryl group, a heterocyclic group, a cycloalkyl group or the like, these may be substituted or unsubstituted, and may be a single ring or a condensed ring.

In the present invention, X is preferably cyanate anion, isocyanate anion, thiocyanate anion, isothiocyanate anion, selenocyanate anion, and isoselenocyanate anion, more preferably isocyanate anion, isothiocyanate anion, and isoselenocyanate anion, and particularly preferably isothiocyanate anion.

—Metal Atom M—

M is a center metal of the metal complex dye. In formula (I), M represents Ru or Os, preferably Ru, in the present invention.

—Counter Ion CI for Neutralizing Charge—

CI in formula (I) represents a counter ion in the case where the counter ion is necessary to neutralize a charge.

Generally, whether the dye is cationic or anionic, or has a net ionic charge, depends on the metal, the ligand and the substituent, in the metal complex dye.

In the case where the substituent has a dissociative group or the like, the metal complex dye represented by formula (I) may have a negative charge arising from dissociation. In this case, an electric charge of the metal complex dye represented by formula (I) as a whole is electrically neutralized by the counter ion CI.

When the counter ion CI is a positive counter ion, examples of the counter ion CI include an inorganic or organic ammonium ion (for example, tetraalkyl ammonium ion, pyridinium ion, and the like), a phosphonium ion (for example, a tetralkylphosphonium ion, an alkyltriphenylphosphonium ion, and the like), an alkali metal ion, and a proton.

When the counter ion CI is a negative counter ion, the negative counter ion may be an inorganic negative ion or an organic negative ion. Examples thereof include a halogen negative ion (for example, fluoride ion, chloride ion, bromide ion, iodide ion), a substituted arylsulfonate ion (for example, p-toluene sulfonate ion, p-chlorobenzene sulfonate ion), an aryldisulfonate ion (for example, 1,3-benzene disulfonate ion, 1,5-naphthalene disulfonate ion, 2,6-naphthalene disulfonate ion), an alkylsulfate ion (for example, methylsulfate ion), a sulfate ion, a thiocyanate ion, a perchlorate ion, a tetrafluoroborate ion, a hexafluorophosphae ion, a picrate ion, an acetate ion, and a trifluoromethane sulfonate ion. Alternatively, as a charge balance counter ion, an ionic polymer or another dye with the opposite charge from the dye in interest may be used. Alternatively, a metal complex ion (for example, bisbenzene-1,2-dithiolatonickel (III) and the like) may be used.

In the present invention, CI is preferably an inorganic or organic ammonium ion, particularly preferably tetrabutylammonium ion, sodium ion, or proton.

—m1 to m3—

In formula (I), m1 represents 1 or 2, preferably 1.
In formula (I), m2 represents 1.
In formula (I), m3 represents 0 or 1, preferably 0.

Specific examples of the metal complex dye of the present invention are shown below, but the present invention is not limited to these. In the following structures, although CI in formula (I) is represented by a proton, it may be tetrabutylammonium ion ($^+$NBu$_4$), sodium ion, or the like.

D-1

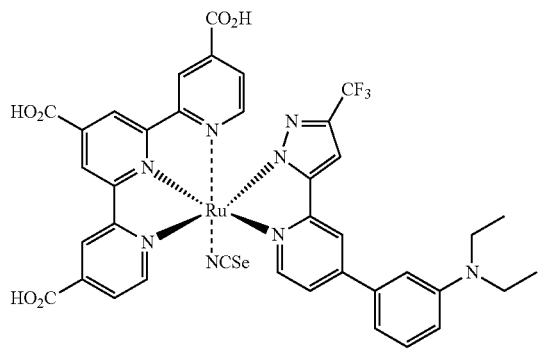

D-2

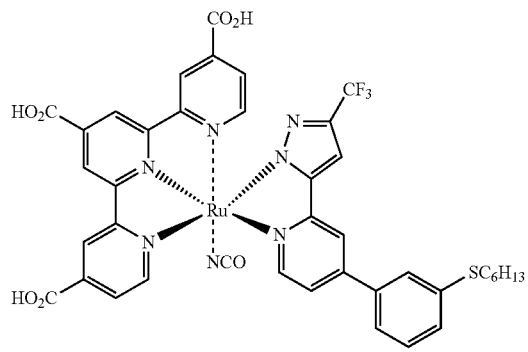

D-3

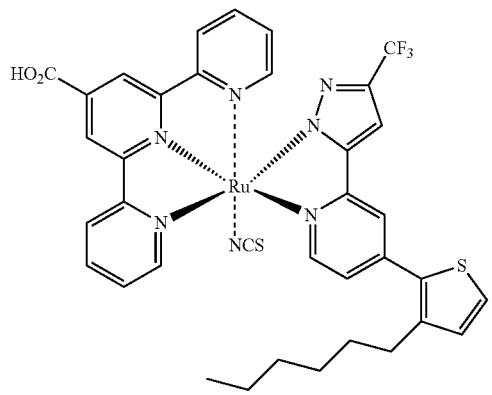

D-4

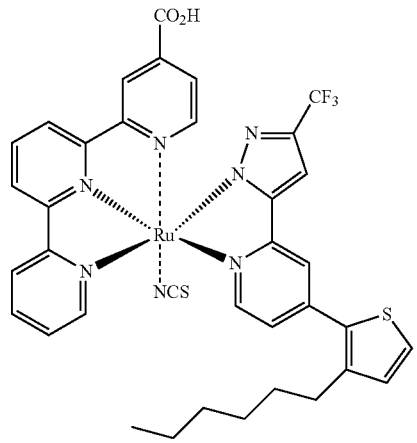

D-5
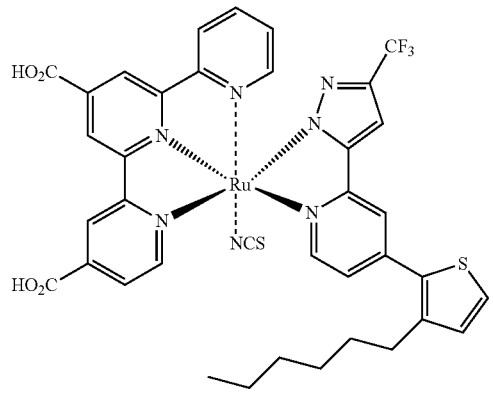
D-6
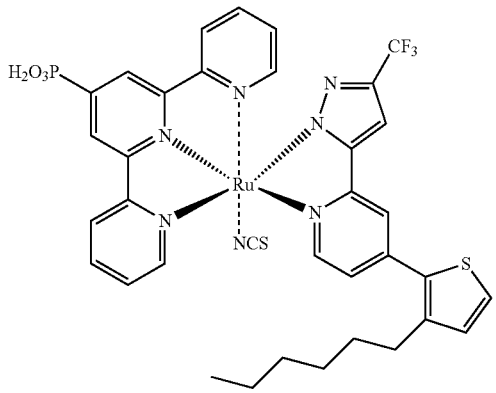
D-7
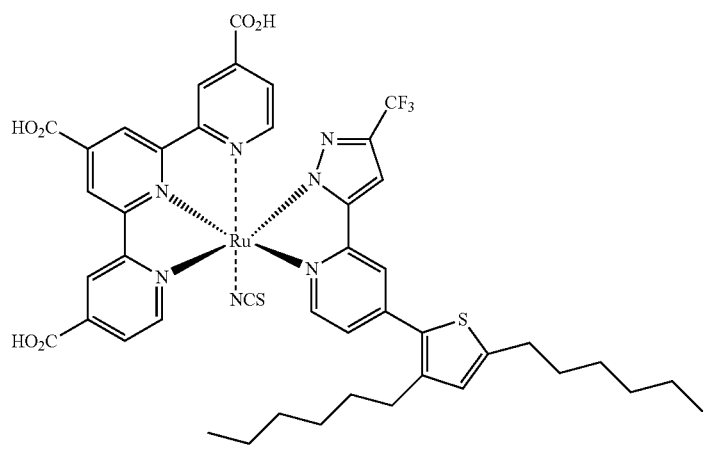
D-8
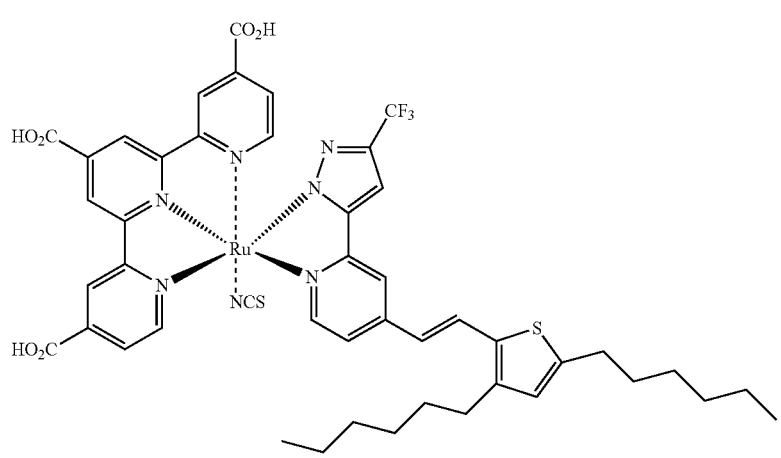

-continued
D-9
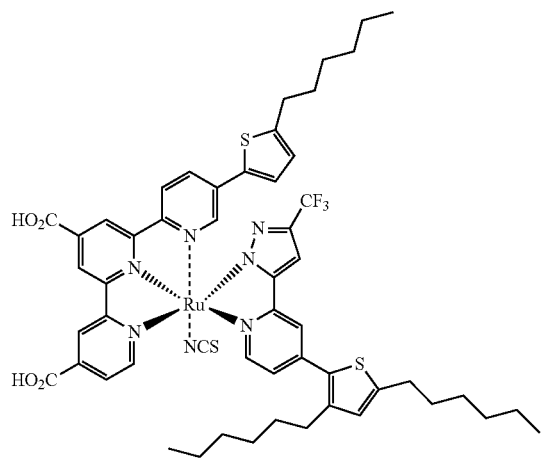
D-10
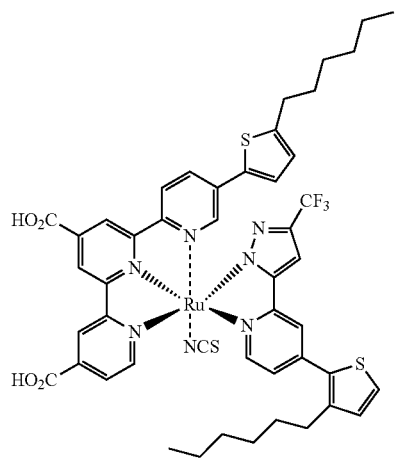
D-11
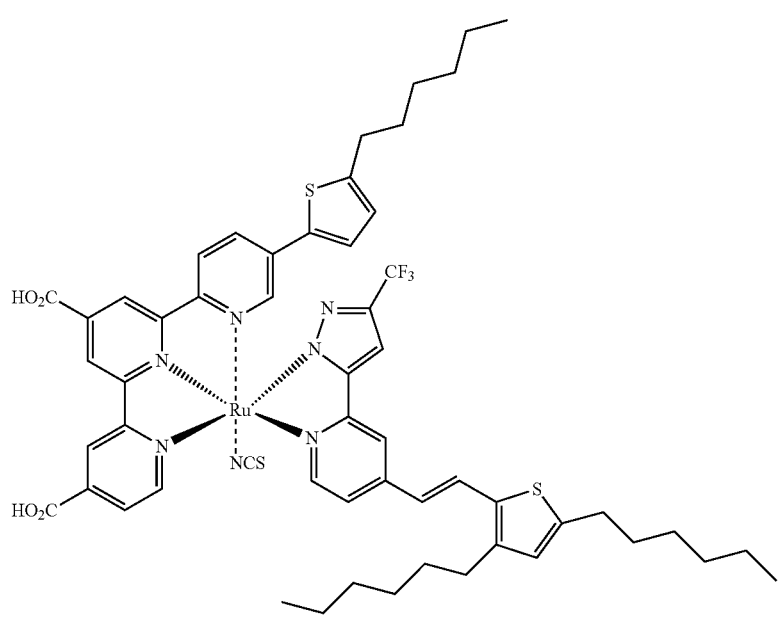
D-12
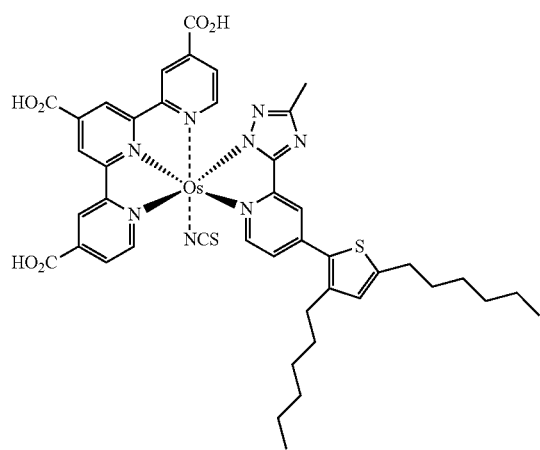
D-13
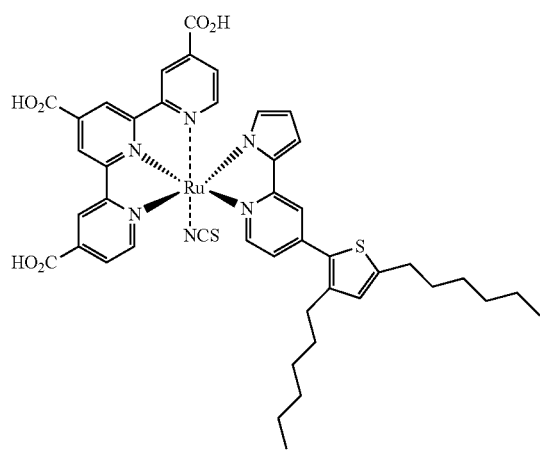

-continued
D-14
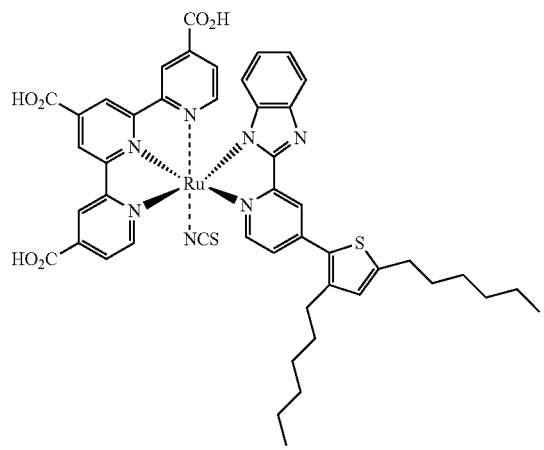
D-15
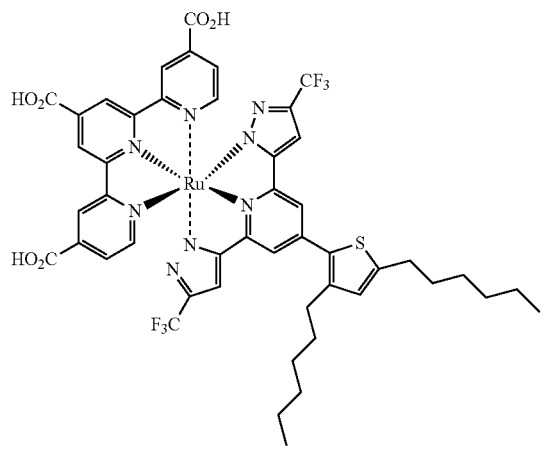
D-16
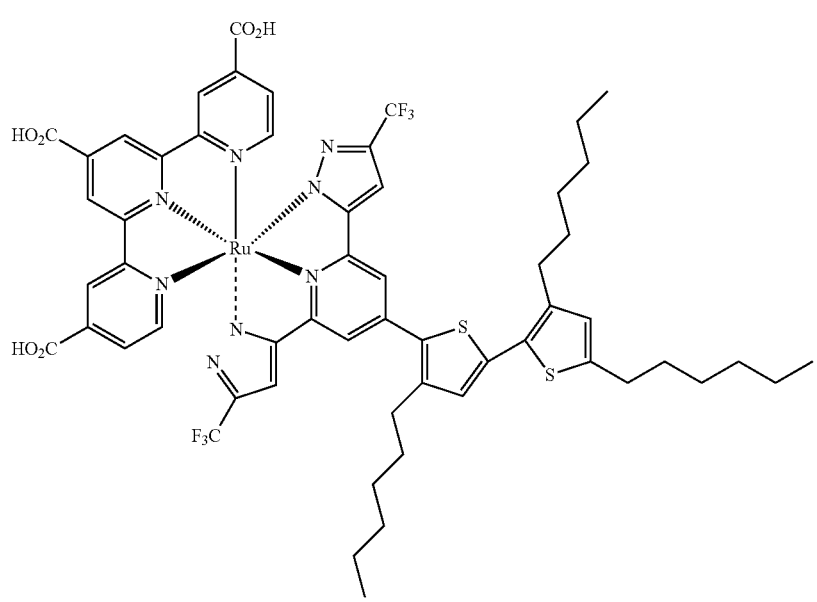
D-17
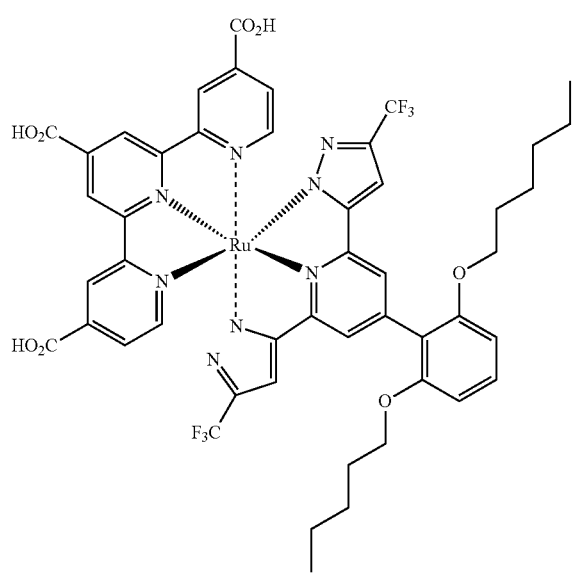

D-18
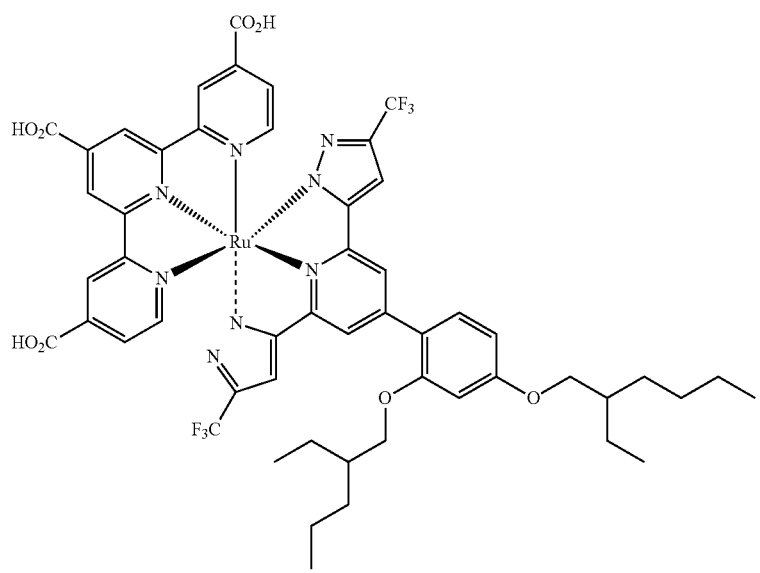
D-19
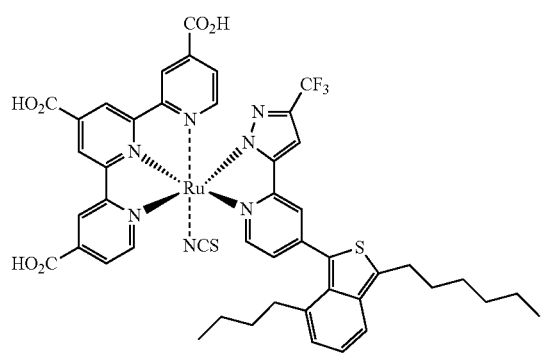
D-20
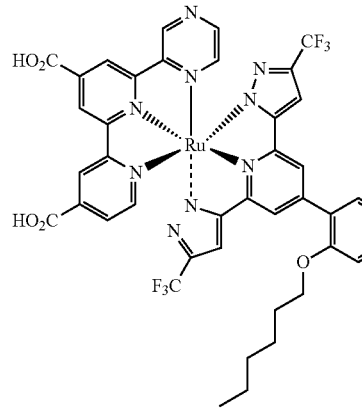
D-21
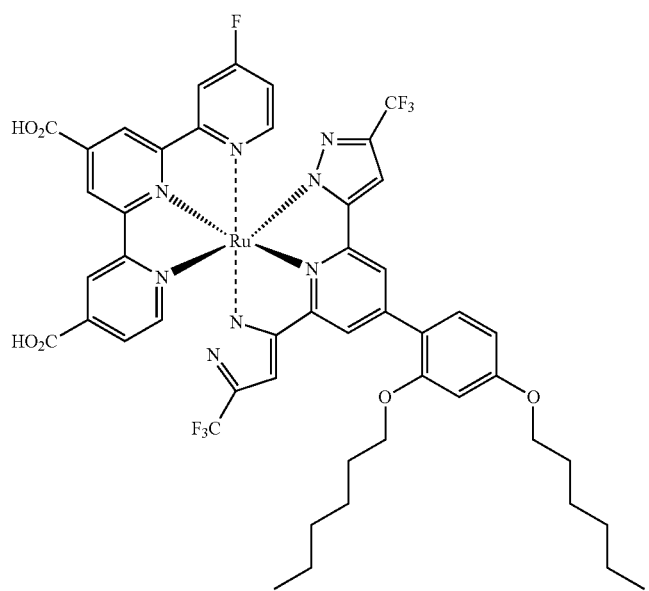

-continued
D-22
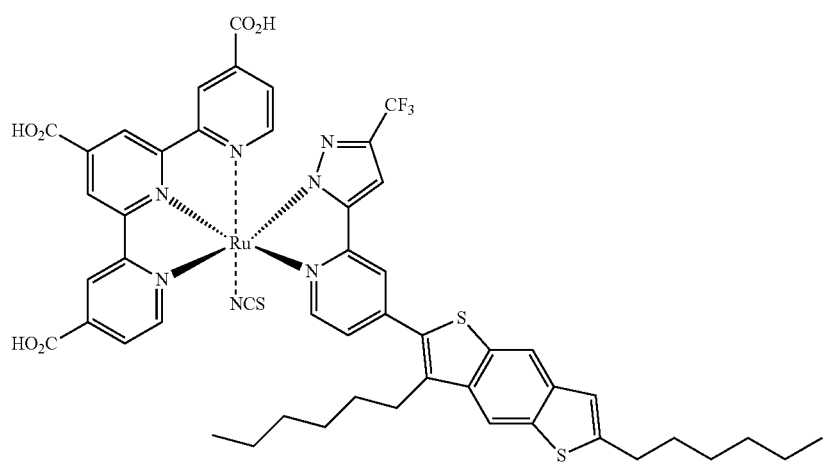
D-23
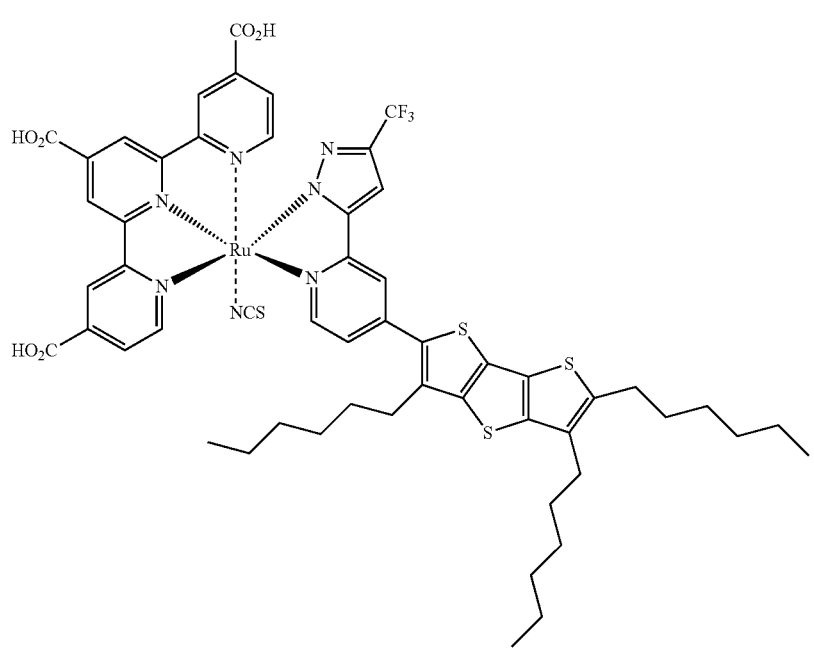
D-24
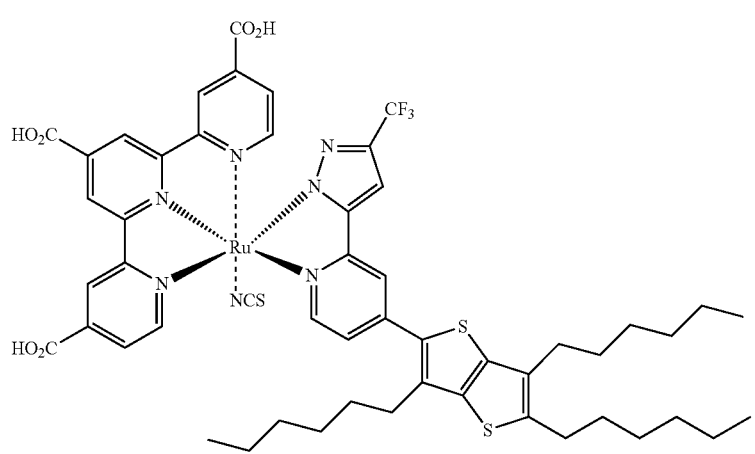

D-25
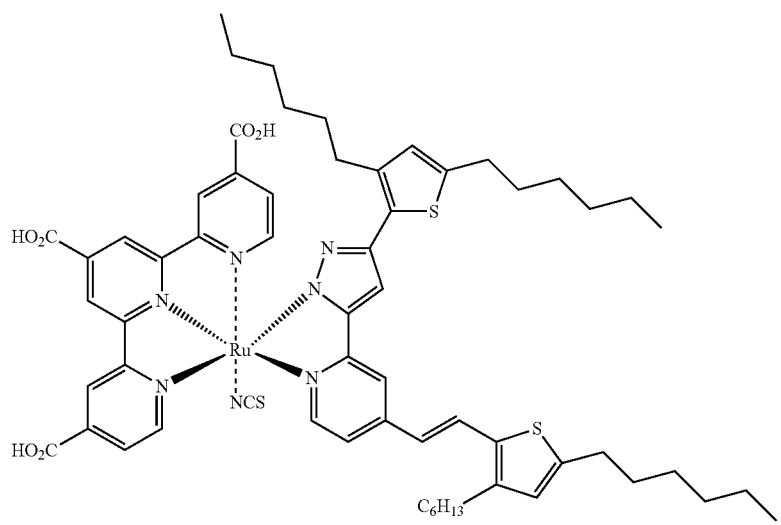
D-26
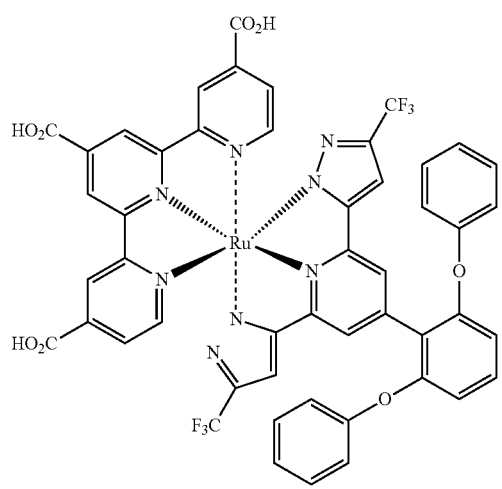
D-27
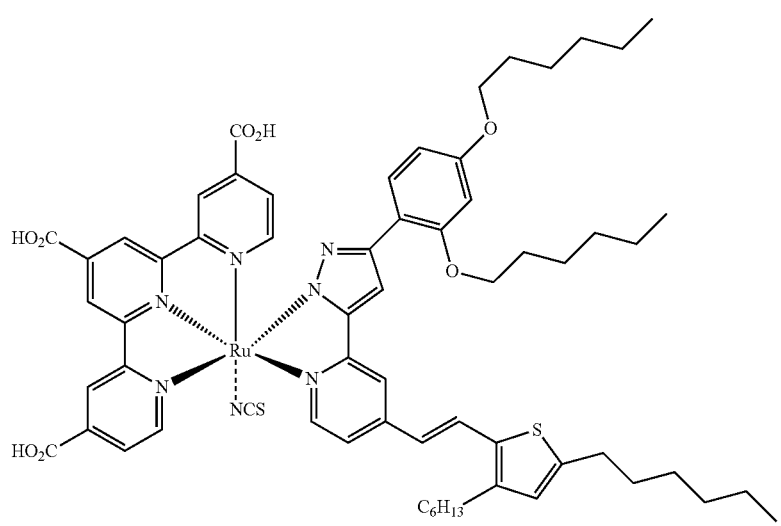

-continued
D-28
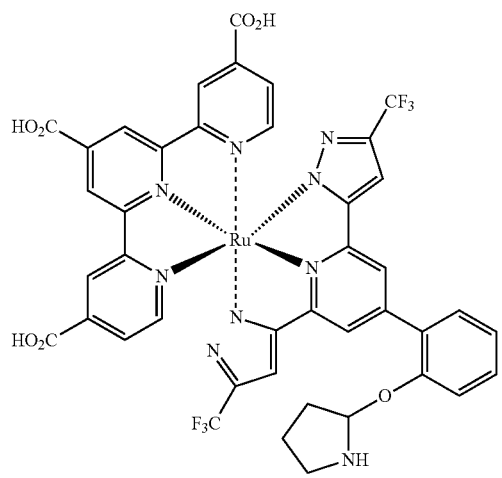
D-29
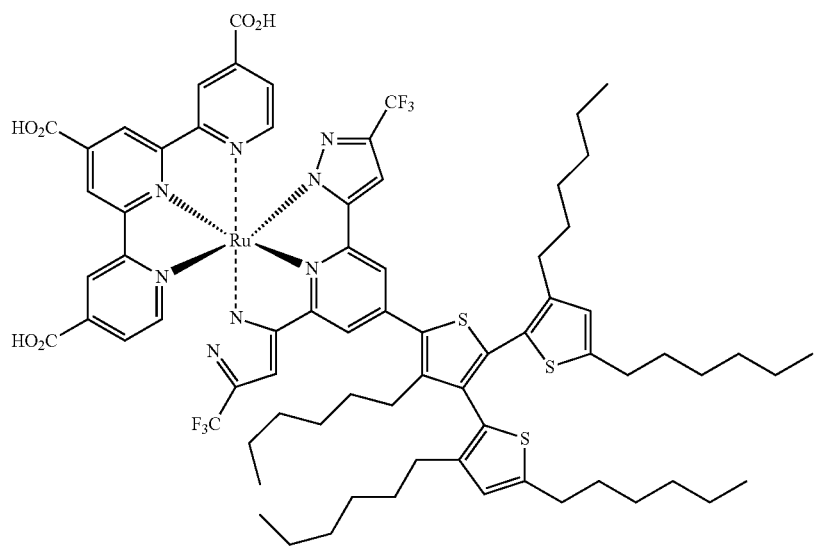
D-30
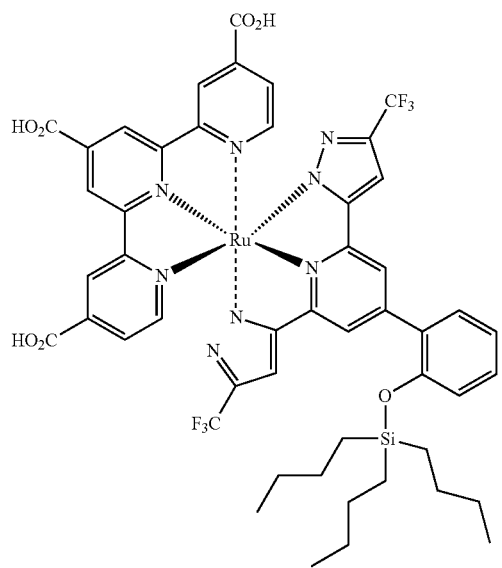
D-31
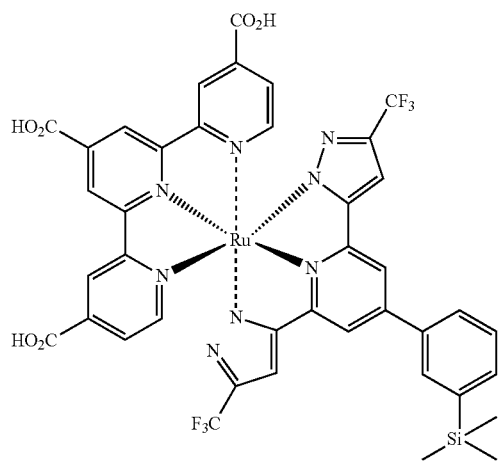

-continued
D-32
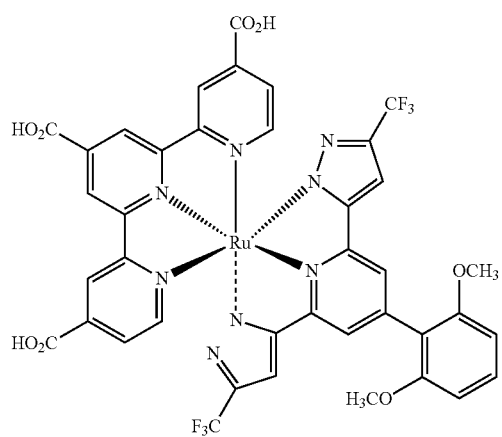
D-33
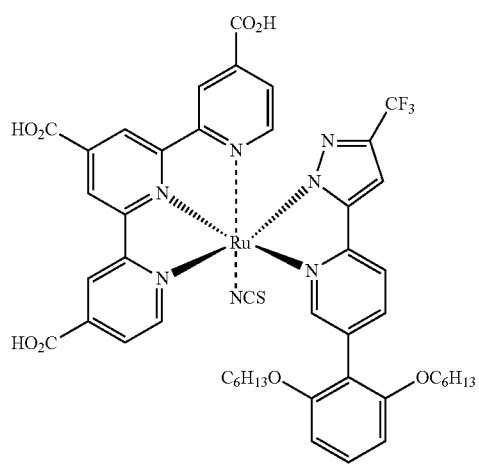
D-34
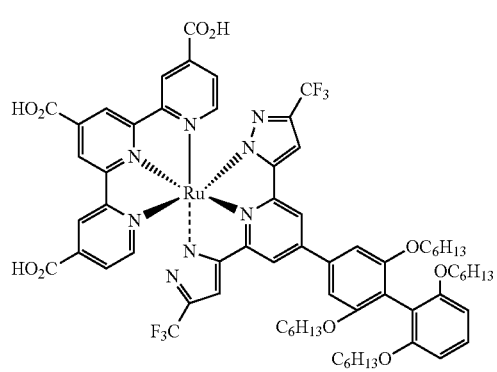
D-35
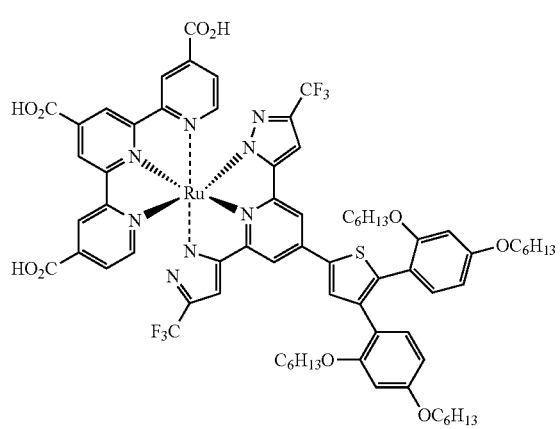
D-36
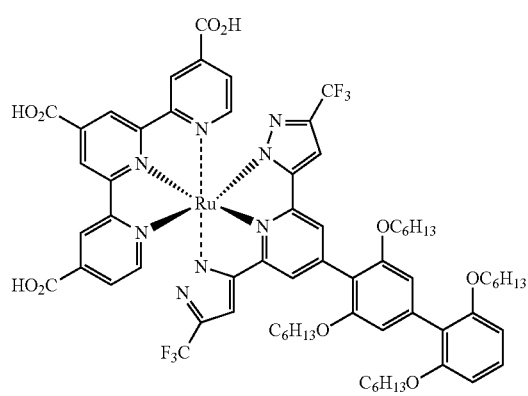
D-37
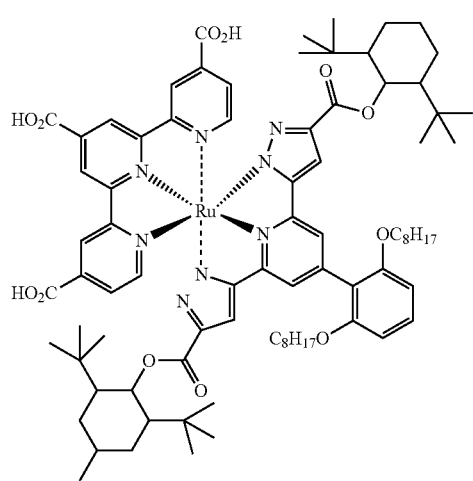

-continued
D-38
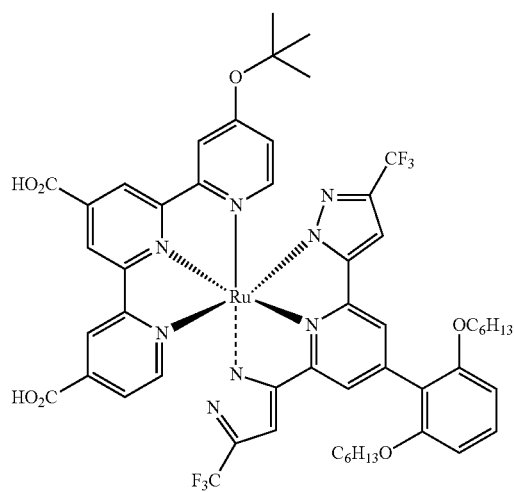
D-39
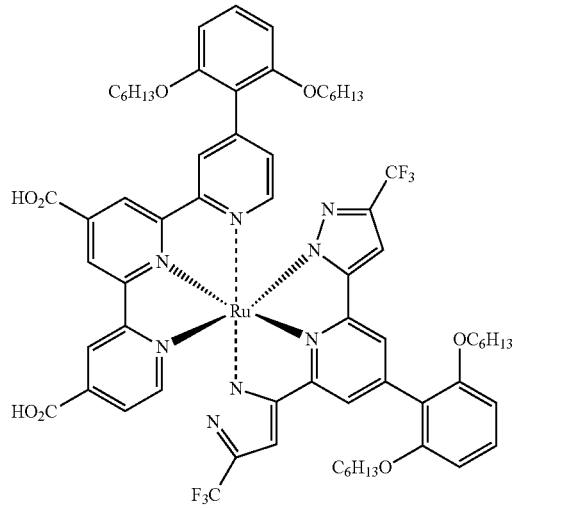
D-40
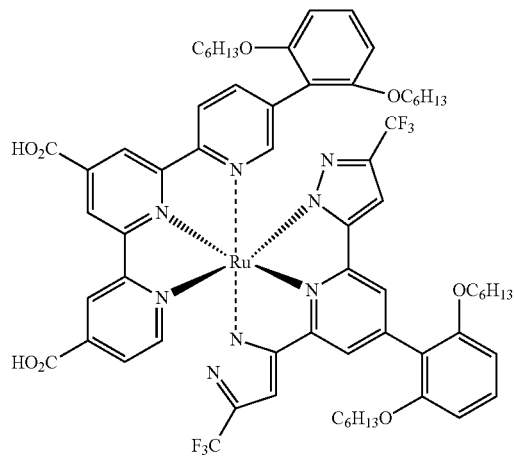
D-41
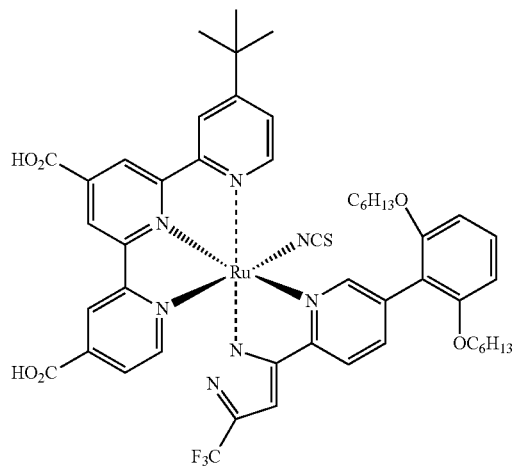
D-42
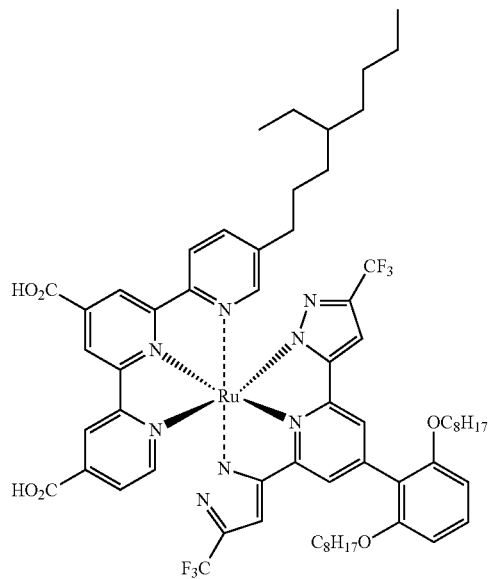
D-43
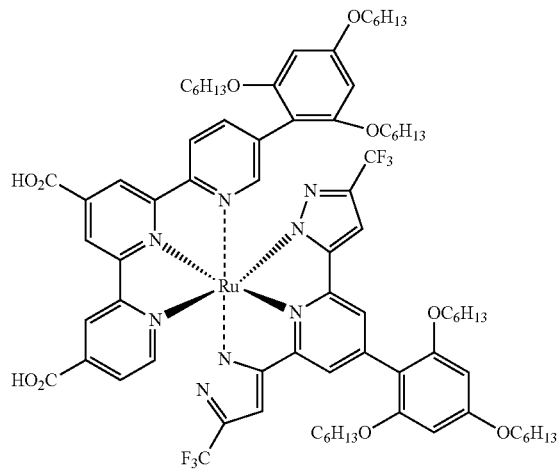

-continued
D-44
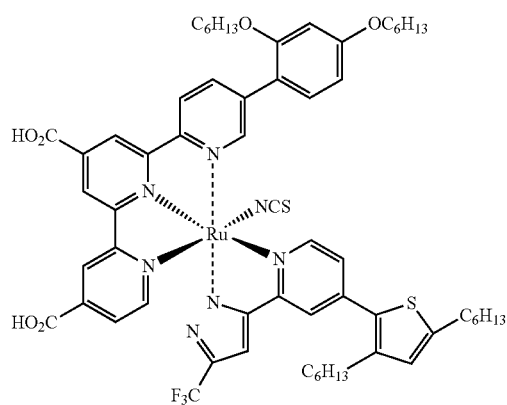
D-45
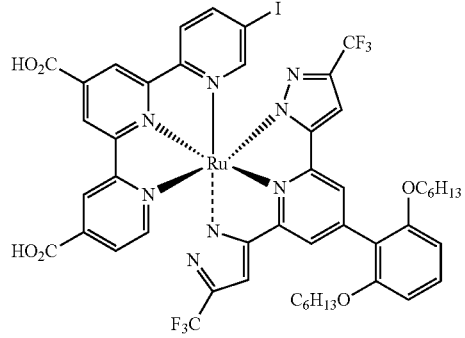
D-46
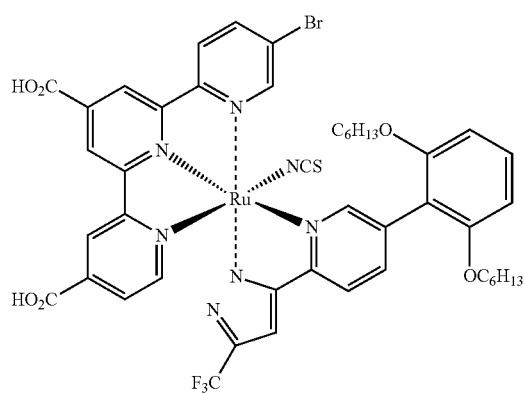
D-47
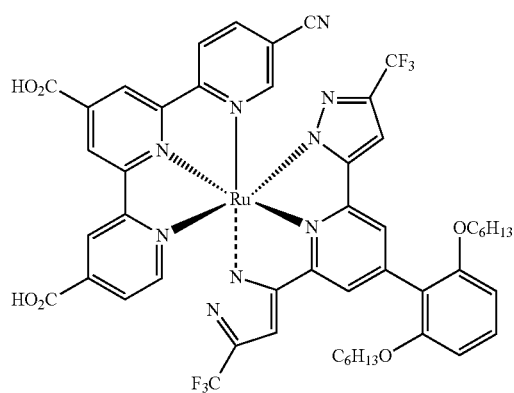
D-48
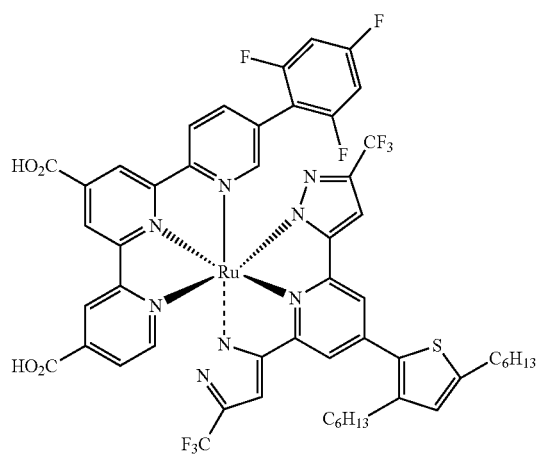
D-49
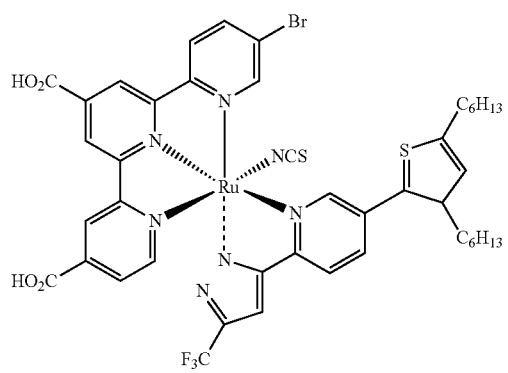

-continued
D-50
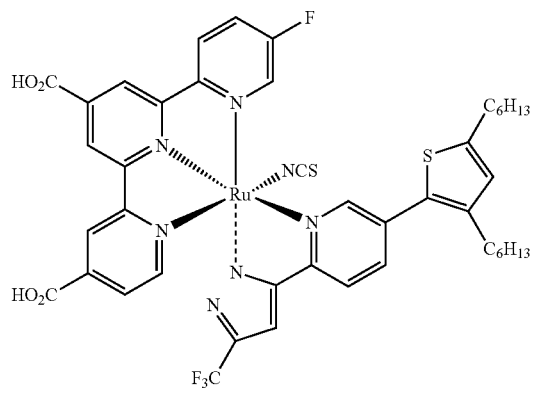
D-51
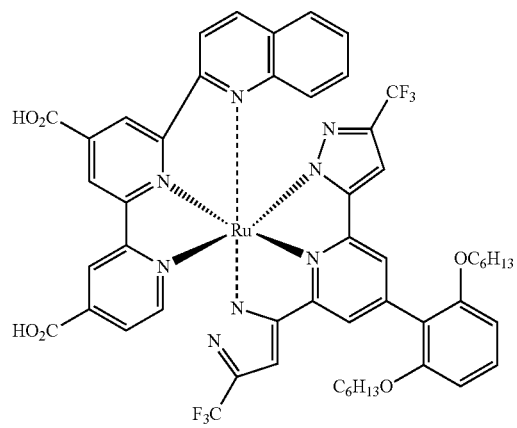
D-52
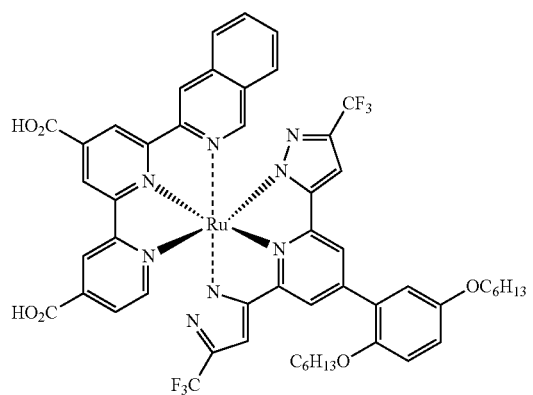
D-53
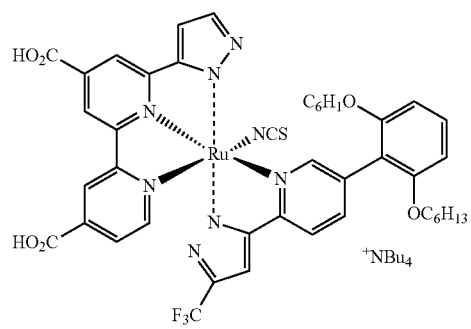
D-54
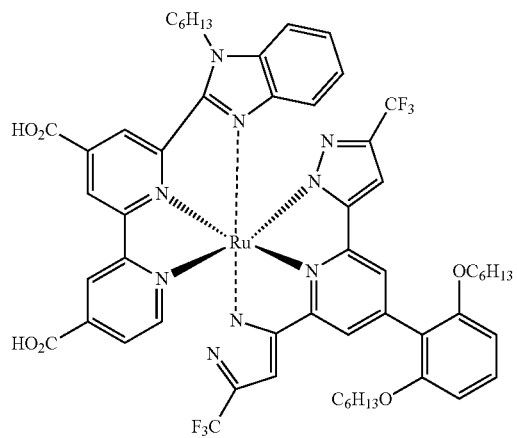
D-55
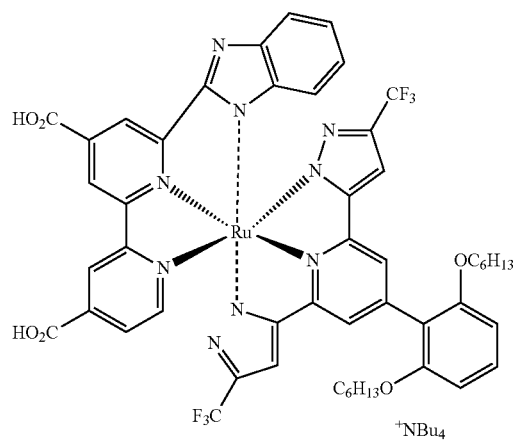

-continued
D-56
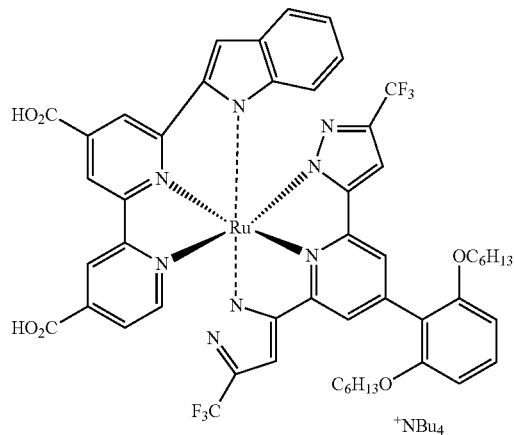
D-57
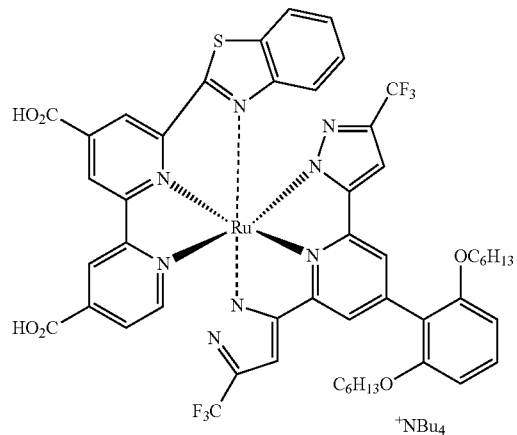
D-58
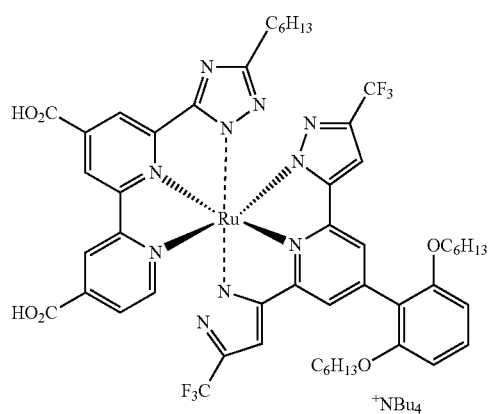
D-59
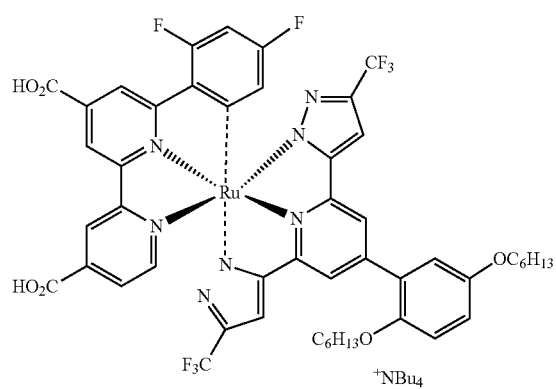
D-60
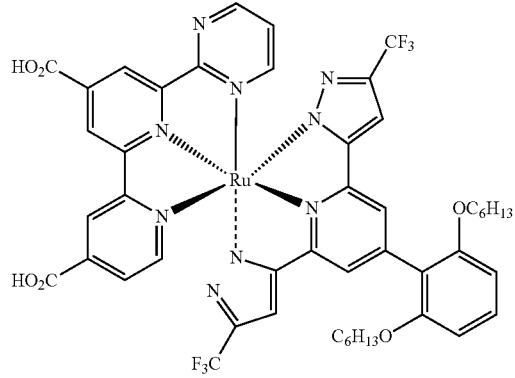
D-61
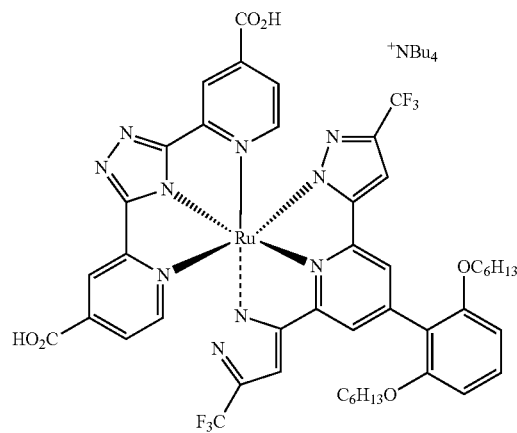

-continued
D-62
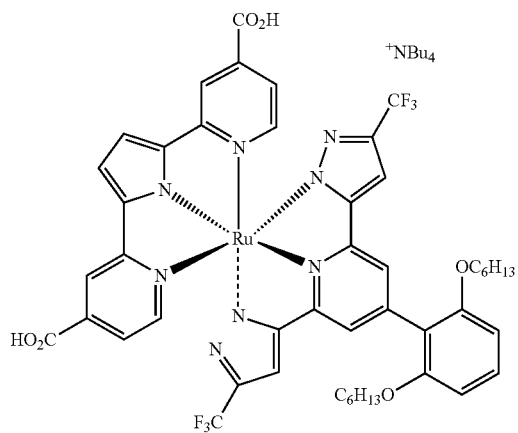
D-63
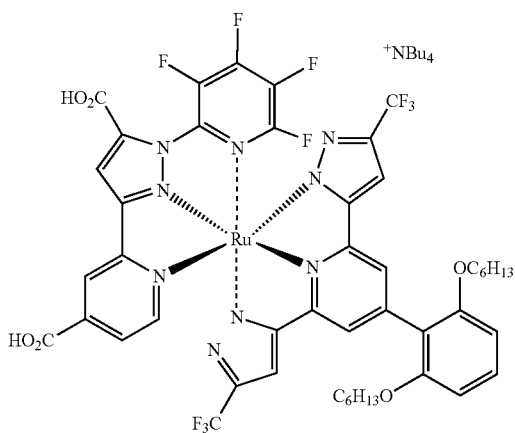
D-64
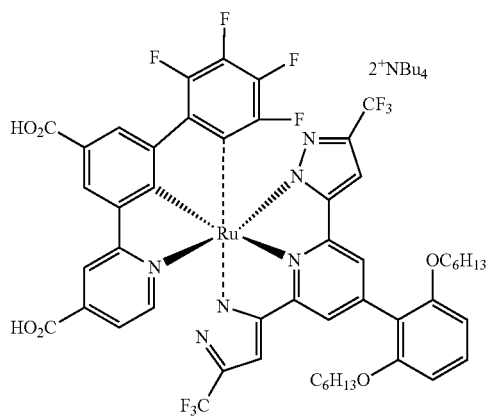
D-65
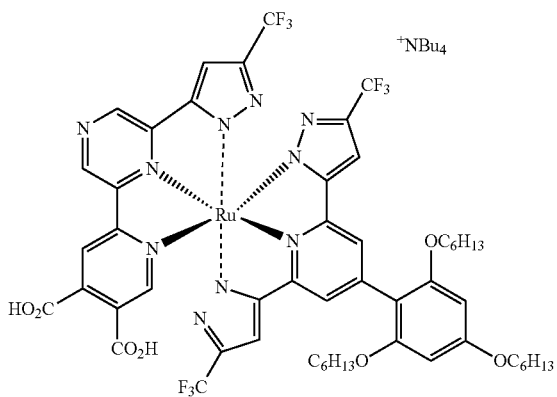
D-66
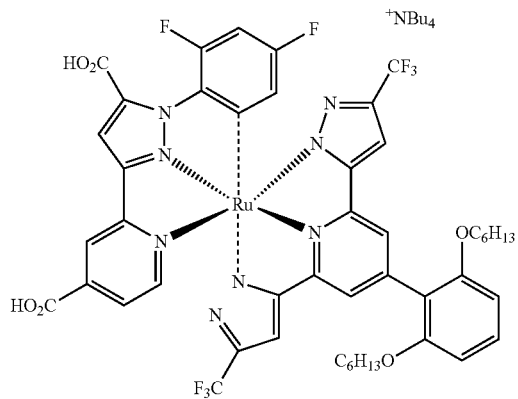
D-67
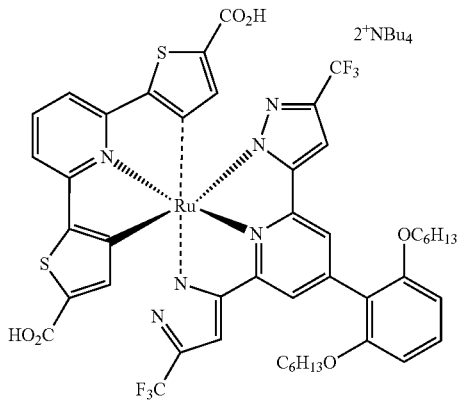

-continued
D-68
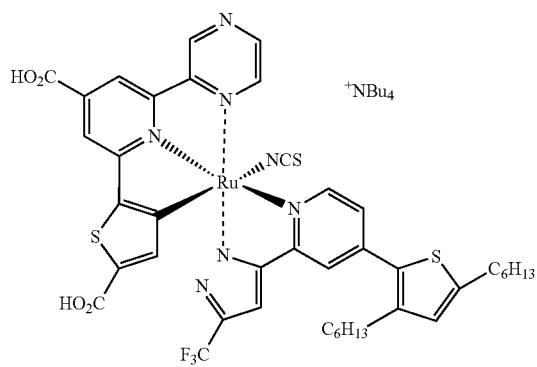
D-69
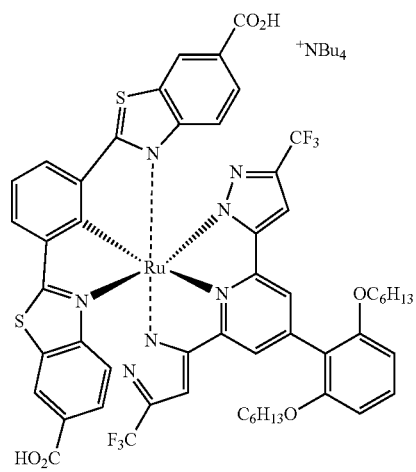
D-70
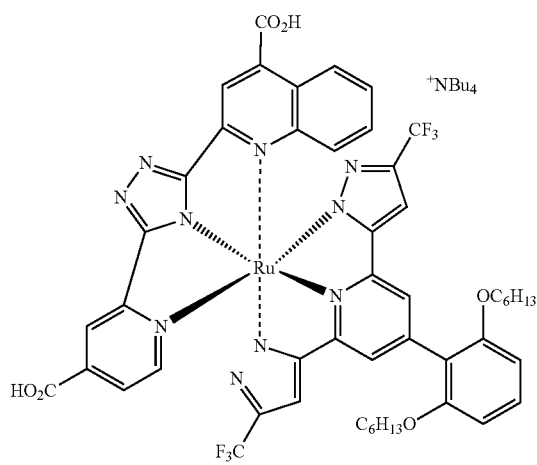
D-71
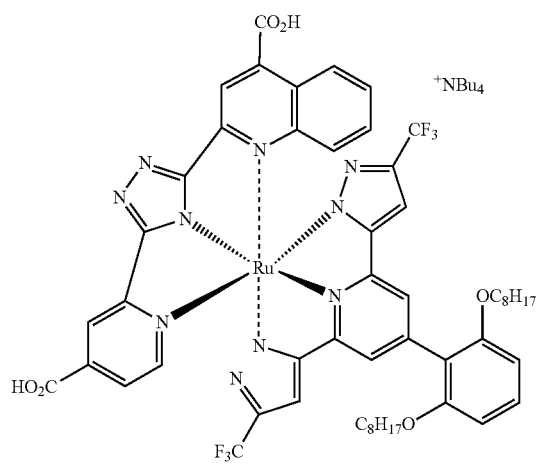
D-72
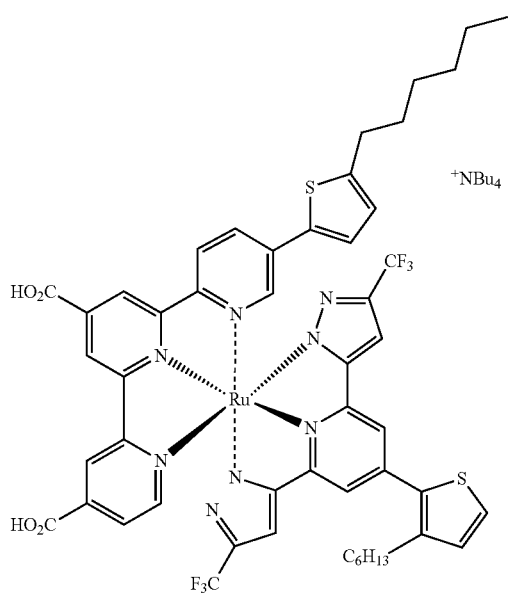
D-73
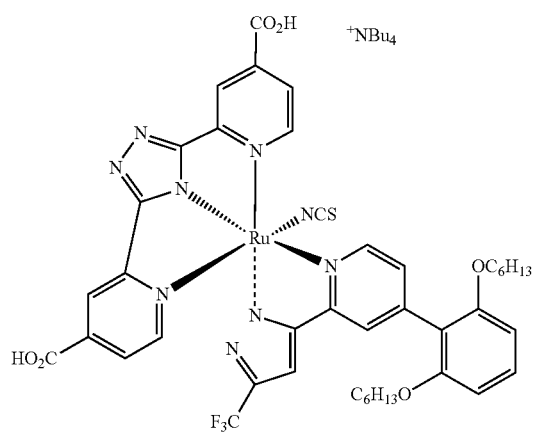

-continued
| D-74 | D-75 |
|---|---|
| 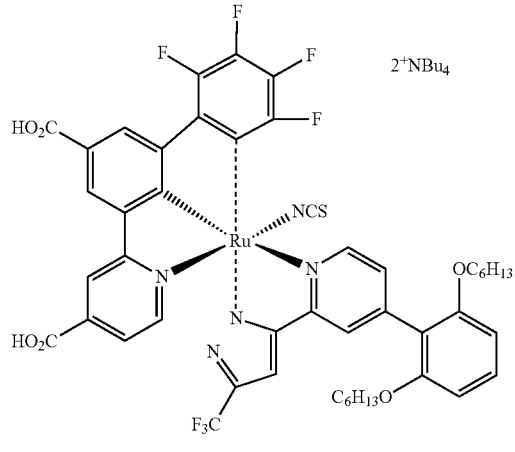 | 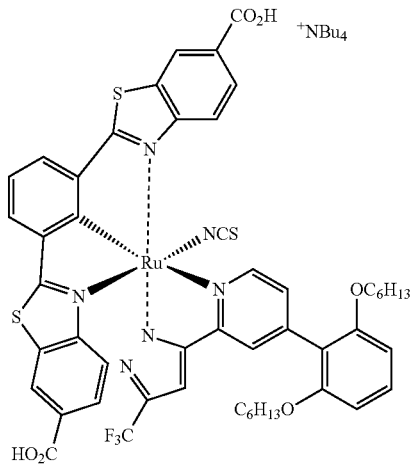 |
| D-76 | D-77 |
| 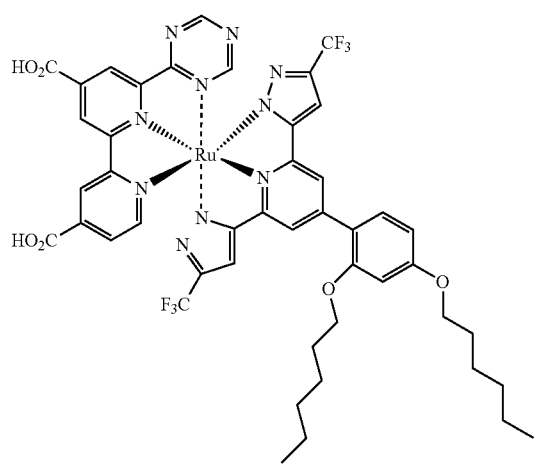 | 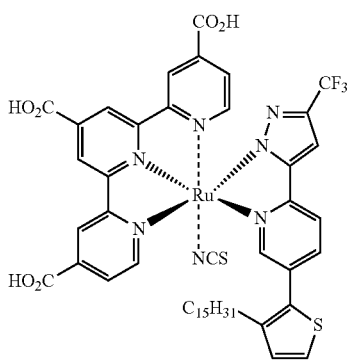 |
| D-78 | D-79 |
| 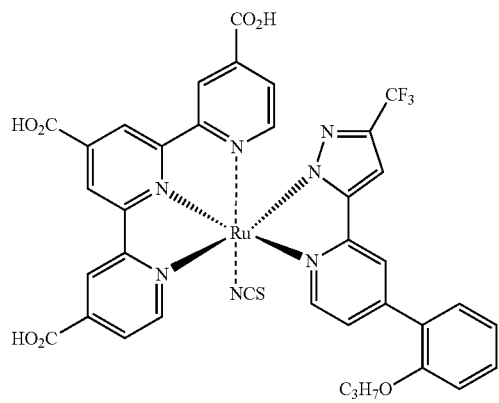 | 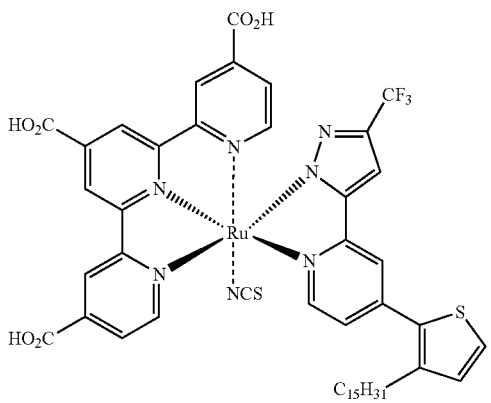 |

-continued
D-80
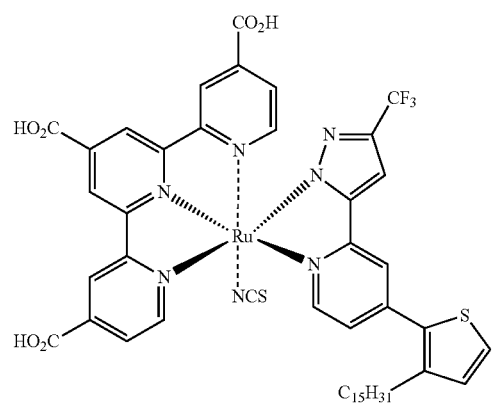
D-81
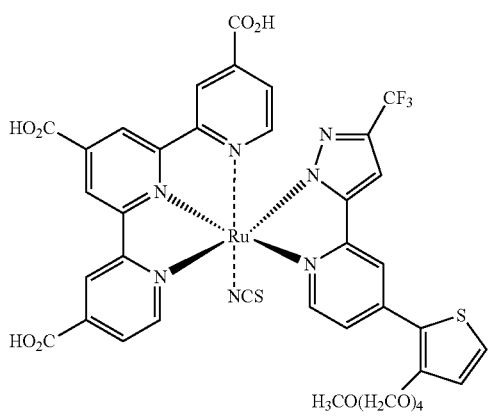
D-82
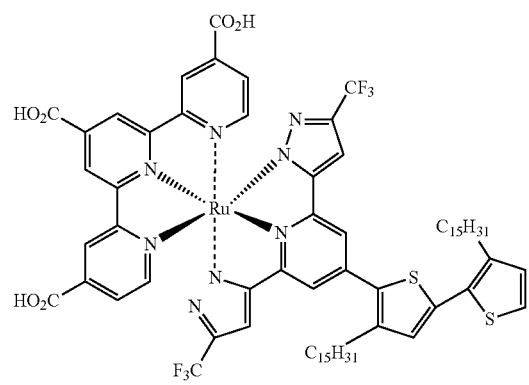
D-83
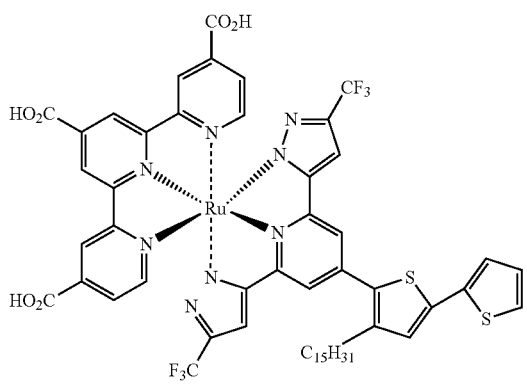
D-84
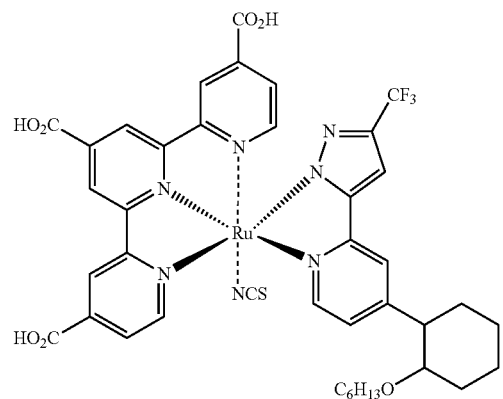
D-85
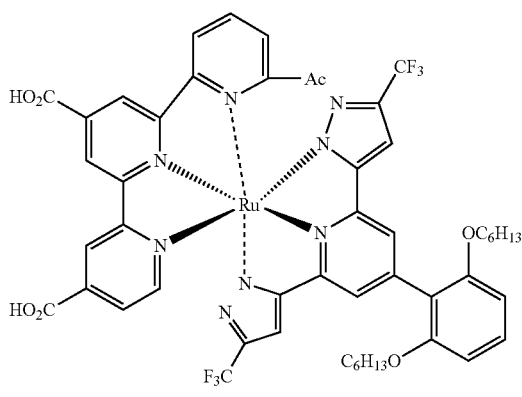
D-86
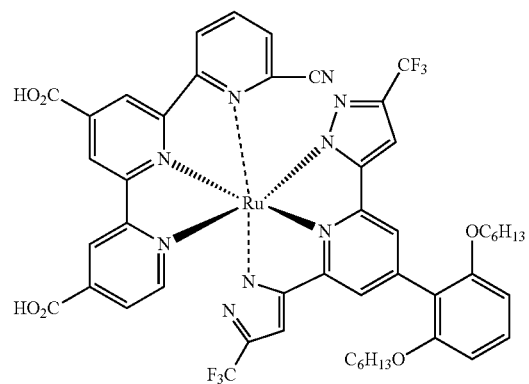
D-87
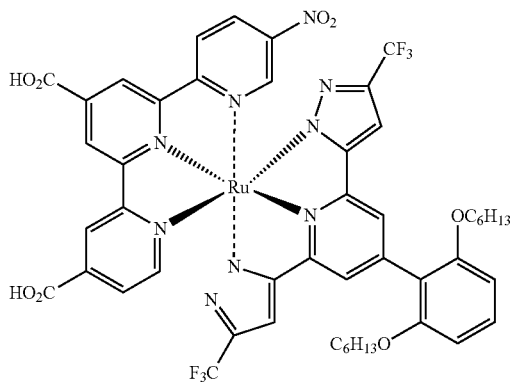

-continued
D-88
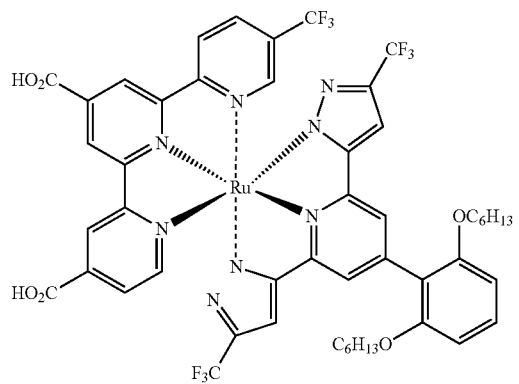
D-89
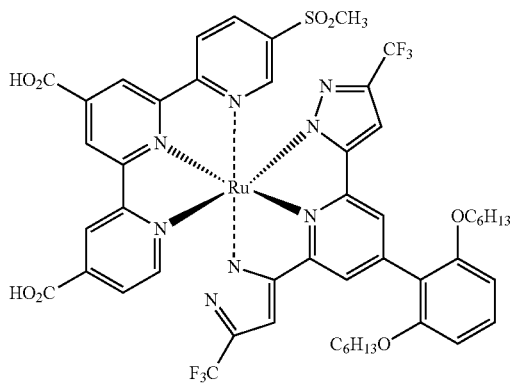
D-90
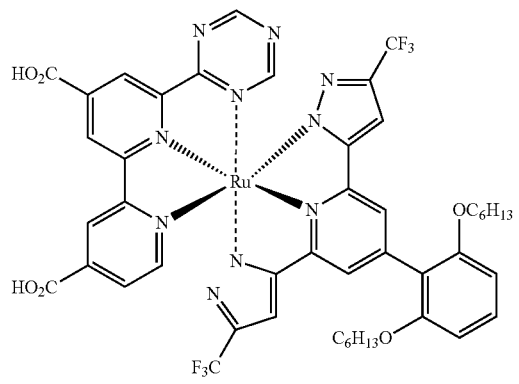
D-91
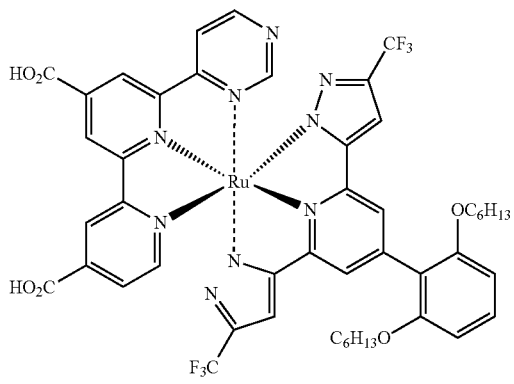
D-92
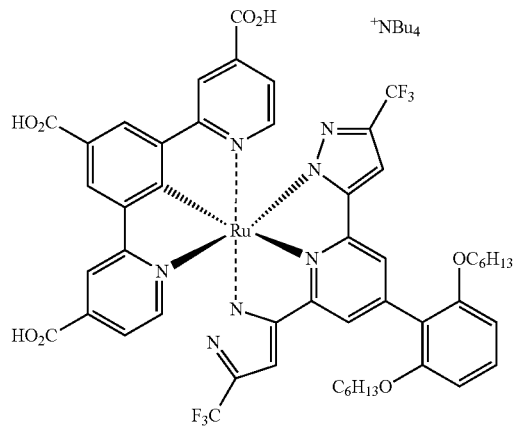
D-93
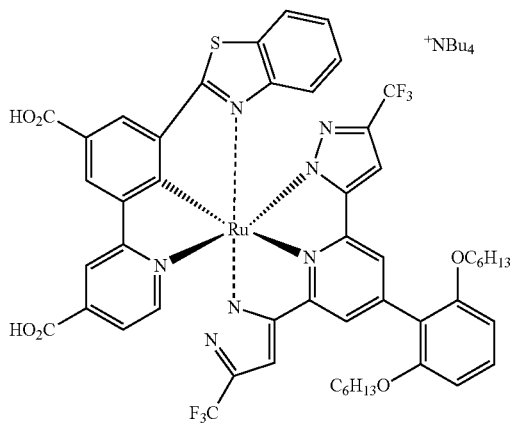
D-94
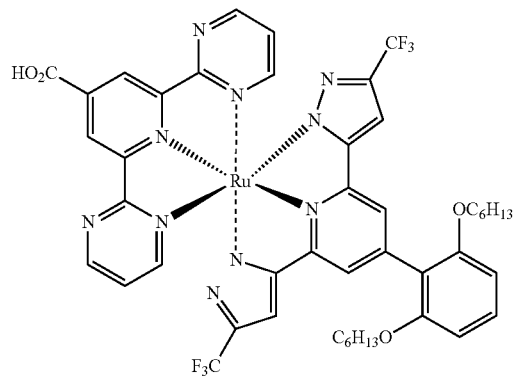
D-95
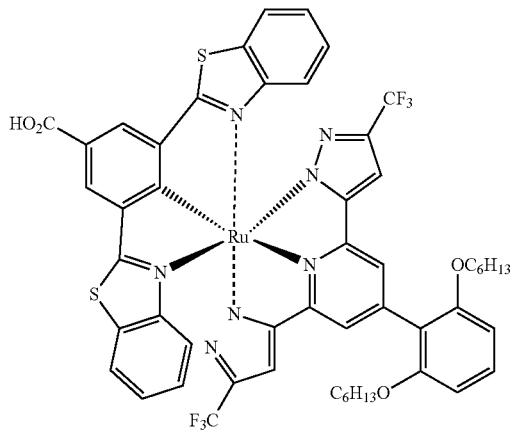

-continued

D-96

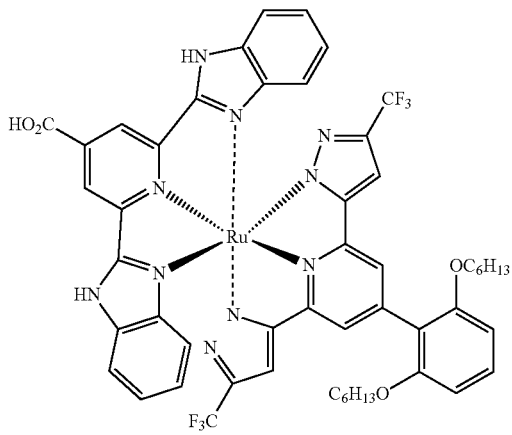

D-97

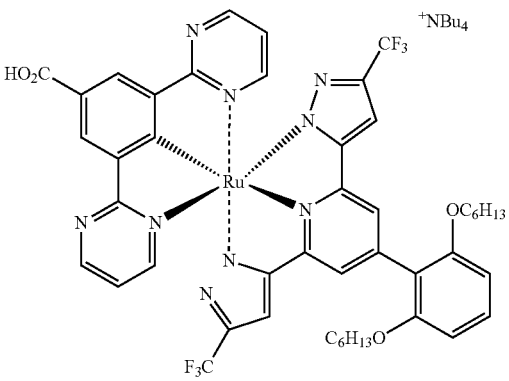

D-98

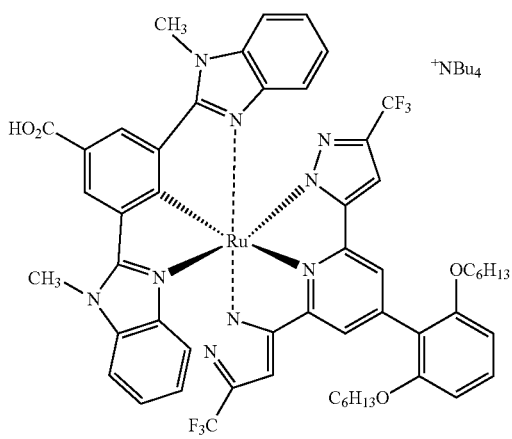

D-99

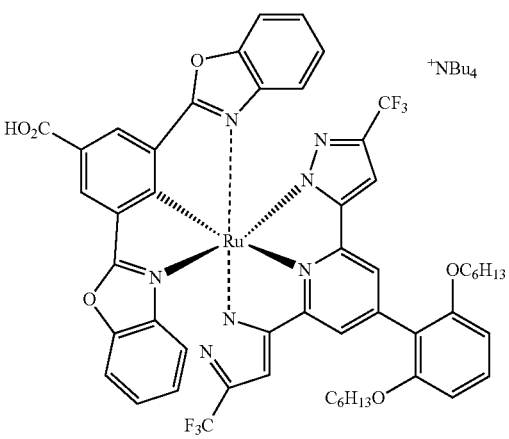

In the above, "Bu" represents a butyl group, and "$^tBu$" represents a t-butyl group, The metal complex dye of the present invention can be readily synthesized according to a method described in JP-A-2001-291534 ("JP-A" means unexamined published Japanese patent application) and a method that is cited in the Japanese patent publication, or according to the methods described in Chem. Commun., 2009, 5844 to 5846, the Non-Patent Literature 1.

The maximum absorption wavelength in a solution of the metal complex dye of the present invention is preferably from 300 to 1,000 nm, more preferably from 350 to 950 nm, and particularly preferably from 370 to 900 nm.

In the present invention, the metal complex dye of the present invention and another dye may be used in combination.

The dye to be used in combination includes: Ru complex dyes disclosed, for example, in each publication or specification of Japanese Patent No. 3731752, JP-T-2002-512729, JP-A-2001-59062, JP-A-2001-6760, Japanese Patent No. 3430254, JP-A-2003-212851, WO 2007/91525, JP-A-2001-291534, and Japanese patent application No. 2010-127308; squaryrium cyanine dyes described in each publication of JP-A-H11-214730, JP-A-2012-144688, JP-A-2012-84503, or the like; organic dyes described in each publication or specification of JP-A-2004-063274, JP-A-2005-123033, JP-A-2007-287694, JP-A-2008-71648, JP-A-2007-287694, and WO 2007/119525; porphyrine dyes described in Angew. Chem. Int. Ed., 49, 1 to 5 (2010), or the like; and phthalo-cyanine dyes described in Angew. Chem. Int. Ed., 46, 8358 (2007), or the like. Preferable dyes to be used in combination include Ru complex dyes, squaryrium cyanine dyes, or organic dyes.

In a case where the metal complex dye of the present invention and another dye are used in combination, a ratio of mass of the metal complex dye of the present invention/mass of another dye is preferably from 95/5 to 10/90, more preferably from 95/5 to 50/50, still more preferably from 95/5 to 60/40, particularly preferably from 95/5 to 65/35, and most preferably from 95/5 to 70/30.

[Photoelectric Conversion Element and Dye-Sensitized Solar Cell]

In the photoelectric conversion element (for example, a photoelectric conversion element 10) and the dye-sensitized solar cell (for example, photoelectrochemical cells 20, 50) according to the present invention, at least the metal complex dye of the present invention is used.

Figure 1:
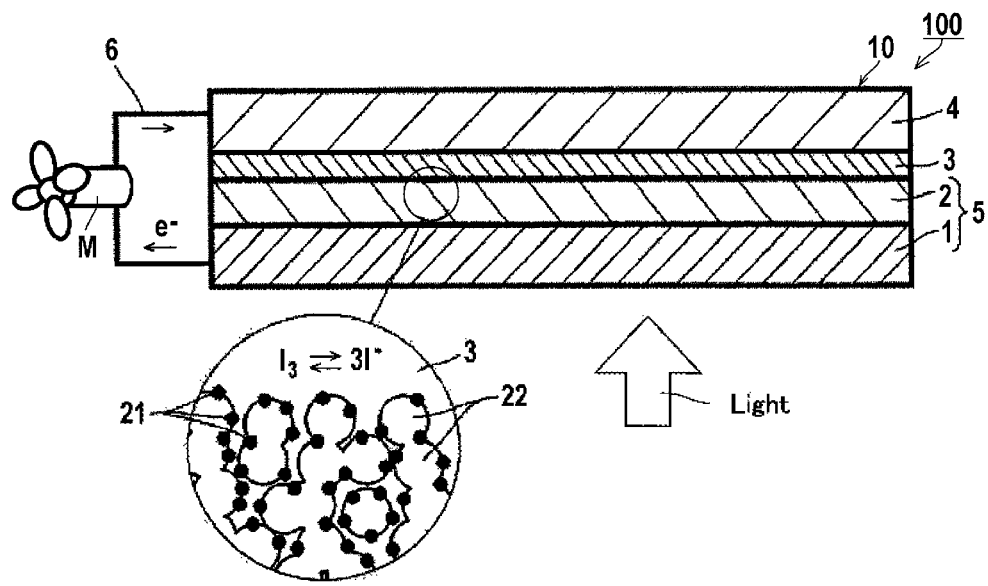
FIG. 1 is a cross-sectional view schematically showing one embodiment of the photoelectric conversion element of the present invention, including an enlarged view of a circular portion in the layer thereof.

In the photoelectric conversion element of the present invention, for example, as shown in FIG. 1, the photoelectric conversion element 10 is composed of: an electrically-conductive support 1; a photoconductor layer 2 containing semiconductor fine-particles which has been sensitized by a dye (metal complex dye) 21; a charge-transfer layer 3 which is a hole-transport layer, and a counter electrode 4. In the present invention, it is preferred that a co-adsorbent has been adsorbed, together with the dye (metal complex dye) 21, onto semiconductor fine-particles 22. The electrically-conductive support 1 having the photoconductor layer 2 provided thereon acts as a working electrode in the photoelectric conversion element 10. In this embodiment, the photoelectric conversion element 10 is shown as a system 100, utilizing a dye-sensitized solar cell which enables the photoelectric conversion element 10 to use in a cell purpose which lets an operation means M to work with an external circuit 6.

In this embodiment, the light-receiving electrode 5 is an electrode comprising an electrically-conductive support 1; and a photoconductor layer 2 containing semiconductor fine-particles 22 to which a dye (metal complex dye) 21 has been adsorbed. In this embodiment, the light-receiving electrode 5 is shown in a manner that may contain an electrolyte, but the electrolyte may not be always contained. The photoconductor layer 2 is designed according to the intended purpose, and it may have a single-layer structure or a multilayer structure. The dye (metal complex dye) 21 in at least one of the photoconductor layers may be a single species or a mixture, as long as at least one of them uses the metal complex dye of the present invention. A light incident to the photoconductor layer 2 excites the dye (metal complex dye) 21. The excited dye has electrons with high energy, and these electrons are transported from the dye (metal complex dye) 21 to the conduction band of the semiconductor fine-particles 22, and further reach the electrically-conductive support 1 by diffusion. At this time, the dye (metal complex dye) 21 is in an oxide form. The electrons on the electrode, while working with the external circuit 6, return to the photoconductor layer 2 in which an oxide form of the dye (metal complex dye) 21 exists (preferably an electrolyte coexists together with the oxide form), through a counter electrode 4, whereby this works as a solar cell.

—Charge Transfer Layer—

The charge transfer layer for use in the photoelectric conversion element of the present invention is a layer having a function to replenish electrons to the oxide form of the dye, and it is provided between the light-receiving electrode and the counter electrode (an opposite electrode). Representative examples thereof include a liquid electrolyte having a redox pair dissolved in an organic solvent, a so-called gel electrolyte in which a liquid having a redox pair dissolved in an organic solvent is impregnated in a polymer matrix, and a molten salt containing a redox pair. In order to enhance efficiency of the charge transfer, a liquid electrolyte is preferred. As a solvent of the liquid electrolyte, a nitrile compound, an ether compound, an ester compound, or the like, is used, and a nitrile compound is preferred, and acetonitrile and methoxypropionitrile are particularly preferred.

Examples of the redox pair include a combination of iodine and an iodide (preferably an iodide salt, or an iodide ionic liquid; more preferably lithium iodide, tetrabutylammonium iodide, tetrapropylammonium iodide, or methylpropylimidazolium iodide), a combination of an alkylviologen (for example, methylviologen chloride, hexylviologen bromide, or benzylviologen tetrafluoroborate) and a reductant thereof, a combination of a polyhydroxybenzene (for example, hydroquinone, naphthohydroquinone, or the like) and an oxidant thereof, a combination of a divalent iron complex and a trivalent iron complex (for example, a combination of potassium ferricyanide and potassium ferrocyanide), and a combination of a divalent cobalt complex and a trivalent cobalt complex. Among these, a combination of iodine and an iodide, and a combination of a divalent cobalt complex and a trivalent cobalt complex, are preferred.

The redox pair acts as an electron carrier. A preferable concentration thereof in total is 0.01 mole/l or more, more preferably 0.1 mole/l or more, and particularly preferably 0.3 mole/l or more. The upper limit of this is not particularly limited, and generally about 5 mole/l.

The cobalt complex is preferably a complex represented by formula (CC).

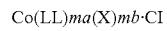

Formula (CC)

In formula (CC), LL represents a bidentate or terdentate ligand. X represents a monodentate ligand. ma represents an integer of 0 to 3. mb represents an integer of 0 to 6. CI represents a counter ion in the case where the counter ion is necessary to neutralize a charge in formula (CC).

Examples of CI include those of CI in formula (I).

LL is preferably a ligand represented by formula (LC).

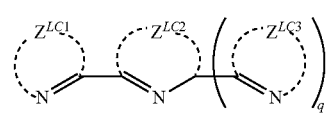

Formula (LC)

In formula (LC), $Z^{LC1}$, $Z^{LC2}$ and $Z^{LC3}$ each independently represent a group of atoms for forming a 5- or 6-membered ring. Each of $Z^{LC1}$, $Z^{LC2}$ and $Z^{LC3}$ may have a substituent, and may form a ring-closure together with an adjacent ring through a substituent. q represents 0 or 1. Examples of the substituent include the substituent T described below.

X is preferably a halogen ion.

The ligand represented by formula (LC) is preferably a ligand represented by any one of formulas (LC-1) to (LC-3).

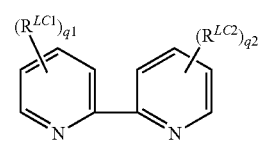

Formula (LC-1)

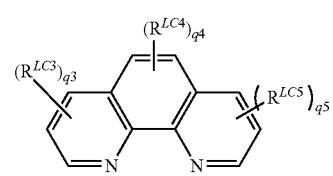

Formula (LC-2)

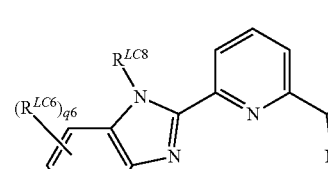

Formula (LC-3)

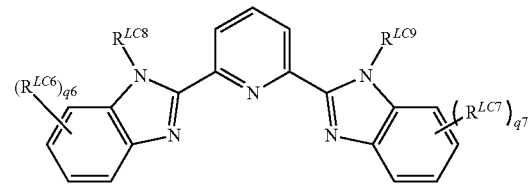

In formulas (LC-1) to (LC-3), $R^{LC1}$ to $R^{LC9}$ each represent a substituent. q1, q2, q6 and q7 each independently represent an integer of 0 to 4. q3 and q5 each independently represent an integer of 0 to 3. q4 represents an integer of 0 to 2.

In formulas (LC-1) to (LC-3), examples of the substituent $R^{LC1}$ to $R^{LC9}$ include an aliphatic group, an aromatic group, a heterocyclic group or the like. Specific examples of the substituent include an alkyl group, an alkoxy group, an alkylthio group, an aryl group, an aryloxy group, an arylthio group, and a heterocyclic ring. Preferred examples include an alkyl group (for example, methyl, ethyl, n-butyl, n-hexyl, isobutyl, sec-butyl, t-butyl, n-dodecyl, cyclohexyl, or benzyl), an aryl group (for example, phenyl, tolyl, or naphthyl), an alkoxy group (for example, methoxy, ethoxy, isopropoxy, or butoxy), an alkylthio group (for example, methylthio, n-butylthio, n-hexylthio, or 2-ethylhexylthio), an aryloxy group (for example, phenoxy, or naphthoxy), an arylthio group (for example, phenylthio, or naphthylthio), and a heterocyclic group (for example, 2-thienyl, or 2-furyl).

Specific examples of the cobalt complex represented by formula (LC) include the followings.

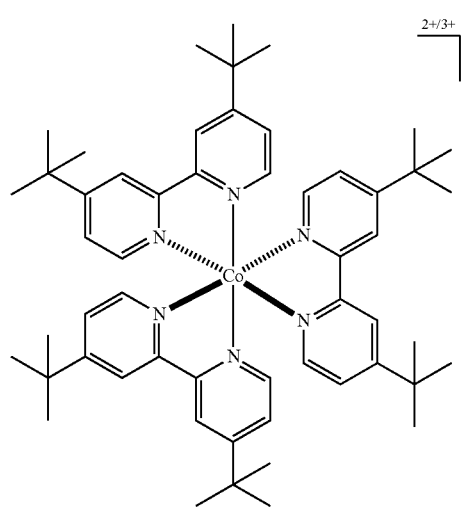

LL-1

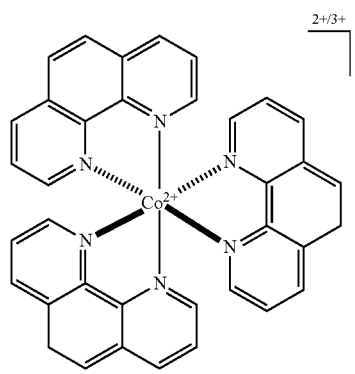

LL-2

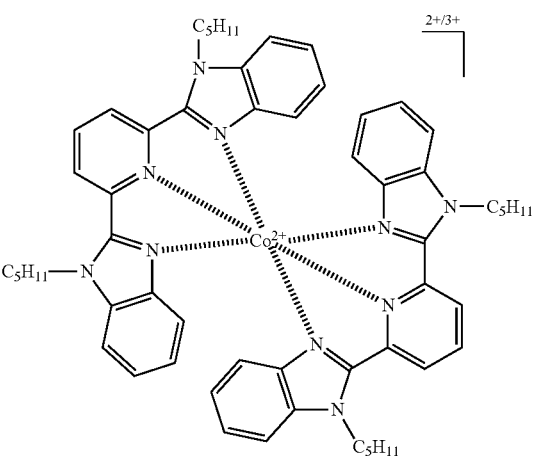

LL-3

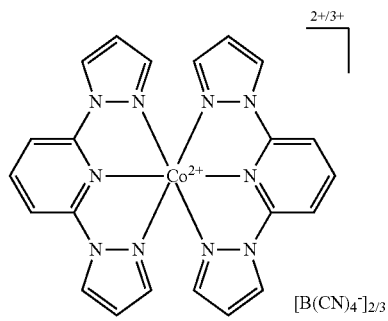

LL-4

In the case where iodine and an iodide are used in combination, as an electrolyte, it is preferred that a 5- or 6-membered-ring nitrogen-containing aromatic cation iodide salt is additionally used in combination with them. Especially, in the case where the ligand represented by formula (A) is not an iodide salt, the ligand is preferably used in combination with an iodide salt of pyridinium salts, imidazolium salts, triazolium salts or the like, as described in Japanese re-publication of WO95/18456, JP-A-8-259543, Denki Kagaku (Electrochemistry), Vol. 65, No. 11, page 923 (1997), and the like.

A solid charge-transport system, such as a p-type semiconductor or a hole-transporting material, may also be used, instead of the liquid electrolyte, and the like. For a solid charge-transport layer, an organic hole-transporting material may be used.

—Co-Adsorbent—

In the photoelectric conversion element of the present invention, a co-adsorbent is preferably used in combination with the metal complex dye of the present invention or another dye to be used if necessary. As such a co-adsorbent, a co-adsorbent having at least one acidic group (preferably a carboxyl group or a salt thereof) is preferable, and examples of the co-adsorbent include a fatty acid and a compound having a steroid skeleton. The fatty acid may be a saturated fatty acid or an unsaturated fatty acid. Examples thereof include a butanoic acid, a hexanoic acid, an octanoic acid, a decanoic acid, a hexadecanoic acid, a dodecanoic acid, a palmitic acid, a stearic acid, an oleic acid, a linoleic acid, and a linolenic acid.

Examples of the compound having a steroid skeleton include a cholic acid, a glycocholic acid, a chenodeoxycholic acid, a hyocholic acid, a deoxycholic acid, a lithocholic acid, and ursodeoxycholic acid. Among these, a cholic acid, a deoxycholic acid, and a chenodeoxycholic acid are preferable; and a chenodeoxycholic acid is further preferable.

A preferred co-adsorbent is a compound represented by formula (CA).

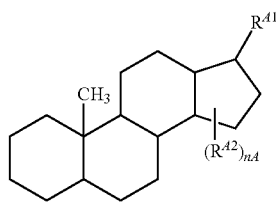

Formula (CA)

In formula (CA), $R^{41}$ represents a substituent having an acidic group. $R^{42}$ represents a substituent. nA represents an integer of 0 or more.

The acidic group has the same meaning as described above.

nA is preferably from 2 to 4.

Examples of the specific compounds include a compound that is exemplified as the compound having a steroid skeleton.

By adsorbing on the semiconductor fine-particles, the co-adsorbent that can be used in the present invention exhibits an effect on suppressing the inefficient association of the dye, and preventing reverse electron transfer from the semiconductor fine-particle surface to the redox system in the electrolyte. An amount to be used of the co-adsorbent is not particularly limited, and it is preferred, from the viewpoint of exhibiting effectively the effects, that the amount is preferably from 1 to 200 moles, more preferably from 10 to 150 moles, and particularly preferably from 20 to 50 moles, with respect to 1 mole of a total of dyes to be used including the metal complex dye.

<Substituent T>

The specification uses an expression "compound" (including complex and dye) to mean, in addition to the compound itself, its salts, and its ion. Further, a substituent with which substitution or non-substitution is not explicitly described in the present specification (the same applies to a linking group and a ligand), means that the substituent may have an arbitrary substituent. The same is also true on a compound with which substitution or non-substitution is not explicitly described. Preferable examples of the substituent include the following substituent T.

In the present specification, the simple description only as a "substituent" means to refer to this substituent T. Further, in a case where each of the substituents, for example, like an alkyl group, is described in a simplistic form, both a preferable range and specific examples for the corresponding group of the substituent T are applied to.

The substituent T includes the followings:
an alkyl group (preferably an alkyl group having 1 to 20 carbon atoms, e.g. methyl, ethyl, isopropyl, t-butyl, pentyl, heptyl, 1-ethylpentyl, benzyl, 2-ethoxyethyl, 1-carboxymethyl, or trifluoromethyl), an alkenyl group (preferably an alkenyl group having 2 to 20 carbon atoms, e.g. vinyl, allyl, or oleyl), an alkynyl group (preferably an alkynyl group having 2 to 20 carbon atoms, e.g. ethynyl, butadiynyl, or phenylethynyl), a cycloalkyl group (preferably a cycloalkyl group having 3 to 20 carbon atoms, e.g. cyclopropyl, cyclopentyl, cyclohexyl, or 4-methylcyclohexyl), an cycloalkenyl group (preferably a cycloalkenyl group having 5 to 20 carbon atoms, e.g. cyclopentenyl, or cyclohexenyl), an aryl group (preferably an aryl group having 6 to 26 carbon atoms, e.g. phenyl, 1-naphthyl, 4-methoxyphenyl, 2-chlorophenyl, or 3-methylphenyl), a heterocyclic group (preferably a 5- or 6-membered heterocyclic group having 2 to 20 carbon atoms and at least one oxygen atom, sulfur atom, or nitrogen atom, e.g. 2-pyridyl, 4-pyridyl, 2-imidazolyl, 2-benzimidazolyl, 2-thiazolyl, or 2-oxazolyl), an alkoxy group (preferably an alkoxy group having 1 to 20 carbon atoms, e.g. methoxy, ethoxy, isopropyloxy, or benzyloxy), an alkenyloxy group (preferably an alkenyloxy group having 2 to 20 carbon atoms, e.g. vinyloxy or allyloxy), an alkynyloxy group (preferably an alkynyloxy group having 2 to 20 carbon atoms, e.g. 2-propenyloxy or 4-butynyloxy), a cycloalkyloxy group (preferably a cycloalkyloxy group having 3 to 20 carbon atoms, e.g. cyclopropyloxy, cyclopentyloxy, cyclohexyloxy, or 4-methylcyclohexyloxy), an aryloxy group (preferably an aryloxy group having 6 to 26 carbon atoms, e.g. phenoxy, 1-naphthyloxy, 3-methylphenoxy, or 4-methoxyphenoxy), a heterocyclic oxy group (e.g. imidazolyloxy, benzoimidazolyloxy, thiazolyloxy, benzothiazolyloxy, triazinyloxy, or purinyloxy);

an alkoxycarbonyl group (preferably an alkoxycarbonyl group having 2 to 20 carbon atoms, e.g. ethoxycarbonyl, or 2-ethylhexyloxycarbonyl), a cycloalkoxycarbonyl group (preferably a cycloalkoxycarbonyl group having 4 to 20 carbon atoms, e.g. cyclopropyloxycarbonyl, cyclopentyloxycarbonyl, or cyclohexyloxycarbonyl), an aryloxycarbonyl group (preferably an aryloxycarbonyl group having 6 to 20 carbon atoms, e.g. phenyloxycarbonyl, or naphthyloxycarbonyl), an amino group (preferably an amino group having 0 to 20 carbon atoms including an alkylamino group, an alkenylamino group, an alkynylamino group, a cycloalkylamino group, a cycloalkenylamino group, an arylamino group, and a heterocyclic amino group, e.g. amino, N,N-dimethylamino, N,N-diethylamino, N-ethylamino, N-allylamino, N-(2-propinyl)amino, N-cyclohexylamino, N-cyclohexenylamino, anilino, pyridylamino, imidazolylamino, benzimidazolylamino, thiazolylamino, benzothiazolylamino, or triazinylamino), a sulfamoyl group (preferably a sulfamoyl group having 0 to 20 carbon atoms, preferably an alkyl-, cycloalkyl-, or aryl-sulfamoyl group, e.g. N,N-dimethylsulfamoyl, N-cyclohexylsulfamoyl, or N-phenylsulfamoyl), an acyl group (preferably an acyl group having 1 to 20 carbon atoms, e.g. acetyl, cyclohexylcarbonyl, or benzoyl), an acyloxy group (preferably an acyloxy group having 1 to 20 carbon atoms, e.g. acetyloxy, cyclohexylcarbonyloxy, or benzoyloxy), a carbamoyl group (preferably a carbamoyl group having 1 to 20 carbon atoms, preferably an alkyl-, cycloalkyl-, or aryl-carbamoyl group, e.g. N,N-dimethylcarbamoyl, N-cyclohexylcarbamoyl, or N-phenylcarbamoyl), an acylamino group (preferably an acylamino group having 1 to 20 carbon atoms, e.g. acetylamino, cyclohexylcarbonylamino, or benzoylamino), a sulfonamide group (preferably a sulfonamide group having 0 to 20 carbon atoms, preferably an alkyl-, cycloalkyl-, or aryl-sulfonamide group, e.g. methane sulfonamide, benzene sulfonamide, N-methyl methane sulfonamide, N-cyclohexyl sulfonamide, or N-ethyl benzene sulfonamide), an alkylthio group (preferably an alkylthio group having 1 to 20 carbon atoms, e.g. methylthio, ethylthio, isopropylthio, or benzylthio), a cycloalkylthio group (preferably a cycloalkylthio group having 3 to 20 carbon atoms, e.g. cyclopropylthio, cyclopentylthio, cyclohexylthio, or 4-methylcyclohexylthio), an arylthio group (preferably an arylthio group having 6 to 26 carbon atoms, e.g. phenylthio, 1-naphthylthio, 3-methylphenylthio, or 4-methoxyphenylthio), an alkyl-, cycloalkyl-, or aryl-sulfonyl group (preferably a sulfonyl group having 1 to 20 carbon atoms, e.g. methylsulfonyl, ethylsulfonyl, cyclohexylsulfonyl, or benzene sulfonyl), a silyl group (preferably a silyl group having 1 to 20 carbon atoms, preferably an alkyl-, aryl-, alkoxy-, or aryloxy-substituted silyl group, e.g. triethylsilyl, triphenylsilyl, diethylbenzylsilyl, or dimethylphenylsilyl), a silyloxy group (preferably a silyloxy group having 1 to 20 carbon atoms, preferably an alkyl-, aryl-, alkoxy-, or aryloxy-substituted silyloxy group, e.g. triethylsilyloxy, triphenylsilyloxy, diethylbenzylsilyloxy, or dimethylphenylsilyloxy), a hydroxyl group, a cyano group, a nitro group, a halogen atom (e.g. fluorine, chlorine, bromine, or iodine atom), a carboxyl group, a sulfo group, a phosphonyl group, a phosphoryl group, and a boric-acid group; more preferably an alkyl group, an alkenyl group, a cycloalkyl group, an aryl group, a heterocyclic group, an alkoxy group, a cycloalkoxy group, an aryloxy group, an alkoxycarbonyl group, a cycloalkoxycarbonyl group, the above-described amino group, an acyamino group, a cyano group, or a halogen atom; and particularly preferably an alkyl group, an alkenyl group, a heterocyclic group, an alkoxy group, an alkoxycarbonyl group, an amino group, an acylamino group, or a cyano group.

When the compound or the substituent or the like contains an alkyl group or an alkenyl group, these may be a straight chain or a branched chain, and these may be substituted or unsubstituted. Further, in the case of containing an aryl group, a heterocyclic group or the like, these may be a single ring or a condensed ring, and may be substituted or unsubstituted.

<<Photoelectric Conversion Element and Dye-Sensitized Solar Cell>>

In the present invention, regarding materials for use in a photoelectric conversion element and a dye-sensitized solar cell, and a method of producing each member, a photoelectric conversion element and a dye-sensitized solar cell can be produced according to a usual manner, and the materials and methods may be referred to, for example, U.S. Pat. No. 4,927,721, U.S. Pat. No. 4,684,537, U.S. Pat. No. 5,084,365, U.S. Pat. No. 5,350,644, U.S. Pat. No. 5,463,057, U.S. Pat. No. 5,525,440, JP-A-7-249790, JP-A-2004-220974, and JP-A-2008-135197.

Hereinafter, principal materials and members are described appropriately.

The electrically-conductive support is preferably a support having electroconductivity per se, such as a metal, or a support of glass or plastic having an electrically-conductive layer on the surface. In addition to the glass and plastic, ceramic (JP-A-2005-135902), an electrically-conductive resin (JP-A-2001-160425) or the like may be used as the support. The support may be provided with a light management function at the surface, and for example, the antireflective film having a high refractive index film and a low refractive index oxide film alternately laminated as described in JP-A-2003-123859, and the light guide function as described in JP-A-2002-260746 may be mentioned.

The thickness of the electrically-conductive layer is preferably 0.01 to 30 µm, more preferably 0.03 to 25 µm, and particularly preferably 0.05 to 20 µm.

It is preferable that the electrically-conductive support is substantially transparent. The terms "substantially transparent" means that the transmittance of light is 10% or more, preferably 50% or more, particularly preferably 80% or more. As the transparent electrically-conductive support, a support formed from glass or plastic and coated with an electrically-conductive metal oxide is preferable. In this case, the amount of coating of the electrically-conductive metal oxide is preferably 0.1 to 100 g, per square meter of the support made of glass or plastic. In the case of using a transparent electrically-conductive support, it is preferable that light is incident from the support side.

Regarding the semiconductor fine-particles, fine-particles of chalcogenides of metals (for example, oxides, sulfides and selenides), or fine-particles of perovskites may be used with preference. Preferred examples of the chalcogenides of metals include oxides of titanium, tin, zinc, tungsten, zirconium, hafnium, strontium, indium, cerium, yttrium, lanthanum, vanadium, niobium or tantalum, cadmium sulfide, and cadmium selenide. Preferred examples of the perovskites include strontium titanate, and calcium titanate. Among these, titanium oxide, zinc oxide, tin oxide, and tungsten oxide are particularly preferred.

Examples of the crystal structure of titania include structures of anatase type, brookite type and rutile type, and anatase type and brookite type structures are preferred. A titania nanotube/nanowire/nanorod may be mixed with titania fine-particles or may be used as a semiconductor electrode.

A particle size of the semiconductor fine-particles is expressed in terms of an average particle size using a diameter when a projected area is converted into a circle, and is preferably 0.001 to 1 µm as primary particles, and 0.01 to 100 µm as an average particle size of dispersions. Examples of the method for coating the semiconductor fine-particles on the electrically-conductive support include a wet method, a dry method or other methods.

It is preferable to form a short circuit-preventing layer between the transparent electrically-conductive film and the photoconductor layer (which is a layer containing semiconductor fine-particles, and also referred to as "semiconductor layer" or "semiconductor fine-particle layer"), so as to prevent reverse current due to a direct contact between the electrolyte liquid and the electrode. It is preferable to employ a spacer or a separator, so as to prevent contact between the light-receiving electrode and the counter electrode. It is preferable for the semiconductor fine-particles to have a large surface area, so that a large amount of dye can adsorb to the surface. For example, while the semiconductor fine-particles have been coated on the support, the surface area is preferably 10 times or more, and more preferably 100 times or more, relative to the projected surface area. The upper limit of this value is not particularly limited, and the upper limit is generally about 5,000 times. In general, as the thickness of the semiconductor fine-particle layer increases, the amount of dye that can be supported per unit area increases, and therefore, the light absorption efficiency is increased. However, since the diffusion distance of generated electrons increases along, the loss due to charge recombination is also increased. Although a preferred thickness of the photoconductor layer containing semiconductor fine-particles may vary with the utility of the element, the thickness is typically 0.1 to 100 µm. In the case of using the photoelectric conversion element for a dye-sensitized solar cell, the thickness of the semiconductor fine-particle layer is preferably 1 to 50 µm, and more preferably 3 to 30 µm. The semiconductor fine-particles may be calcined after being applied on the support, at a temperature of 100 to 800° C. for 10 minutes to 10 hours, so as to bring about cohesion of the particles. When a glass support is used, the film-forming temperature is preferably 400 to 60° C.

The amount of coating of the semiconductor fine-particles per square meter of the support is preferably 0.5 to 500 g, and more preferably 5 to 100 g. The overall amount of use of the dye is preferably 0.01 to 100 millimoles, more preferably 0.1 to 50 millimoles, and particularly preferably 0.1 to 10 millimoles, per square meter of the support. In this case, the amount of use of the metal complex dye of the present invention is preferably set to 5% by mole or more. The amount of the dye adsorbed to the semiconductor fine-particles is preferably 0.001 to 1 millimole, and more preferably 0.1 to 0.5 millimoles, based on 1 g of the semiconductor fine-particles. When the amount of the dye is set to such a range, the sensitization effect can be sufficiently obtained.

When the dye is a salt, a counter ion of this dye is not particularly limited. Examples thereof include an alkali metal ion and a quaternary ammonium ion.

After the dye has been adsorbed, the surface of the semiconductor fine-particles may be treated using amines.

Preferred examples of the amines include pyridines (e.g., 4-tert-butylpyridine, and polyvinylpyridine). These may be used directly when the compounds are liquids, or may be used in a state of being dissolved in an organic solvent.

The counter electrode is preferably an electrode working as a positive electrode in the dye-sensitized solar cell (photoelectrochemical cell). The counter electrode usually has the same meaning as the electrically-conductive support described above, but in a construction which is likely to maintain a sufficient strength, a support is not necessarily required. A preferred structure of the counter electrode is a structure having a high charge collecting effect. At least one of the electrically-conductive support and the counter electrode as mentioned above should be substantially transparent, in order for light to reach the photoconductor layer. In the dye-sensitized solar cell of the present invention, the electrically-conductive support is preferably transparent to allow sunlight to inject from the support side. In this case, the counter electrode has further preferably properties of reflecting light. As the counter electrode of the dye-sensitized solar cell, a glass or plastic plate on which a metal or an electrically-conductive oxide is deposited is preferable, and a glass plate on which platinum is deposited is particularly preferable. In the dye-sensitized solar cell, a lateral side of the cell is preferably sealed with a polymer, an adhesive, or the like, in order to prevent evaporation of the component.

The present invention can be applied to the photoelectric conversion elements and the dye-sensitized solar cells described, for example, in Japanese Patent No. 4260494, JP-A-2004-146425, JP-A-2000-340269, JP-A-2002-289274, JP-A-2004-152613, JP-A-9-27352. In addition, the present invention can be applied to the photoelectric conversion elements and the dye-sensitized solar cells described, for example, in JP-A-2004-152613, JP-A-2000-90989, JP-A-2003-217688, JP-A-2002-367686, JP-A-2003-323818, JP-A-2001-43907, JP-A-2000-340269, JP-A-2005-85500, JP-A-2004-273272, JP-A-2000-323190, JP-A-2000-228234, JP-A-2001-266963, JP-A-2001-185244, JP-T-2001-525108 (the term "JP-T" means a published Japanese translation of a PCT patent application), JP-A-2001-203377, JP-A-2000-100483, JP-A-2001-210390, JP-A-2002-280587, JP-A-2001-273937, JP-A-2000-285977, JP-A-2001-320068.

<<Dye Solution, Semiconductor Electrode Using the Same, and Production Method of Dye-Sensitized Solar Cell>>

In the present invention, the dye-adsorbed electrode is preferably produced using a dye solution containing the metal complex dye of the present invention.

In the foregoing dye solution, the metal complex dye of the present invention is dissolved in a solvent, and a co-adsorbebt and other ingredients may be contained therein, as needed.

The foregoing solvent includes solvents described in JP-A 2001-291534, but the solvent is not particularly limited thereto. In the present invention, organic solvents are preferred. More preferred are alcohols, amides, nitriles, alcohols, hydrocarbons, and a mixed solvent of two or more kinds of these solvents. As a mixed solvent, preferred are those of alcohols and a solvent selected from amides, nitriles, alcohols, or hydrocarbons. More preferred are mixed solvents of alcohols and amides and mixed solvents of alcohols and hydrocarbons, and particularly preferred are mixed solvents of alcohols and amides.

The dye solution preferably contains a co-adsorbent, and the co-adsorbent is preferably the foregoing ones. Among them, the compound represented by formula (CA) is preferred.

Preferred is the dye solution of the present invention in which a concentration of the metal complex dye and the co-adsorbent have been adjusted so that the dye solution can be used as it is when a photoelectric conversion element or a dye-sensitized solar cell is prepared. In the present invention, the metal complex dye of the present invention is preferably contained in an amount of from 0.001 to 0.1% by mass.

In the dye solution, adjustment of water content is preferred in particular, and thus in the dye solution, it is preferred that the content (content rate) of water is adjusted to the range of from 0 to 0.1% by mass.

Similarly, adjustment of water content of the electrolytic solution in a photoelectric conversion element and a dye-sensitized solar cell is preferred, in order to achieve effectively the effects of the present invention. Thus, it is preferred that the content (content rate) of water in the electrolytic solution is adjusted to the range of from 0 to 0.1% by mass. The foregoing adjustment of the electrolytic solution is preferably carried out with the dye solution in particular.

In the present invention, preferred is a semiconductor electrode for dye-sensitized solar cell in which the metal complex dye derived from the use of the dye solution has been carried on a semiconductor surface provided on the semiconductor electrode.

Further, it is preferred to produce a dye-sensitized solar cell, using the dye solution, thereby having a metal complex dye carried on the semiconductor fine-particle surface provided on the semiconductor electrode.

<<Compounds Useful for Ligand>>

The compound represented by formula (A-3) which is a compound to be incorporated in the metal complex dye represented by formula (I) is useful as a ligand. Especially, the compound represented by formula (A-4') or (A-5') is useful.

In the compound, when $Ar^1$ and $Ar^2$ in formula (A-3) which is a ligand each represent an aromatic group having an anion, the anion has a proton as a counter cation.

Further, a preferred substituent R is that, when a useful compound for the ligand has coordinated to a metal, the maximum linking chain number $N_R$ of linking chain numbers (bond numbers) of a linking chain linking the atom G1 with the atom located at the furthest position through a linkage of the substituent R, is greater than ½ times, more preferably greater than 1 time, of the minimum linking chain number $N_{M\text{-}G1}$ of linking chain numbers (bond numbers) of a linking chain linking from the metal atom M to the atom G1.

The compound represented by formula (A-3) in the present invention can be used also as a ligand for metal complex dyes other than the metal complex dye of the present invention, and also can be used as a ligand for complexes other than metal complex dyes.

EXAMPLES

The present invention will be described in more detail based on examples given below, but the invention is not meant to be limited by these.

Example 1

Synthesis (Preparation) of Metal Complex Dye

Hereinafter, methods of preparing the metal complex dye of the present invention are described in detail. The starting materials, the dye intermediates and the preparation routes are not limited by these.

(Preparation of Exemplified Dye D-8)
Exemplified dye D-8 was prepared according to the method shown in the following scheme.
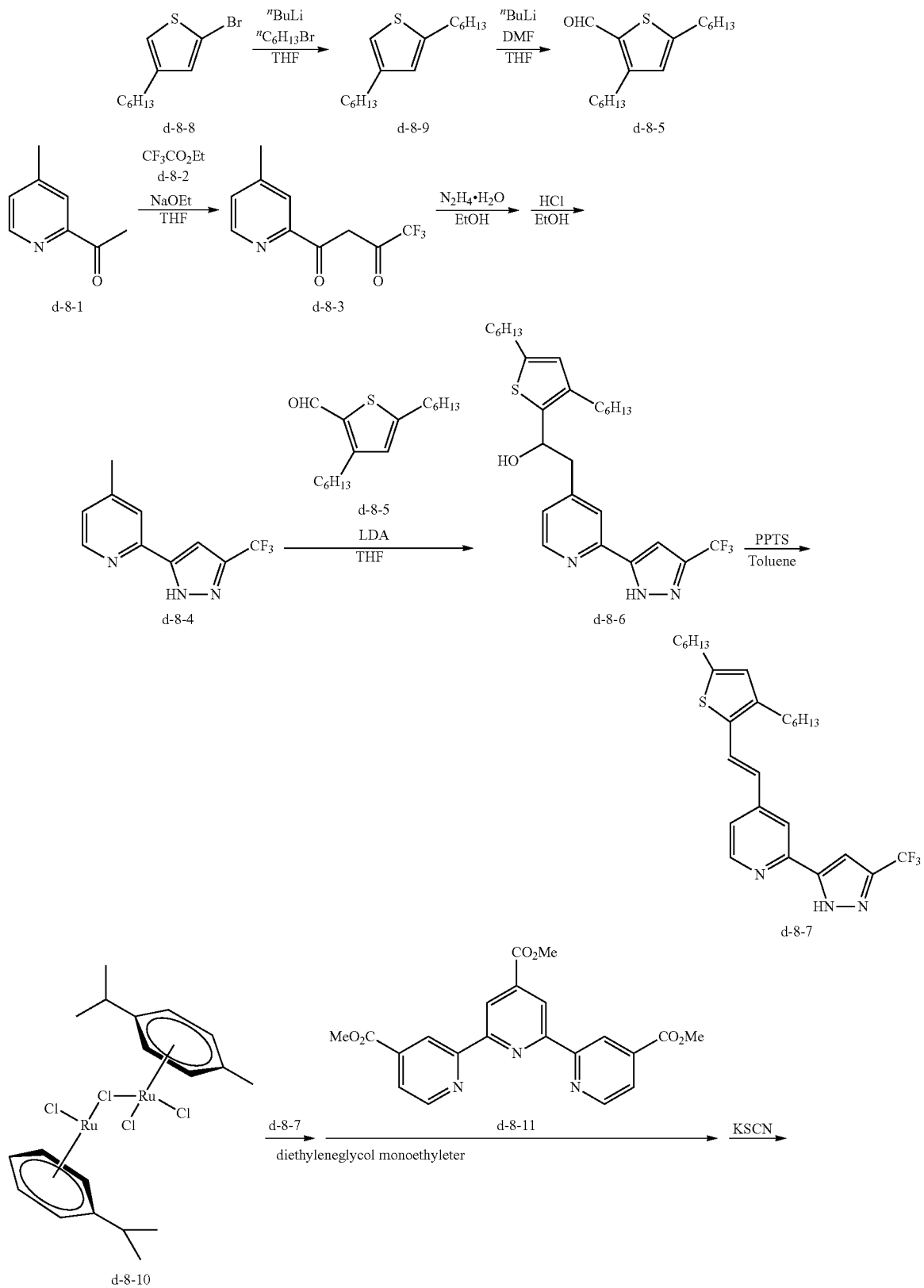

-continued

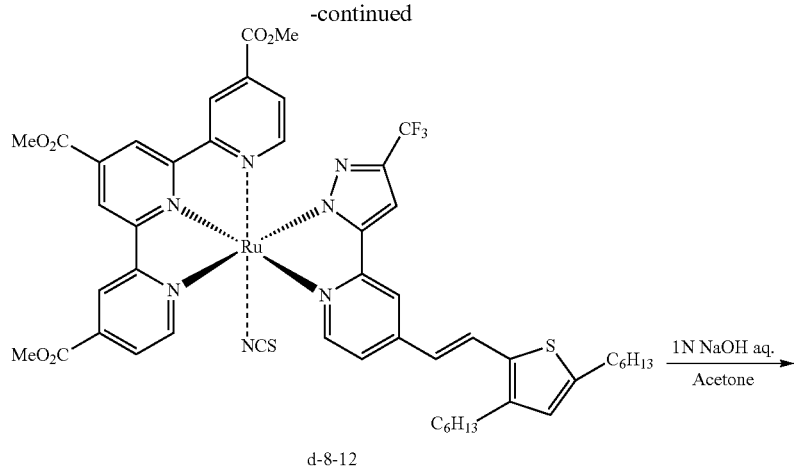

d-8-12

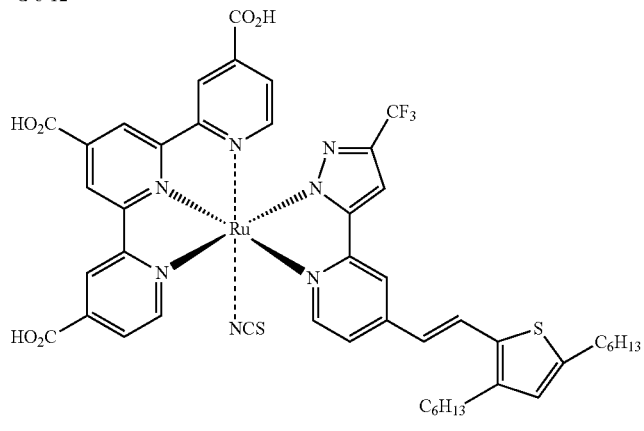

D-8

(i) Preparation of Compound d-8-9

In 200 ml of THF (tetrahydrofuran), 25 g of Compound d-8-8 was dissolved, and 1.05 stoichiometric amounts of a 1.6M hexane solution of buthyl lithium was added thereto, while stirring at −78° C., under a nitrogen atmosphere, followed by stirring for 15 minutes. Then, thereto, a solution of 1.5 stoichiometric amounts of n-hexyl bromide dissolved in 50 ml of THF was added dropwise. After bringing the temperature to 0° C., an ammonium chloride aqueous solution was added dropwise thereto, followed by separation of the liquid, and concentration of the thus-separated organic layer. The thus-obtained crude product was purified by silica gel column chromatography, to give 25.7 g of Compound d-8-9.

(ii) Preparation of Compound d-8-5

In 200 ml of THF (tetrahydrofuran), 25 g of Compound d-8-9 was dissolved, and 1.05 stoichiometric amounts of a 1.6M hexane solution of buthyl lithium was added thereto, while stirring at −15° C., under a nitrogen atmosphere, followed by stirring for 15 minutes. Then, thereto, 1.2 stoichiometric amounts of DMF (N,N-dimethyl folmamide) was added dropwise. After bringing the temperature to 0° C., an ammonium chloride aqueous solution was added dropwise thereto, followed by separation of the liquid, and concentration of the thus-separated organic layer. The thus-obtained crude product was purified by silica gel column chromatography, to give 24.3 g of Compound d-8-5.

(iii) Preparation of Compound d-8-3

In 200 ml of THF (tetrahydrofurane), 25 g of Compound d-8-1 (2-acetyl-4-methylpyridine) was dissolved, and 18.9 g of sodium ethoxide was added thereto, while stirring at 0° C., under a nitrogen atmosphere, followed by stirring for 15 minutes. After that, 28.9 g of Compound d-8-2 (ethyl trifluoroacetate) was added dropwise thereto, followed by stirring for 20 hours at external temperature of 70° C. After returned to room temperature, an ammonium chloride aqueous solution was added dropwise thereto, followed by separation of the liquid and concentration of the thus-obtained organic layer, to give 54.2 g of crude product d-8-3.

(iv) Preparation of Compound d-8-4

In 220 ml of ethanol, 54.2 g of Compound d-8-3 was dissolved, and 5.6 ml of hydrazine monohydrate was added thereto, while stirring at room temperature, under a nitrogen atmosphere, followed by heating for 1 hour at external temperature of 90° C. After that, 5 ml of concentrated hydrochloric acid was added thereto, followed by stirring for 1 hour. After concentration, extraction and separation was conducted with 150 ml of sodium bicarbonate water and 150 ml of ethyl acetate, and then the thus-obtained organic layer was concentrated. After recrystallization from acetonitrile, 23.2 g of Compound d-8-4 was obtained.

(v) Preparation of Compound d-8-6

While stirring 4.1 g of diisopropylamine and 30 ml of tetrahydrofurane at −40° C. under a nitrogen atmosphere, 23.1 ml of a 1.6M n-butyl lithium hexane solution was added dropwise thereto, followed by stirring for 2 hours. After that, 4.0 g of Compound d-8-4 was added thereto, followed by stirring at 0° C. for 80 minutes. Then, a solution containing 3.73 g of Compound d-8-5 dissolved in 15 ml of tetrahydrofurane was added dropwise thereto. After that, the resultant mixture was stirred at 0° C. for 80 minutes, and then stirred at room temperature for 5 hours. Then, an ammonium chloride solution was added thereto, followed by extraction and separation with ethyl acetate. Then, the thus-obtained organic layer was concentrated. After purification using a silica gel column chromatography, 5.8 g of Compound d-8-6 was obtained.

(vi) Preparation of Compound d-8-7

To 50 mL of toluene, 5.0 g of Compound d-8-6 and 5.9 g of PPTS (pyridinium para-toluenesulfonate) were added, and the resultant mixture was heated under reflux for 5 hours under a nitrogen atmosphere. After concentration, the resultant liquid was separated with a saturated aqueous solution of sodium bicarbonate and methylene chloride, and the resultant organic layer was concentrated. The crystal obtained was recrystallized from methanol and methylene chloride, to give 3.9 g of Compound d-8-7.

The structure of Compound d-8-7 obtained was confirmed by MS (mass spectrum) measurement.

MS-ESI m/z=488.2 (M-H)$^+$ (vii) Preparation of Exemplified Dye D-8

To 150 mL of diethylene glycol monoethyl ether, 1.20 g of Compound d-8-10 and 1.62 g of Compound d-8-7 were added, followed by stirring at 70° C. for 3 hours under a nitrogen atmosphere. Then, 1.63 g of Compound d-8-11 was added thereto, followed by stirring under heating at 120° C. for 8 hours. Then, 10.7 g of potassium thiocyanate was added thereto, followed by stirring at 160° C. for 8 hours. After concentration, water was added, followed by filtration. The filtrate was purified by a silica gel column chromatography, followed by adding thereto a mixed solvent of 30 ml of acetone and 40 ml of a 1N sodium hydroxide aqueous solution, and stirring for 4 hours at external temperature of 40° C. After bringing the temperature to room temperature, the pH was adjusted to 3.5 with a trifluoromethane sulfonic acid aqueous solution, and the precipitate was filtrated, to give 3.0 g of crude product.

The resultant crude product was dissolved in a methanol solution together with TBAOH (tetrabutylammonium hydroxide), followed by purification by Sephadex LH-20 column. After a fraction in the main layer was recovered and concentrated, a trifluoromethane sulfonic acid solution was added, to adjust the pH to 3, and the thus-produced precipitate was filtered, to obtain 2.4 g of Exemplified dye D-8.

The structure of Exemplified Dye D-8 obtained was confirmed by MS (mass spectrum) measurement.

MS-ESI m/z=1012.2 (M-H)$^+$

Spectral absorption measurement of the thus-obtained Exemplified dye D-8 was conducted, with UV-visible spectrometer (UV-2400-PC, Shimadzu), with a solution prepared so that concentration of the dye in a 340 μmol/l tetrabutyl ammonium hydroxide methanol solvent was 17 μmol/l. As a result, the maximum absorption wavelength was 521 nm.

(Preparation of Exemplified Dye D-7)

Compound d-7-7 was prepared according to the method shown in the following scheme. Then, Exemplified dye D-7 was prepared in the same manner as Exemplified dye D-8, except that Compound d-8-7 was changed to Compound d-7-7.

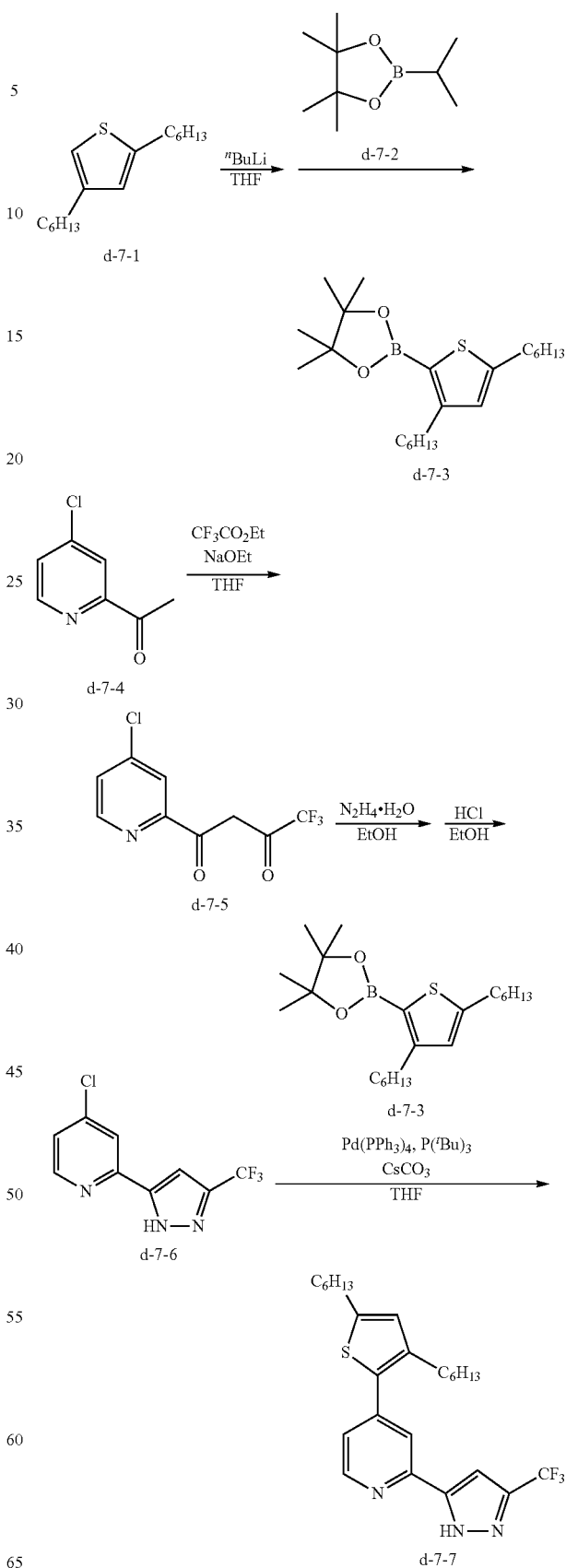

The synthesis was made according to Chemical Communications, 2009, 5844-5846.

(Preparation of Exemplified Dye D-1)

Compound d-1-3 was prepared according to the method shown in the following scheme. Then, Exemplified dye D-1 was prepared in the same manner as Exemplified dye D-7, except that Compound d-7-3 was changed to Compound d-1-3, and potassium thiocyanate was changed to potassium selenocyanate.

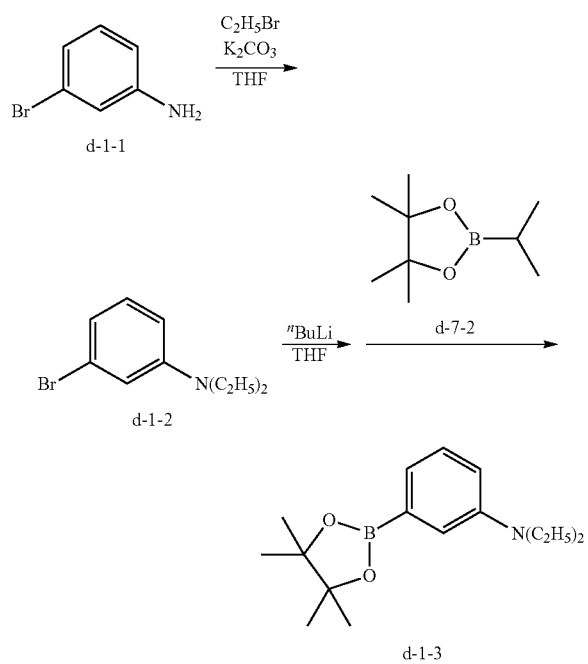

(Preparation of Exemplified Dye D-2)

Compound d-2-3 was prepared according to the method shown in the following scheme. Then, Exemplified dye D-2 was prepared in the same manner as Exemplified dye D-7, except that Compound d-7-3 was changed to Compound d-2-3, and potassium thiocyanate was changed to potassium cyanate.

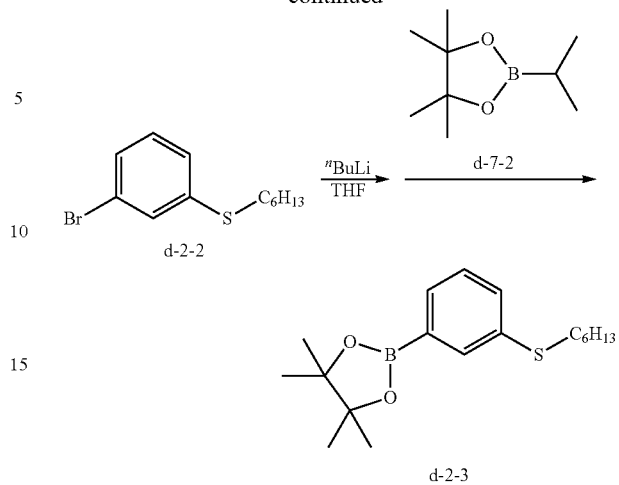

(Preparation of Exemplified Dye D-9)

Compound d-7-7 was prepared in the same manner as in Exemplified dye D-7. Then, Exemplified dye D-9 was prepared in the same manner as Exemplified dye D-8, except that Compound d-8-7 was changed to Compound d-7-7, and Compound d-8-11 was changed to Compound d-9-1.

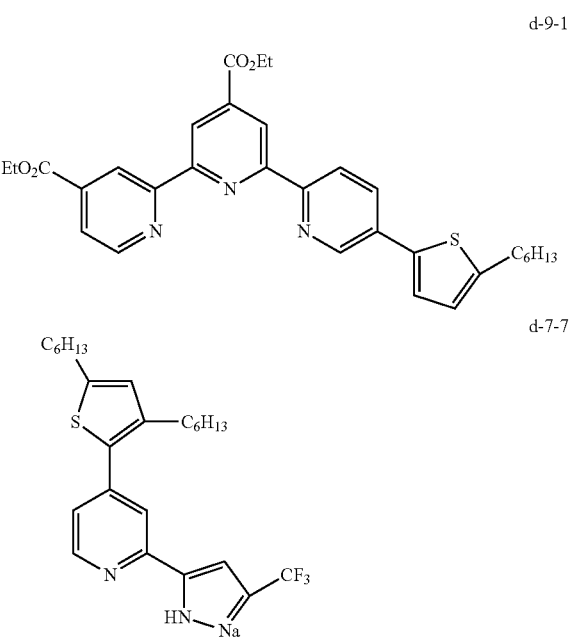

Compound d-9-1 was synthesized referring to Angewandte Chemie International Edition, 50, p. 1-6 (2011).

(Preparation of Exemplified Dye D-15)

Exemplified dye D-15 was prepared according to the method shown in the following scheme.

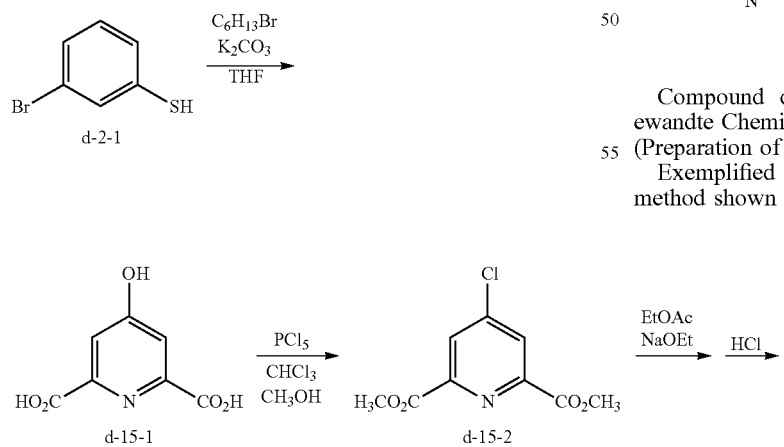
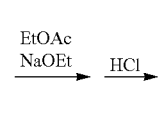

-continued
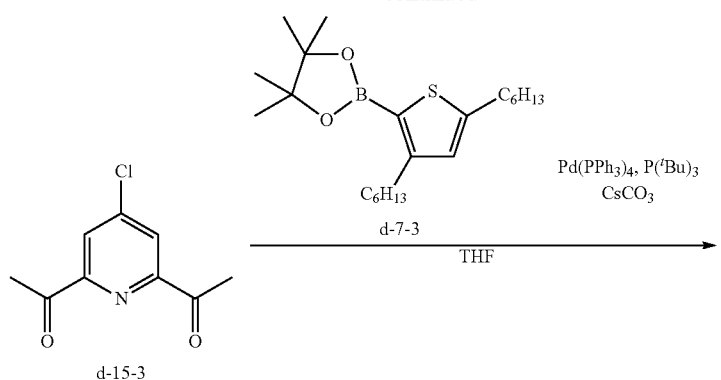
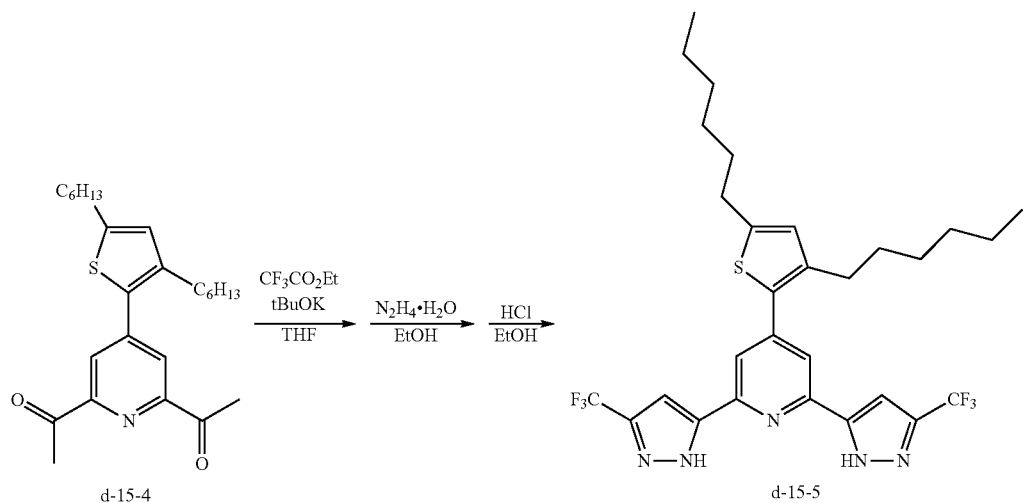
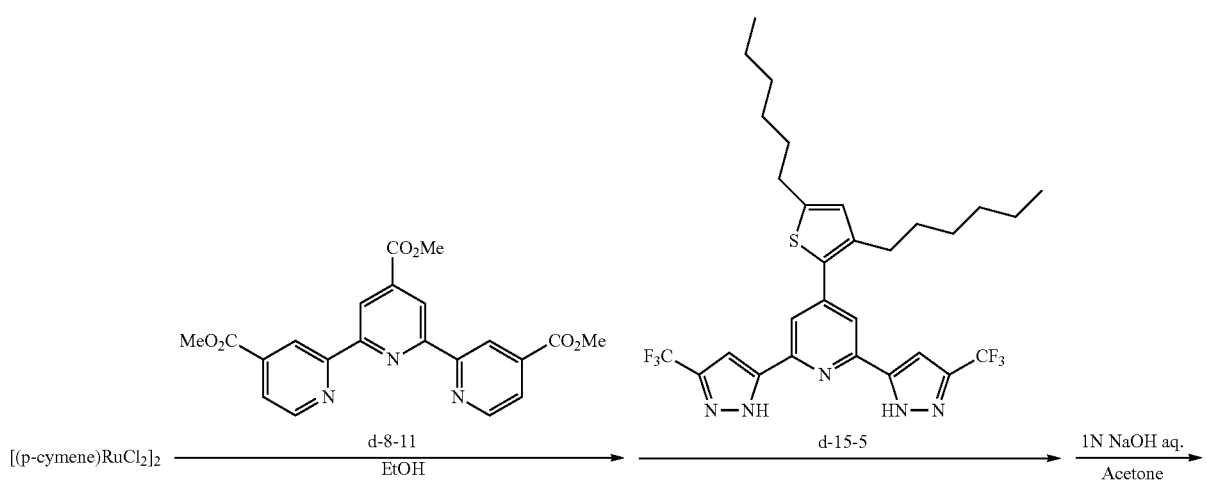

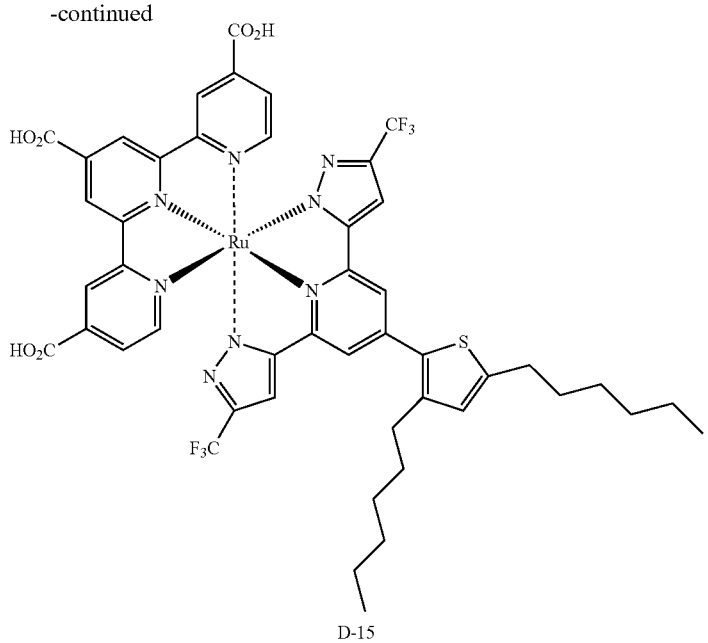
D-15
Exemplified dye D-15 was synthesized referring to Angewandte Chemie International Edition, 50, p. 2054-2058 (2011).
The structure of Compound d-15-5 obtained was confirmed by MS (mass spectrum) measurement.
MS-ESI m/z=596.2 (M-H)$^+$
(Preparation of Exemplified Dye D-12)
Exemplified dye D-12 was prepared according to the method shown in the following scheme.
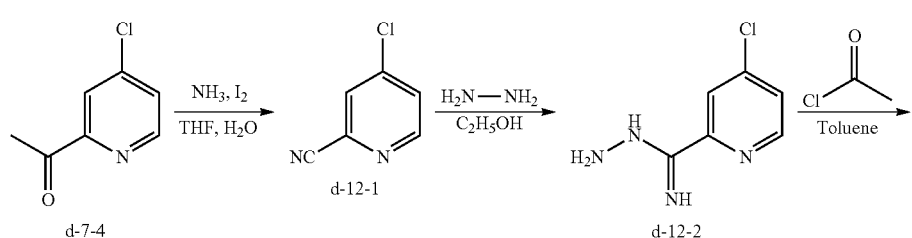
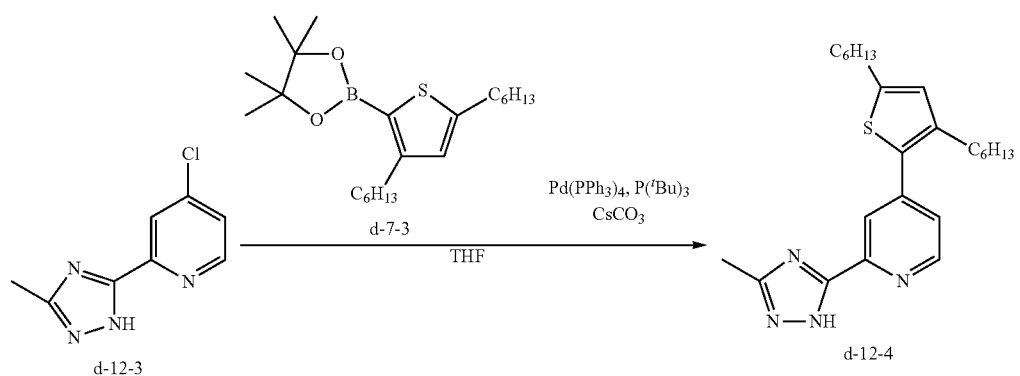

-continued

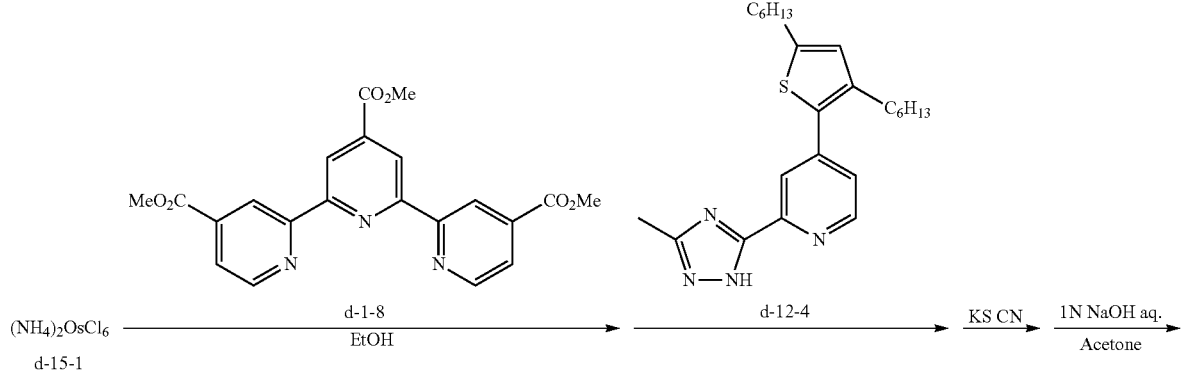

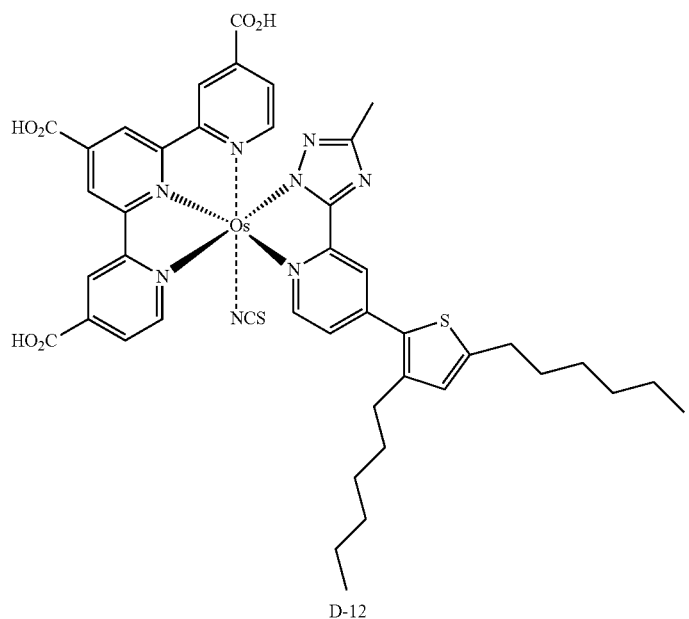

The structure of Compound d-12-4 obtained was confirmed by MS (mass spectrum) measurement.

MS-ESI m/z=409.3 (M-H)$^+$ (Preparation of Exemplified Dye D-13)

Compound d-13-2 was prepared according to the method shown in the following scheme. Then, Exemplified dye D-13 was prepared in the same manner as Exemplified dye D-12, except that Compound d-12-3 was changed to Compound d-13-2.

-continued

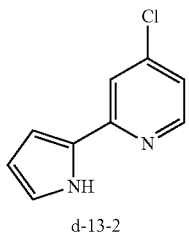

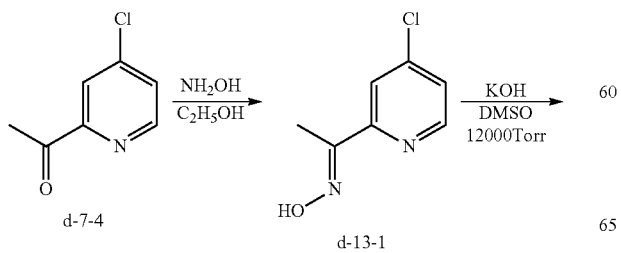

(Preparation of Exemplified Dye D-16)

Compound d-16-2 was prepared according to the method shown in the following scheme. Then, Exemplified dye D-16 was prepared in the same manner as Exemplified dye D-15, except that Compound d-7-3 was changed to Compound d-16-2.

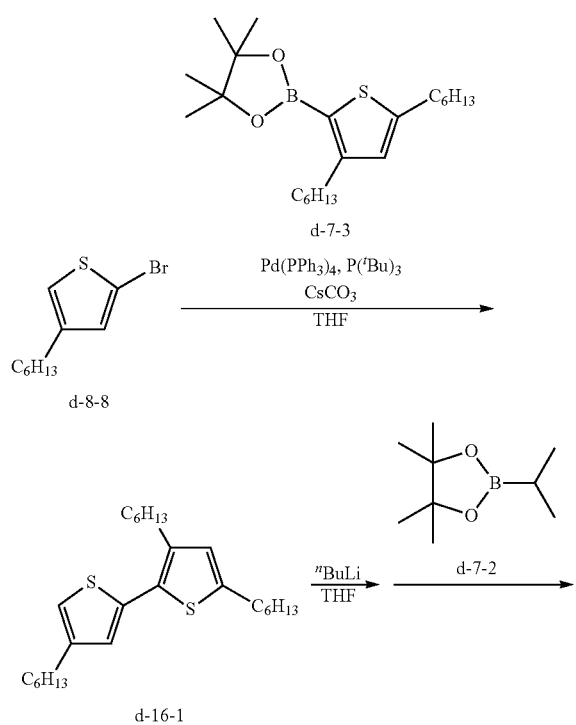

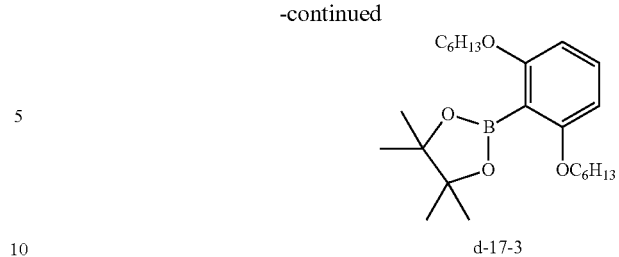

(Preparation of Exemplified Dye D-18)

Compound d-18-2 was prepared according to the method shown in the following scheme. Then, Exemplified dye D-18 was prepared in the same manner as Exemplified dye D-15, except that Compound d-7-3 was changed to Compound d-18-2.

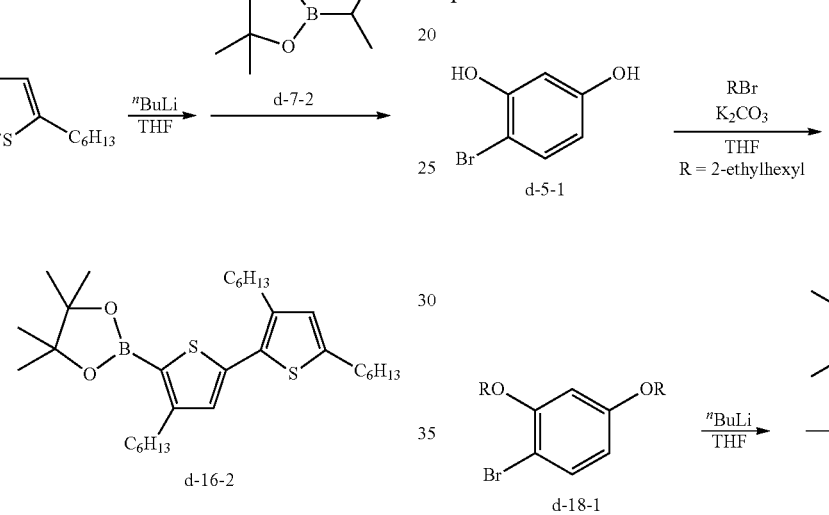

(Preparation of Exemplified Dye D-17)

Compound d-17-3 was prepared according to the method shown in the following scheme. Then, Exemplified dye D-17 was prepared in the same manner as Exemplified dye D-15, except that Compound d-7-3 was changed to Compound d-17-3.

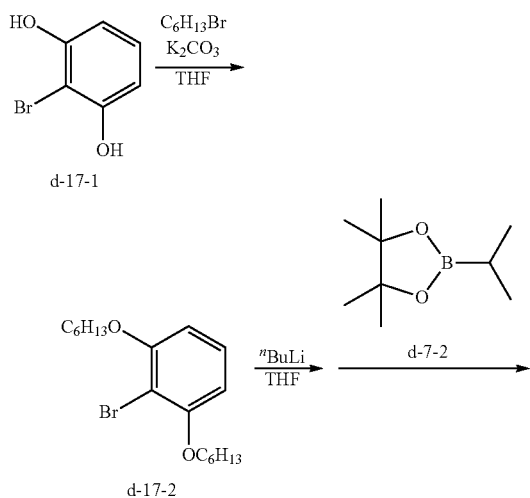

(Preparation of Exemplified Dye D-40)

Compound d-40-2 was prepared using Compound d-17-3. Further, Compound d-40-3 was prepared using Compound d-17-3 in the same manner as Compound d-9-1. Then, Exemplified dye D-40 was prepared using these compounds.

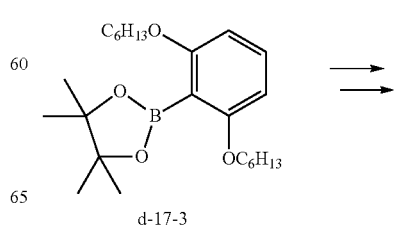

-continued

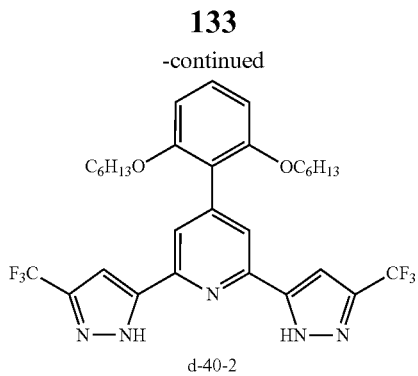

d-40-2

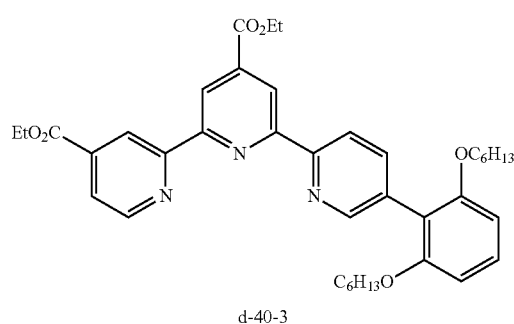

d-40-3

The structure of Compound d-40-2 obtained was confirmed by NMR and MS measurements.

$^1$H-NMR (CDCl$_3$, 400 MHz): δ (ppm): 12.3 (2H, br), 7.61 (2H, d), 7.27 (1H, t), 6.82 (2H, s), 6.57 (2H, d), 3.91 (4H, t), 1.65 (4H, dt), 1.30-1.15 (12H, m), 0.81 (3H, t) MS-ESI m/z=622.3 (M-H)$^-$ (Preparation of Exemplified Dye D-47)

Compound d-47-4 was prepared according to the method shown in the following scheme. Then, Exemplified dye D-47 was prepared in the same manner as Exemplified dye D-15, using Compound d-40-2 separately prepared.

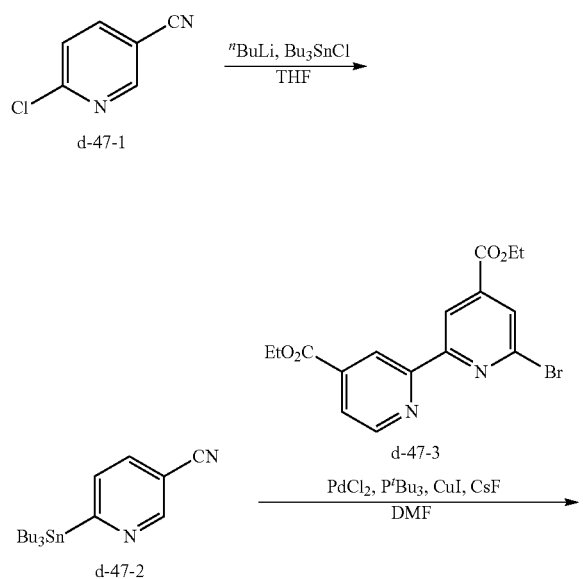

-continued

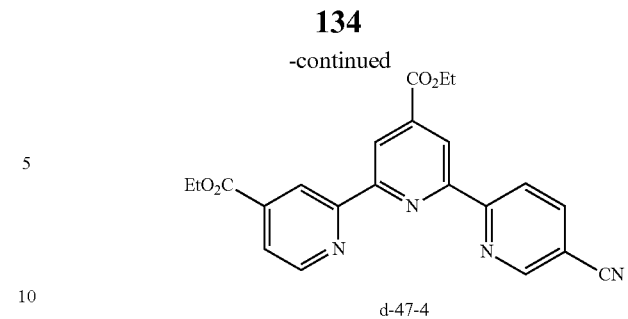

d-47-4

(Preparation of Exemplified Dye D-60)

Compound d-60-1 was prepared according to the method shown in the following scheme. Then, Exemplified dye D-60 was prepared in the same manner as Exemplified dye D-15, using Compound d-40-2 separately prepared.

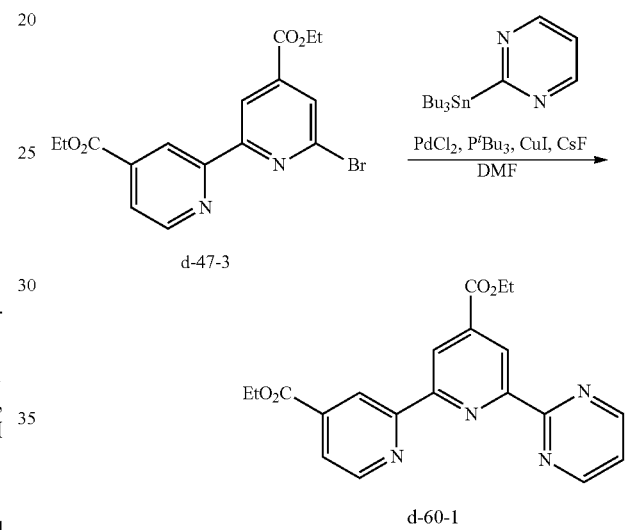

d-60-1

(Preparation of Exemplified Dye D-61)

Compound d-61-2 was prepared according to the method shown in the following scheme. Then, Exemplified dye D-61 was prepared in the same manner as Exemplified dye D-15, using Compound d-40-2 separately prepared.

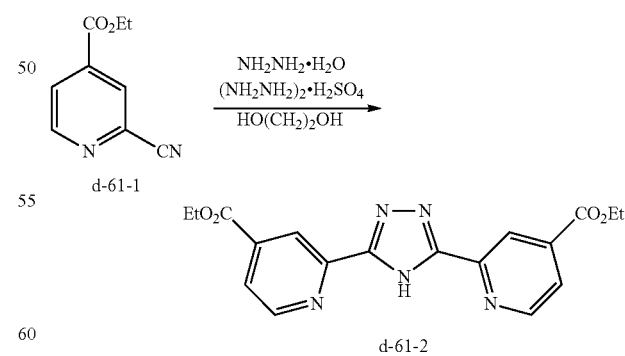

d-61-2

(Preparation of Exemplified Dye D-64)

Compound d-64-4 was prepared according to the method shown in the following scheme. Then, Exemplified dye D-64 was prepared in the same manner as Exemplified dye D-15, using Compound d-40-2 separately prepared.

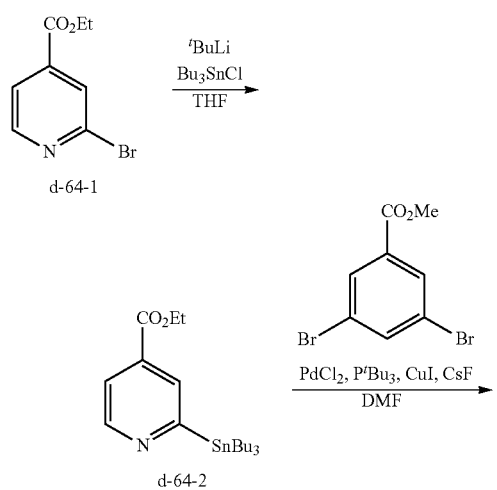

d-64-1

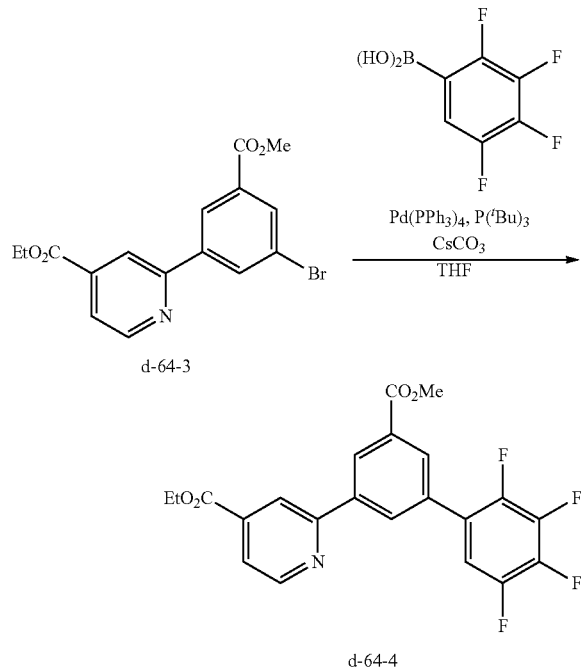

d-64-2 d-64-3 d-64-4

(Preparation of Exemplified Dye D-69)

Compound d-69-4 was prepared according to the method shown in the following scheme. Then, Exemplified dye D-69 was prepared in the same manner as Exemplified dye D-15, using Compound d-40-2 separately prepared.

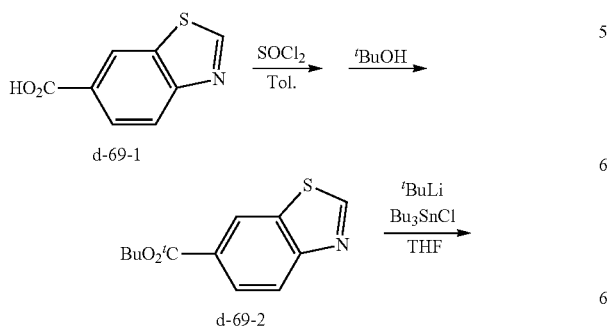

d-69-1 d-69-2

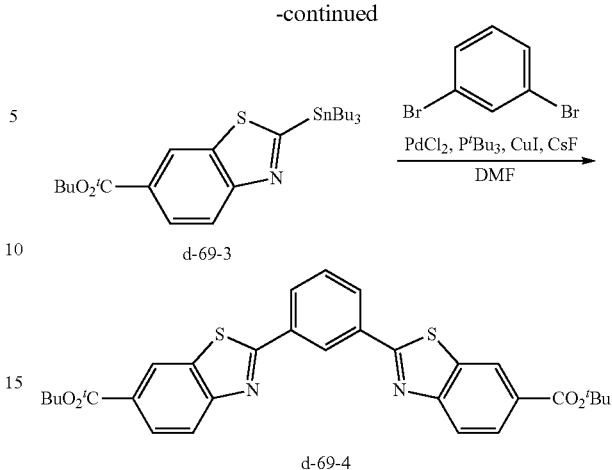

d-69-3 d-69-4

(Preparation of Exemplified Dye D-32)

Exemplified dye D-32 was prepared in the same manner as Exemplified dye D-17, except that $C_6H_{13}Br$ was changed to $CH_3I$.

(Preparation of Exemplified Dye D-23)

Compound d-23-6 was prepared according to the method shown in the following scheme. Then, Exemplified dye D-23 was prepared in the same manner as Exemplified dye D-7, except that Compound d-7-3 was changed to Compound d-23-6.

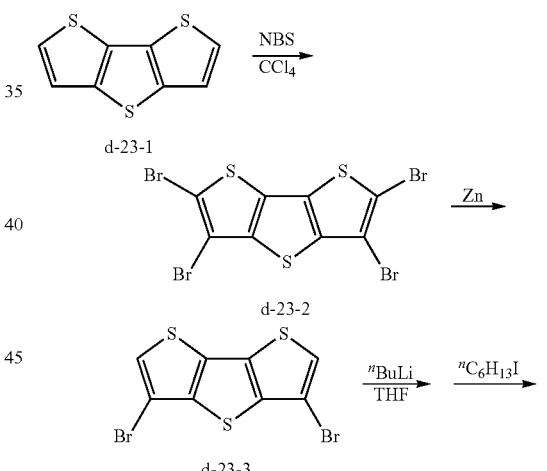

d-23-1 d-23-2

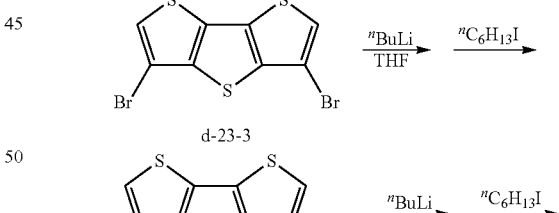

d-23-3

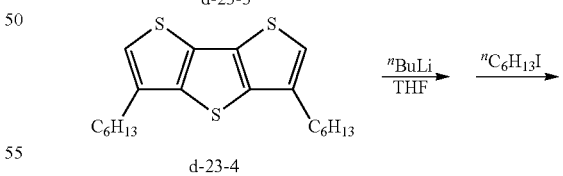

d-23-4

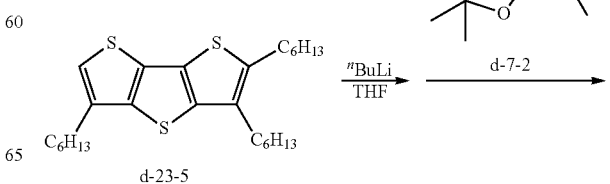

d-23-5

-continued

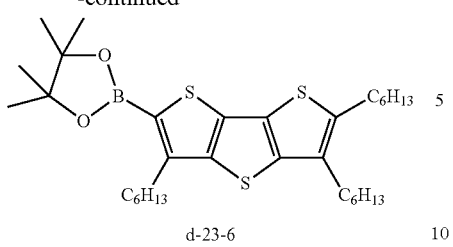

d-23-6

(Preparation of Exemplified Dye D-26)

Compound d-26-3 was prepared according to the method shown in the following scheme. Then, Exemplified dye D-26 was prepared in the same manner as Exemplified dye D-15, except that Compound d-7-3 was changed to Compound d-26-3.

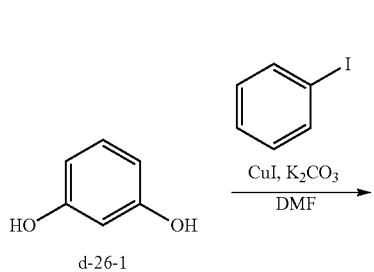

(Preparation of Exemplified Dye D-30)

Compound d-30-3 was prepared according to the method shown in the following scheme. Then, Exemplified dye D-30 was prepared in the same manner as Exemplified dye D-15, except that Compound d-7-3 was changed to Compound d-30-3.

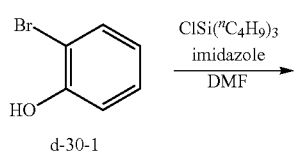

d-30-1

-continued

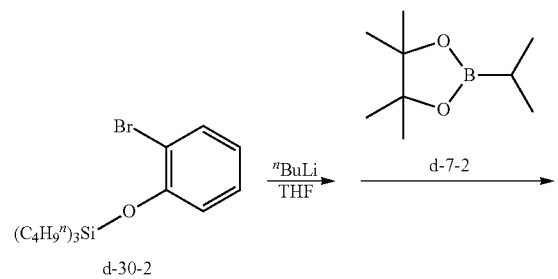

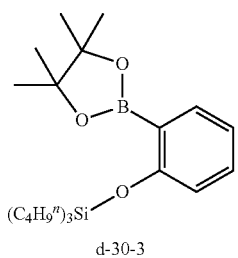

d-30-3

(Preparation of Exemplified Dye D-33)

Compound d-33-4 was prepared according to the method shown in the following scheme. Then, Exemplified dye D-33 was prepared in the same manner as Exemplified dye D-7, except that Compound d-17-3 was changed to Compound d-33-4.

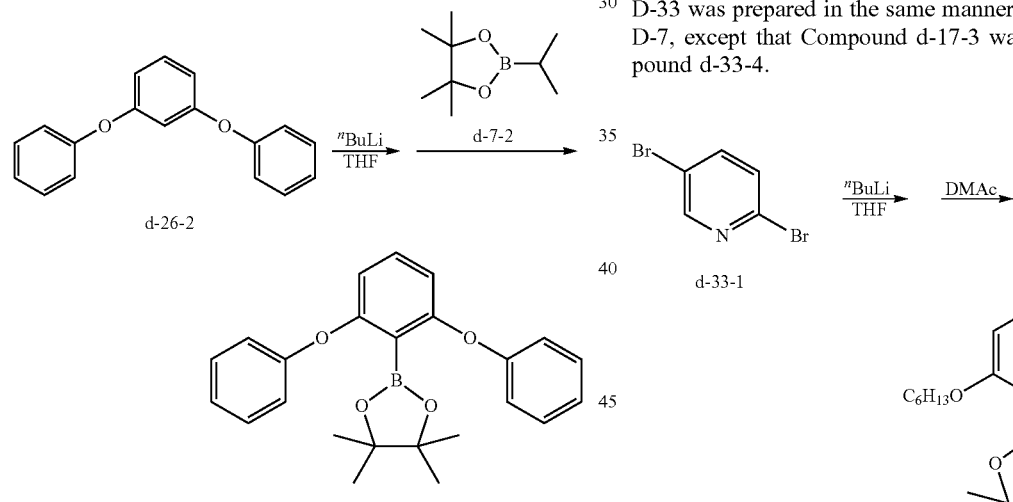

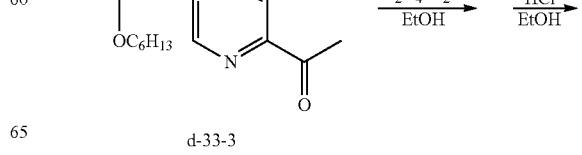

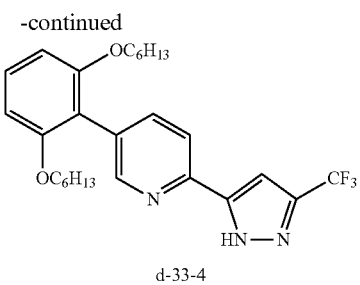

d-33-4

The structure of Compound d-33-4 obtained was confirmed by NMR and MS measurements.

$^1$H-NMR (CDCl$_3$, 400 MHz): δ (ppm): 11.5 (1H, br), 8.61 (1H, d), 7.83 (1H, dd), 7.61 (1H, d), 7.27 (1H, t), 6.94 (1H, s), 6.64 (1H, d), 3.92 (4H, t), 1.64 (4H, dt), 1.30-1.15 (12H, m), 0.81 (3H, t)

MS-ESI m/z=488.3 (M-H)$^-$ (Preparation of Exemplified Dye D-77)

Exemplified dye D-77 was prepared in the same manner as Exemplified dye D-33, except that Compound d-17-3 was changed to Compound d-77-3.

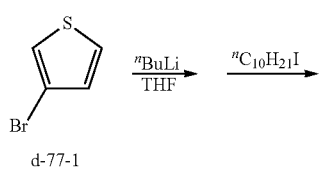

d-77-1

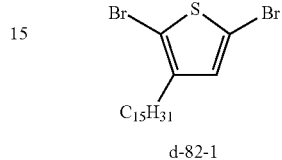

d-77-2

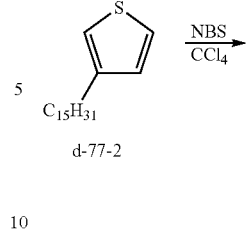

d-77-2

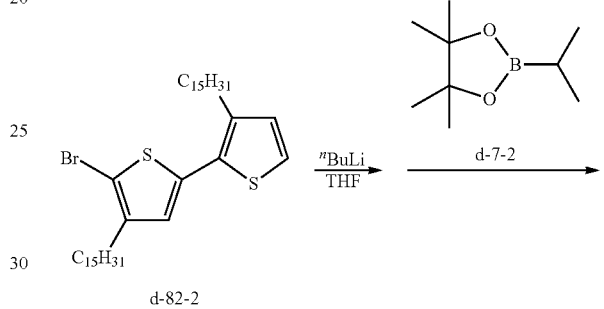

d-77-3

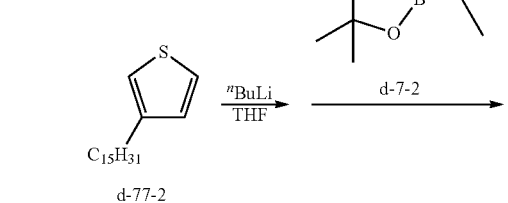

d-77-3

(Preparation of Exemplified Dye D-79)

Exemplified dye D-79 was prepared in the same manner as Exemplified dye D-7, except that Compound d-7-3 was changed to Compound d-77-3.

(Preparation of Exemplified Dye D-82)

Compound d-82-3 was prepared according to the method shown in the following scheme. Then, Exemplified dye D-82 was prepared in the same manner as Exemplified dye D-15, except that Compound d-7-3 was changed to Compound d-82-3.

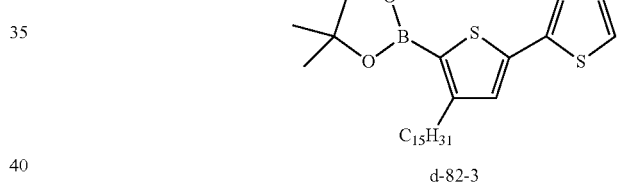

d-82-1, d-82-2

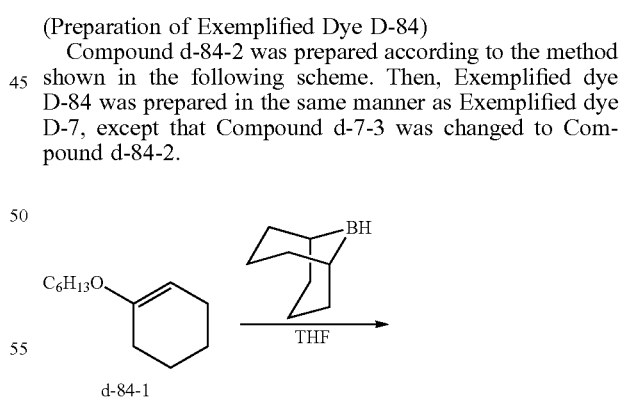

d-82-3

(Preparation of Exemplified Dye D-84)

Compound d-84-2 was prepared according to the method shown in the following scheme. Then, Exemplified dye D-84 was prepared in the same manner as Exemplified dye D-7, except that Compound d-7-3 was changed to Compound d-84-2.

d-84-1

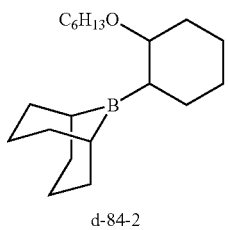

d-84-2

(Stannylation Reaction)

To about 5 g of a substrate with which a halogen was substituted, 1.2 times mole of bis(tributyltin) and 0.05 times mole of tetrakis(triphenylphosphineparadium) were refluxed in 100 ml of toluene under a nitrogen atmosphere. Completion of the reaction was confirmed by a thin-layer chromatography. After cooling to room temperature, the reaction liquid was filtrated and concentrated, followed by separation and refinement, using partition column chromatography equipment (AI-580, manufactured by Yamazen) and a mixed solvent of n-hexane, ethyl acetate and methanol as an eluent, by flowing the eluent while controlling the concentration gradient thereof. By concentration of the target fraction, the stannylated product was obtained.

(Stille Coupling)

About 2 g of a substrate with which a halogen was substituted, 1.3 times mole of the stannylated product, 0.05 times mole of palladium (II) chloride, 0.1 times mole of copper (I) iodide, 2 times mole of cesium fluoride, and 0.1 times mole of tri-t-butylphosphine were heated at 80° C. in 100 ml of N,N-dimethylacetamide under a nitrogen atmosphere. Completion of the reaction was confirmed by a thin-layer chromatography. The reaction liquid was filtrated and cooled to room temperature, followed by concentration, separation and refinement using the partition column chromatography equipment and the eluent similar to the above. By concentration of the target fraction, the target product was obtained.

(Preparation of Exemplified Dye D-86)

Synthesis of Dimethyl Ester (LA-3-11 Me) of Ligand LA-3-11

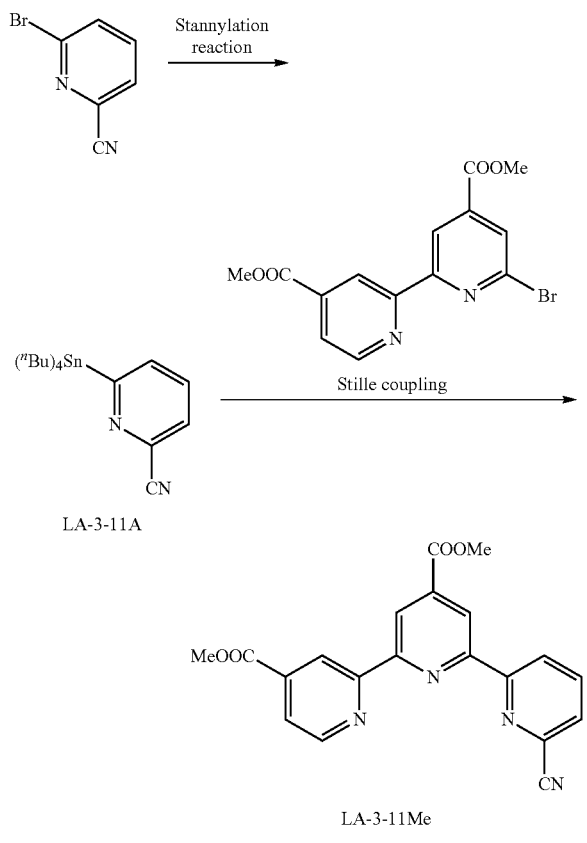

The stannylation reaction was applied to 5 g of 2-bromo-6-cyanopyridine, to give the stannylated LA-3-11A. The stille coupling was applied to, using 2 g of dimethyl 6-bromo-2,2'-bipyridine-4,4'-dicarboxylate and the stannylated LA-3-11A, to give Ligand LA-3-11 Me which was a dimethyl ester of Ligand LA-3-11.

Exemplified dye D-86 was prepared in the same manner as Exemplified dye D-15, using Compound d-40-2 separately prepared.

(Preparation of Exemplified Dye D-88)

Synthesis of Dimethyl Ester (LA-3-4 Me) of Ligand LA-3-4

Ligand LA-3-4 Me which was a dimethyl ester of Ligand LA-3-4 was obtained in the same manner as Ligand LA-3-11 Me, except that 5 g of 2-bromo-6-cyanopyridine which was a raw material in the synthesis of Ligand LA-3-11 Me was replaced with an equimolar amount of 2-bromo-5-trifluoromethylpyridine.

Exemplified dye D-88 was prepared in the same manner as Exemplified dye D-15, using Compound d-40-2 separately prepared.

(Preparation of Exemplified Dye D-89)

Synthesis of Dimethyl Ester (LA-3-19 Me) of Ligand LA-3-19

Ligand LA-3-19 Me which was a dimethyl ester of Ligand LA-3-19 was obtained in the same manner as Ligand LA-3-11 Me, except that 5 g of 2-bromo-6-cyanopyridine in the synthesis of Ligand LA-3-11 Me was replaced with an equimolar amount of 2-bromo-5-methylsulfonylpyridine.

Exemplified dye D-89 was prepared in the same manner as Exemplified dye D-15, using Compound d-40-2 separately prepared.

(Preparation of Exemplified Dye D-87)

Synthesis of Dimethyl Ester (LA-3-12 Me) of Ligand LA-3-12

Ligand LA-3-12 Me which was a dimethyl ester of Ligand LA-3-12 was obtained in the same manner as Ligand LA-3-11 Me, except that 5 g of 2-bromo-6-cyanopyridine in the synthesis of Ligand LA-3-11 Me was replaced with an equimolar amount of 2-bromo-5-nitropyridine.

Exemplified dye D-87 was prepared in the same manner as Exemplified dye D-15, using Compound d-40-2 separately prepared.

(Preparation of Exemplified Dye D-85)

Synthesis of Dimethyl Ester (LA-3-13 Me) of Ligand LA-3-13

Ligand LA-3-13 Me which was a dimethyl ester of Ligand LA-3-13 was obtained in the same manner as Ligand LA-3-11 Me, except that 5 g of 2-bromo-6-cyanopyridine in the synthesis of Ligand LA-3-11 Me was replaced with an equimolar amount of 2-bromo-6-acetylpyridine.

Exemplified dye D-85 was prepared in the same manner as Exemplified dye D-15, using Compound d-40-2 separately prepared.

(Preparation of Exemplified Dye D-91)

Synthesis of Dimethyl Ester (LA-4-3 Me) of Ligand LA-4-3

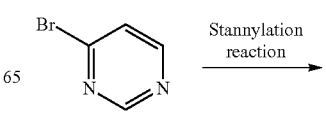

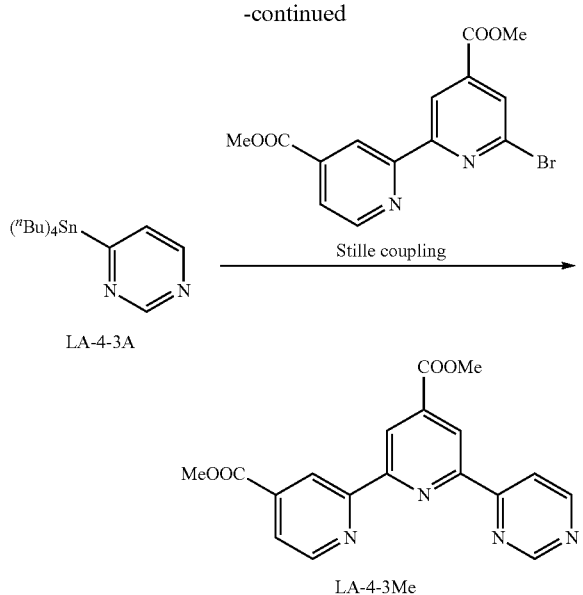

The stannylation reaction was applied to 5 g of 2-bromopyrimidine, to give the stannylated LA-4-3A. The stille coupling was applied to, using 2 g of dimethyl 6-bromo-2,2'-bipyridine-4,4'-dicarboxylate and the stannylated LA-4-3A, to give Ligand LA-4-3 Me which was a dimethyl ester of Ligand LA-4-3.

Exemplified dye D-91 was prepared in the same manner as Exemplified dye D-15, using Compound d-40-2 separately prepared.

(Preparation of Exemplified Dye D-57)
Synthesis of Dimethyl Ester (LA-4-13 Me) of Ligand LA-4-13

Ligand LA-4-13 Me which was a dimethyl ester of Ligand LA-4-13 was obtained in the same manner as Ligand LA-4-1 Me, except that 5 g of 2-bronopyrimidine in the synthesis of LA-4-1 Me was replaced with an equimolar amount of 2-bromobenzothiazole.

Exemplified dye D-57 was prepared in the same manner as Exemplified dye D-15, using Compound d-40-2 separately prepared.

(Preparation of Exemplified Dye D-92)
Synthesis of Trimethyl Ester (LA-5-7 Me) of Ligand LA-5-7

2-bromo-4-methoxycarbonylpyridine was converted to a stannylated product by the stannylation reaction, and this product and methyl 3,5-dibromobenzoate ester were subjected to reaction by the stille coupling, to give Ligand LA-5-7 Me which was a trimethyl ester of Ligand LA-5-7.

Exemplified dye D-92 was prepared in the same manner as Exemplified dye D-15, using Compound d-40-2 separately prepared.

(Preparation of Exemplified Dye D-93)
Synthesis of Dimethyl Ester (LA-6-4 Me) of Ligand LA-6-4

2-bromobenzothiazole was converted to a stannylated product by the stannylation reaction, and this product and 2-(3-bromo-5-methoxycarbonylphenyl)-4-methoxycarbonylpyridine were subjected to reaction by the stille coupling, to give Ligand LA-6-4 Me which was a dimethyl ester of Ligand LA-6-4.

Exemplified dye D-93 was prepared in the same manner as Exemplified dye D-15, using Compound d-40-2 separately prepared.

(Preparation of Exemplified Dye D-94)
Synthesis of Methyl Ester (LA-7-4 Me) of Ligand LA-7-4

Ligand LA-7-4 Me which was a methyl ester of Ligand LA-7-4 was obtained in the same manner as Ligand LA-4-1 Me, except that 6-bromo-2,2'-bipyridine-4,4'-dicaboxylate was replaced with ½ mole of 2,6-dibromo-4-methoxycarbonylpyridine.

Exemplified dye D-94 was prepared in the same manner as Exemplified dye D-15, using Compound d-40-2 separately prepared.

(Preparation of Exemplified Dye D-95)
Synthesis of Methyl Ester (LA-7-8 Me) of Ligand LA-7-8

LA-7-8 Me which was a methyl ester of LA-7-8 was obtained in the same manner as LA-7-4 Me, except that 2-bromopyrimidine was replaced with 1-bromobenzothiazole.

Exemplified dye D-95 was prepared in the same manner as Exemplified dye D-15, using Compound d-40-2 separately prepared.

(Preparation of Exemplified Dye D-96)
Synthesis of Methyl Ester (LA-7-10 Me) of Ligand LA-7-10

Ligand LA-7-10 Me which was a methyl ester of Ligand LA-7-10 was obtained in the same manner as Ligand LA-7-4 Me, except that 2-bromopyrimidine was replaced with 1-bromobenzimidazole.

Exemplified dye D-96 was prepared in the same manner as Exemplified dye D-15, using Compound d-40-2 separately prepared.

(Preparation of Exemplified Dye D-97)
Synthesis of Methyl Ester (LA-8-4 Me) of Ligand LA-8-4

Ligand LA-8-4 Me which was a methyl ester of Ligand LA-8-4 was obtained in the same manner as Ligand LA-5-7, except that 2-bromo-4-methoxycarbonylpyridine was replaced with 2-bromopyrimidine.

Exemplified dye D-97 was prepared in the same manner as Exemplified dye D-15, using Compound d-40-2 separately prepared.

(Preparation of Exemplified Dye D-98)
Synthesis of Methyl Ester (LA-8-12 Me) of Ligand LA-8-12

Ligand LA-8-12 Me which was a methyl ester of Ligand LA-8-12 was obtained in the same manner as Ligand LA-5-7, except that 2-bromo-4-methoxycarbonylpyridine was replaced with 2-bromobenzoxazole.

Exemplified dye D-98 was prepared in the same manner as Exemplified dye D-15, using Compound d-40-2 separately prepared.

(Preparation of Exemplified Dye D-99)
Synthesis of Methyl Ester (LA-8-11 Me) of Ligand LA-8-11

Ligand LA-8-11 Me which was a methyl ester of Ligand LA-8-11 was obtained in the same manner as Ligand LA-5-7, except that 2-bromo-4-methoxycarbonylpyridine was replaced with 2-bromo-3-methylbenzimidazole.

Exemplified dye D-99 was prepared in the same manner as Exemplified dye D-15, using Compound d-40-2 separately prepared.

The maximum absorption wavelengths ($\lambda$max) of the thus-obtained Exemplified dyes were measured in the same manner as Exemplified dye D-8, and the results are shown in Table 1 together with the measured results of mass spectrum (MS).

The maximum absorption wavelength of each of the metal complex dyes of the present invention was within the range of 500 to 750 nm, which was a preferable range for photoelectric conversion elements.

TABLE 1

| Metal complex dye | MS-ESI | Absorption maximum wavelength (nm) |
|---|---|---|
| D-1 | MS-ESI m/z = 931.0 (M − H)⁻ | 513 |
| D-2 | MS-ESI m/z = 912.1 (M − H)⁻ | 516 |
| D-7 | MS-ESI m/z = 986.2 (M − H)⁻ | 512 |
| D-8 | MS-ESI m/z = 1,012.2 (M − H)⁻ | 521 |
| D-9 | MS-ESI m/z = 1,108.3 (M − H)⁻ | 512 |
| D-12 | MS-ESI m/z = 1,023.2 (M − H)⁻ | 732 |
| D-13 | MS-ESI m/z = 917.2 (M − H)⁻ | 724 |
| D-15 | MS-ESI m/z = 1,061.2 (M − H)⁻ | 713 |
| D-16 | MS-ESI m/z = 1,227.3 (M − H)⁻ | 712 |
| D-17 | MS-ESI m/z = 1,087.2 (M − H)⁻ | 706 |
| D-18 | MS-ESI m/z = 1,143.3 (M − H)⁻ | 704 |
| D-23 | MS-ESI m/z = 1,182.2 (M − H)⁻ | 524 |
| D-26 | MS-ESI m/z = 1,071.1 (M − H)⁻ | 702 |
| D-30 | MS-ESI m/z = 1,101.2 (M − H)⁻ | 705 |
| D-32 | MS-ESI m/z = 947.1 (M − H)⁻ | 706 |
| D-33 | MS-ESI m/z = 1,068.3 (M − H)⁻ | 521 |
| D-40 | MS-ESI m/z = 1,319.4 (M − H)⁻ | 712 |
| D-47 | MS-ESI m/z = 1,068.2 (M − H)⁻ | 678 |
| D-60 | MS-ESI m/z = 1,044.2 (M − H)⁻ | 687 |
| D-61 | MS-ESI m/z = 1,033.2 (M − NBu₄)⁻ | 695 |
| D-64 | MS-ESI m/z = 1,113.2 (M + H − 2NBu₄₊)²⁻ | 713 |
| D-69 | MS-ESI m/z = 1,154.2 (M − NBu₄)⁻ | 687 |
| D-77 | MS-ESI m/z = 1,028.2 (M − H)⁻ | 514 |
| D-79 | MS-ESI m/z = 1,028.2 (M − H)⁻ | 515 |
| D-82 | MS-ESI m/z = 1,395.5 (M − H)⁻ | 714 |
| D-84 | MS-ESI m/z = 918.2 (M − H)⁻ | 510 |
| D-85 | MS-ESI m/z = 1,085.2 (M − H)⁻ | 701 |
| D-86 | MS-ESI m/z = 1,068.2 (M − H)⁻ | 714 |
| D-87 | MS-ESI m/z = 1,088.2 (M − H)⁻ | 712 |
| D-88 | MS-ESI m/z = 1,111.2 (M − H)⁻ | 706 |
| D-89 | MS-ESI m/z = 1,121.2 (M − H)⁻ | 711 |
| D-91 | MS-ESI m/z = 1,044.2 (M − H)⁻ | 688 |
| D-92 | MS-ESI m/z = 1,085.2 (M − NBu₄)⁻ | 664 |
| D-93 | MS-ESI m/z = 1,097.2 (M − NBu₄)⁻ | 675 |
| D-94 | MS-ESI m/z = 1,001.2 (M − H)⁻ | 667 |
| D-95 | MS-ESI m/z = 1,111.2 (M − H)⁻ | 669 |
| D-96 | MS-ESI m/z = 1,077.3 (M − H)⁻ | 667 |
| D-97 | MS-ESI m/z = 999.2 (M − NBu₄)⁻ | 653 |
| D-98 | MS-ESI m/z = 1,103.3 (M − NBu₄)⁻ | 656 |
| D-99 | MS-ESI m/z = 1,077.2 (M − NBu₄)⁻ | 658 |

—Calculation of Angle θ and Length—

1) Calculation Method i) Angle θ

As described above, in the most stable structure determined by DFT calculation, if the coordinates of G1, G2, and M are defined respectively as G1 (x1, y1, z1), G2 (x2, y2, z2), and M (x3, y3, z3), θ can be calculated from the following formula.

$$\theta = \arccos\left\{\frac{(x_2 - x_1)(x_3 - x_1) + (y_2 - y_1)(y_3 - y_1) + (z_2 - z_1)(z_3 - z_1)}{\{(x_2 - x_1)^2 + (y_2 - y_1)^2 + (z_2 - z_1)^2\}^{1/2}\{(x_3 - x_1)^2 + (y_3 - y_1)^2 + (z_3 - z_1)^2\}^{1/2}}\right\}$$

ii) Calculation of Length

Calculation is carried out as described above. Shown below are an example of the calculated results of: the maximum linking chain number $N_R$ of linking chain numbers of a linking chain linking from the atom G1 to an atom located at the furthest position through a linkage of the substituent R; and the minimum linking chain number $N_{M\text{-}G1}$ of linking chain numbers of a linking chain linking from the metal atom M to the atom G1. In the following metal complex dye, $N_R$=7 and $N_{M\text{-}G1}$=8.

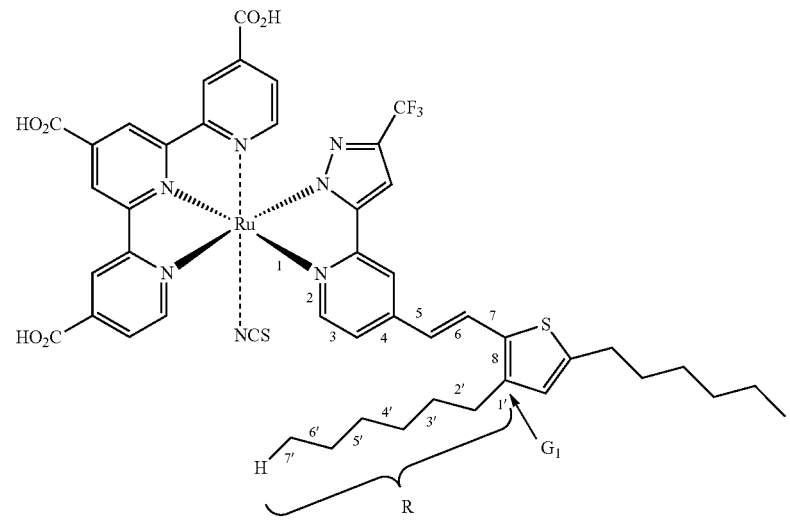

The results are shown in Table 2.

TABLE 2

| Metal complex dye | Angle θ (degrees) | $N_R/N_{M-G1}$ |
|---|---|---|
| D-1 | 143 | 0.57 |
| D-2 | 142 | 1.14 |
| D-7 | 88 | 1.17 |
| D-8 | 85 | 0.88 |
| D-9 | 87 | 1.17 |
| D-12 | 87 | 1.17 |
| D-13 | 88 | 1.17 |
| D-15 | 87 | 1.17 |
| D-16 | 86 | 1.17 |
| D-17 | 69 | 1.33 |
| D-18 | 69 | 1.33 |
| D-23 | 88 | 1.17 |
| D-26 | 70 | 1.00 |
| D-30 | 69 | 1.17 |
| D-32 | 69 | 0.50 |
| D-33 | 27 | 1.60 |
| D-40 | 69 | 1.33 |
| D-47 | 69 | 1.33 |
| D-60 | 69 | 1.33 |
| D-61 | 69 | 1.33 |
| D-64 | 69 | 1.33 |
| D-69 | 69 | 1.33 |
| D-77 | 48 | 2.20 |
| D-79 | 88 | 2.67 |
| D-82 | 88 | 2.67 |
| D-84 | 69 | 1.33 |
| D-85 | 69 | 1.33 |
| D-86 | 69 | 1.33 |
| D-87 | 69 | 1.33 |
| D-88 | 69 | 1.33 |
| D-89 | 69 | 1.33 |
| D-91 | 69 | 1.33 |
| D-92 | 69 | 1.33 |
| D-93 | 69 | 1.33 |
| D-94 | 69 | 1.33 |
| D-95 | 69 | 1.33 |
| D-96 | 69 | 1.33 |
| D-97 | 69 | 1.33 |
| D-98 | 69 | 1.33 |
| D-99 | 69 | 1.33 |
| S-1 | 174 | 0.30 |
| S-2 | None | None |

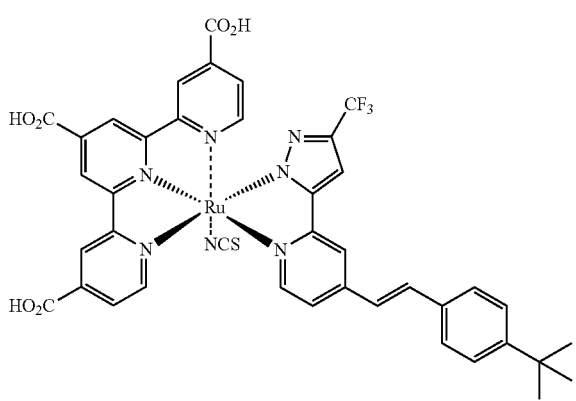

S-1

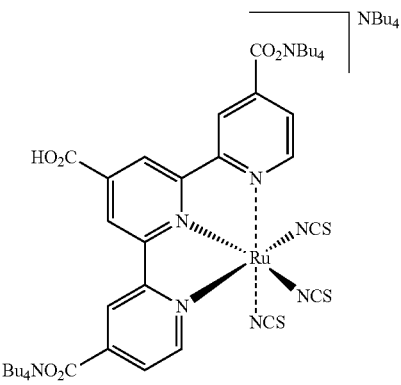

S-2

In the above, "NBu$_4$" means a tetrabutylammonium ion.

Example 2

Various kinds of pastes for forming a semiconductor layer or a light-scattering layer of a semiconductor electrode that constitutes a photoelectrode were prepared, and dye-sensitized solar cells were produced using the pastes.

[Preparation of Paste]

First, the pastes for forming the semiconductor layer or the light-scattering layer of the semiconductor electrode that constitutes the photoelectrode were prepared according to the compositions shown in Table 3. In the following preparation, a slurry was prepared by incorporating TiO$_2$ particles or mica particles in a medium with stirring, and then a paste was obtained by adding a thickener, a cellulose-based binder (in Table 3, indicated as 'CB') to the slurry, followed by kneading.

The particles (TiO$_2$ particles and mica particles) in Table 3 are as follows.

—TiO$_2$ Particles—

Particles 1: anatase, average particle diameter, 25 nm

TiO$_2$ particles 2: anatase, average particle diameter, 200 nm

TiO$_2$ particles S1: (rod-shaped) anatase, diameter, 100 nm, aspect ratio, 5

TiO$_2$ particles S2: (rod-shaped) anatase, diameter, 30 nm, aspect ratio, 6.3

TiO$_2$ particles S3: (rod-shaped) anatase, diameter, 50 nm, aspect ratio, 6.1

TiO$_2$ particles S4: (rod-shaped) anatase, diameter, 75 nm, aspect ratio, 5.8

TiO$_2$ particles S5: (rod-shaped) anatase, diameter, 130 nm, aspect ratio, 5.2

TiO$_2$ particles S6: (rod-shaped) anatase, diameter, 180 nm, aspect ratio, 5

TiO$_2$ particles S7: (rod-shaped) anatase, diameter, 240 nm, aspect ratio, 5

TiO$_2$ particles S8: (rod-shaped) anatase, diameter, 110 nm, aspect ratio, 4.1

TiO$_2$ particles S9: (rod-shaped) anatase, diameter, 105 nm, aspect ratio, 3.4

Mica particles P1: (plate-shaped) diameter, 100 nm, aspect ratio, 6

TABLE 3

| Paste | Particles | Medium | Thickener | Remarks |
|---|---|---|---|---|
| 1 | 1 | Nitric acid solution | CB | |
| 2 | 1, 2 | Nitric acid solution | CB | TiO$_2$ 1:TiO$_2$ 2 = 30:70 (mass ratio) |
| 3 | 1, S1 | Nitric acid solution | CB | (Mass of TiO$_2$ S1):(Paste 1) = 10:90 (mass ratio) |
| 4 | 1, S1 | Nitric acid solution | CB | (Mass of TiO$_2$ S1):(Paste 1) = 30:70 (mass ratio) |
| 5 | 1, S1 | Nitric acid solution | CB | (Mass of TiO$_2$ S1):(Paste 1) = 50:50 (mass ratio) |
| 6 | 1, P1 | Nitric acid solution | CB | (Mass of mica P1):(Paste 1) = 20:80 (mass ratio) |
| 7 | 1, S2 | Nitric acid solution | CB | (Mass of TiO$_2$ S2):(Paste 1) = 30:70 (mass ratio) |
| 8 | 1, S3 | Nitric acid solution | CB | (Mass of TiO$_2$ S3):(Paste 1) = 30:70 (mass ratio) |
| 9 | 1, S4 | Nitric acid solution | CB | (Mass of TiO$_2$ S4):(Paste 1) = 30:70 (mass ratio) |
| 10 | 1, S5 | Nitric acid solution | CB | (Mass of TiO$_2$ S5):(Paste 1) = 30:70 (mass ratio) |
| 11 | 1, S6 | Nitric acid solution | CB | (Mass of TiO$_2$ S6):(Paste 1) = 30:70 (mass ratio) |
| 12 | 1, S7 | Nitric acid solution | CB | (Mass of TiO$_2$ S7):(Paste 1) = 30:70 (mass ratio) |
| 13 | 1, S8 | Nitric acid solution | CB | (Mass of TiO$_2$ S8):(Paste 1) = 30:70 (mass ratio) |
| 14 | 1, S9 | Nitric acid solution | CB | (Mass of TiO$_2$ S9):(Paste 1) = 30:70 (mass ratio) |

Figure 2:
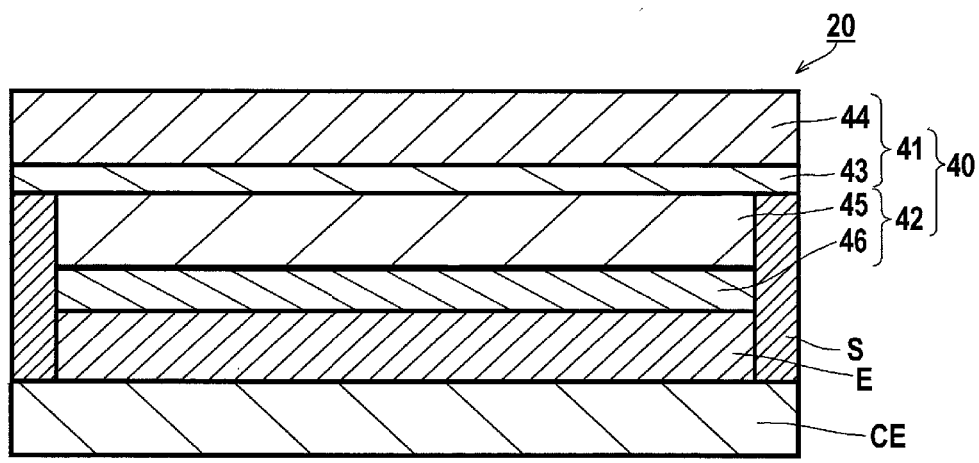
FIG. 2 is a cross-sectional view schematically showing the dye-sensitized solar cell, prepared in Examples 1 and 4.
Figure 3:
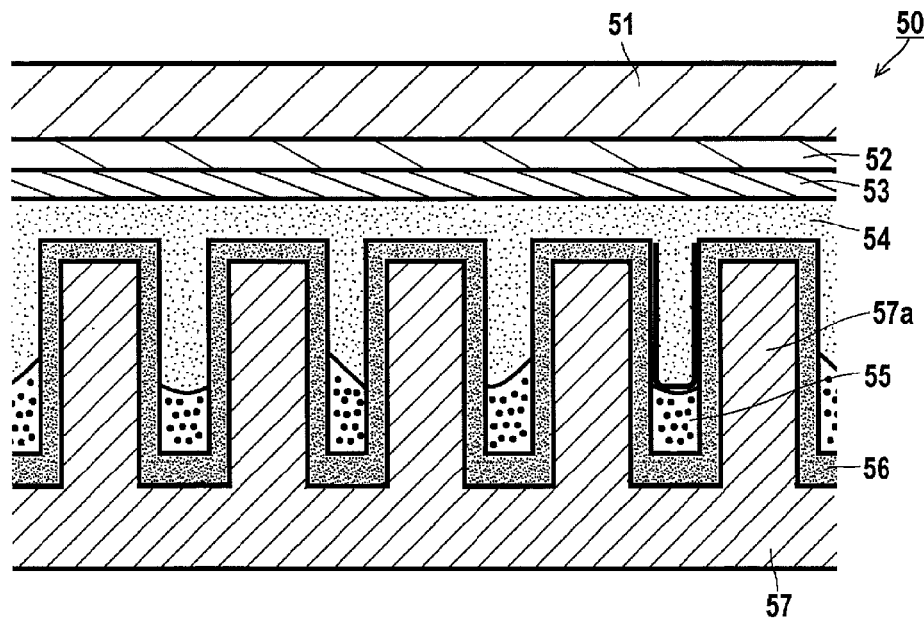
FIG. 3 is a cross-sectional view schematically showing the dye-sensitized solar cell, prepared in Example 2.

According to the procedure described below, a photoelectrode having the same configuration as that of the photoelectrode 12 shown in FIG. 5 of JP-A-2002-289274 was produced, and using the photoelectrode, a dye-sensitized solar cell 1 of a scale of 10 mm×10 mm having the same configuration as that of the dye-sensitized solar cell 20 shown in FIG. 3 of JP-A-2002-289274 except for the photoelectrode, was produced. The specific configuration thereof was shown in FIG. 2 attached to the present application. In FIG. 2 of the present application, 20 represents a dye-sensitized solar cell, 41 represents a transparent electrode, 42 represents a semiconductor electrode, 43 represents a transparent electrically-conductive film, 44 represents a substrate, 45 represents a semiconductor layer, 46 represents a light-scattering layer, 40 represents a photoelectrode, CE represents a counter electrode, E represents an electrolyte, and S represents a spacer.

A transparent electrode in which a fluorine-doped SnO$_2$ electrically-conductive film (thickness: 500 nm) was formed on a glass substrate, was provided. On this SnO$_2$ electrically-conductive film, the paste 2 was applied to by screen printing, followed by drying. Then, the paste was calcined under the conditions of 450° C. in the air. Further, by repeating this screen printing and calcination using the paste 2, the semiconductor electrode A having the same configuration as that of the semiconductor electrode 42 shown in FIG. 2 (the area of the light-receiving face 10 mm×10 mm; the layer thickness 15 μm; the layer thickness of the dye-adsorbing layer 10 μm; the layer thickness of the light-scattering layer 5 μm; and the content of the rod-shaped TiO$_2$ particles 1 contained in the light-scattering layer 30% by mass) were formed on the SnO$_2$ electrically-conductive film. Thus, the photoelectrode A, which did not contain the dye including the metal complex dye of the present invention, was prepared.

Then, the respective metal complex dye was adsorbed on the semiconductor electrode A as follows. First, anhydrous ethanol which had been dehydrated over magnesium ethoxide was used as a solvent, and the metal complex dye described in Table 4 was dissolved in this anhydrous ethanol to a concentration of 3×10$^{-4}$ mol/L, to prepare the respective dye solution. Then, the semiconductor electrode was immersed in this solution, and thereby the dye was adsorbed on the semiconductor electrode in an amount of about 1.5×10$^{-7}$ mol/cm$^2$, to complete the respective photoelectrode 40.

Then, a platinum electrode (thickness of Pt thin film, 100 nm) having the same shape and size as those of the photoelectrode as a counter electrode, and an iodine-based redox solution containing: 0.05M of iodine, 0.01M of lithium iodide, 0.6M of 1-propyl-3-methylimidazolium iodide and 4-tert-butylpyridine, as an electrolyte E, were prepared. Further, a spacer-S(trade name: "Surlyn") manufactured by DuPont, which had a shape matching to the size of the semiconductor electrode, was provided. As shown in FIG. 3 of JP-A-2002-289274, the photoelectrode 40 and the counter electrode CE were arranged to face each other, with the spacer-S interposed therebetween, followed by filling the electrolyte in the inside thereof. Thus, a respective dye-sensitized solar cell (cell A) using the respective photoelectrode A was completed. The performance evaluation of the solar cell was conducted. The results are shown in Table 4.
(Test Method)
Cell Characteristic Test Photoelectric conversion efficiency η (%), together with short-circuit current density Jsc (mA/cm$^2$), open-circuit voltage Voc (mV), and fill factor FF of each of the dye-sensitized solar cells (cell A), were measured, with irradiating a pseudo sunlight of 1,000 W/m$^2$ from a xenon lamp through an AM 1.5 filter, using a solar similator (WXS-85H, manufactured by WACOM). The current-voltage characteristics were measured, using an I-V tester.
Evaluation Series (1)
—Open-Circuit Voltage Voc (mV)—

The open-circuit voltage Voc (mV) obtained in the above is judged as being acceptable, if it is 560 mV or more.
—Standard Deviation of Open-Circuit Voltage Voc (mV)—

In order to investigate a deviation of performance between preparation lots of the dye-sensitized solar cell, the dye-sensitized solar cells (cell A) were repeatedly prepared 10 times to each metal complex dye in the same manner as above. An open-circuit voltage Voc (mV) of each of the thus-prepared cells was measured, and a standard deviation of the open-circuit voltage Voc (mV) was calculated.

The standard deviation of the open-circuit voltage Voc (mV) is judged as being acceptable, if it is 0.015 or less.
—Durability—

The durability was evaluated in terms of rate of decrease in open-circuit voltage Voc (mV) in heat resistance of the dye-sensitized solar cell.

The open-circuit voltage Voc (mV) of the dye-sensitized solar cell (cell A) prepared as above was measured as above. Then, regarding durability, the open-circuit voltage Voc (mV) with the lapse of time at 80° C. for 300 hours in the dark was measured, to obtain a rate of decrease (%). The rate of decrease (%) was calculated according to the following expression.

[(Initial open-circuit voltage−Open-circuit voltage with the lapse of time in the dark)/Initial open-circuit voltage]×100

The rate of decrease is judged as being acceptable, if it is 8.0% or less.

Evaluation Series (2)

—Desorption Rate—

For evaluation of adsorption power of a metal complex dye onto the titanium oxide surface, a desorption rate of the metal complex dye from the titanium oxide surface was used as an index.

The desorption rate of the metal complex dye was calculated by means of a Quartz Crystal microbalance with Dissipation monitoring (QCM-D) intermolecular interaction measuring apparatus E1 (manufactured by Meiwafosis).

Paste 2 (anatase, average particle size: 25 nm) was printed by screen printing (film thickness: 20 μm) on a gold sensor (manufactured by Meiwafosis) for use for the QCM-D. By calcining the thus-printed gold sensor at 450° C. for 1 hour in the air, to prepare a gold sensor having a semiconductor layer adsorbed thereon.

The thus-prepared sensor was installed in the QCM-D intermolecular interaction measuring apparatus, and 0.2 mM of a dye solution (DMF/t-BuOH=1/1) was flowed therein, to make the dye adsorb on the semiconductor layer in a dye adsorption amount of a predetermined value (200 μg/cm$^2$). The dye adsorption amount was calculated from a resonance frequency shift (ΔF) of a quartz oscillator according to the following Sauerbrey equation.

$$\Delta F = -2 \times F_0^2 \times \Delta m / A(\mu \times P)^{1/2}$$

In the formula, $F_0$ represents a single frequency of a quartz oscillator, Δm represents a mass change, A represents a piezoelectric active area of the Au electrode, and μ and P represents quartz density and modulus of rigidity, respectively.

Then, by flowing the dye solution into the electrolyte E at 80° C. for 4 hours, to measure desorption amount of the dye. Desorption amount of the dye was also calculated according to the Sauerbrey equation.

The desorption rate is judged to be acceptable, if it is 15 μg/cm$^2$·hr or less.

Evaluation Series (3)

—λmax Shift—

The titanium oxide paste 2 was printed on a FTO substrate by a screen printing, to a film thickness of 5 μm as a semiconductor layer, and the thus-printed matter was immersed in 1.0 mM of the respective dye solution for a period of time from 30 minutes to 12 hours, to adsorb the dye thereon, to quantitate a dye adsorption amount. The dye adsorption amount was quantitated, by desorbing a dye with a 1 normal tetrabutylammonium hydroxide methanol solution, on a high-performance liquid chromatography. Transmission spectra of separately prepared cells under the conditions such that a dye adsorption density would become 70 μg/cm$^2$ or 140 μg/cm$^2$, were measured with respect to each dye, to observe a change of spectrum shape and a wavelength shift of λmax. Measurement was carried out using a spectrophotometer (U-4100, manufactured by Hitachi High-Technologies Corporation).

(Measuring Conditions for High-Performance Liquid Chromatography (HPLC))

Equipment used: System controller SCL-10AVP
    Column oven: CTO-10ASVP
    Detector: SPD-10AVVP
    Degasser: DGU-14AM
    Solution-sending unit: LC-10ADVP (trade name, manufactured by Shimadzu)
    Column: YMC-Pack ODS-AM, model number AM-312
    Size: 150×6.0 mm I.D. (manufactured by YMC Co., Ltd. Japan)
    Flow rate: 0.75 mL/min
    Eluent: MeOH/Water=80/20 (containing 0.02% tetrabutylammonium hydroxide)
    Temperature: 40° C.
    Detection wavelength: 254 nm A ratio of λmax (λmax 2) when the dye amount was 140 μg/cm$^2$ to λmax (λmax 1) when the dye amount was 70 μg/cm$^2$, λmax 2/λmax 1, was calculated.

The λmax 2/λmax 1 is judged as being acceptable, if it is 0.9 or more.

—Short-Circuit Current Density Jsc (mA/Cm$^2$)—

The short-circuit current density Jsc (mA/cm$^2$) obtained by the cell characteristic test was evaluated according to the following criterion.

The short-circuit current density Jsc (mA/cm$^2$) is judged to be acceptable, if it is 18.0 mA/cm$^2$ or more.

Evaluation Series (4)

—Solution Stability—

Each of dye solutions was prepared, in which the respective metal complex dye shown in Table 4 was adjusted to 34 μM, with, as a solvent, anhydrous ethanol dehydrated over magnesium ethoxide. Each of the dye solutions was encapsulated in a sealable cell, and light of 70,000 Lx was irradiated thereto using a merry-go-round-type light-resistance tester (III(N)-500 W, manufactured by Eagle Engineering), to observe attenuation of λmax with the lapse of time, to evaluate dye stability as follows.

A 0.1 mM solution before light irradiation was diluted with a given quantity of a solvent so that absorbance (Abs.) of λmax would become 1. This was defined as dye residual ratio of 100%. Separately, a sample after irradiation for 200 hours was diluted by adding thereto the same quantity of the solvent, and a value multiplying the absorbance (Abs.) of λmax of the thus-diluted sample after irradiation for 200 hours by 100 was defined as a dye residual ratio at the time. Measurement was carried out using a spectrophotometer (U-4100 (trade name), manufactured by Hitachi High-Technologies).

The dye residual ratio is judged to be acceptable, if it is 70% or more.

Evaluation Series (5)

—Adsorption Rate—

The adsorption rate of the metal complex dye onto a titanium dioxide surface was measured as follows.

The gold sensor having a semiconductor layer adsorbed thereon, which was prepared for the measurement of desorption rate, was installed in the QCM-D intermolecular interaction measuring apparatus, and by flowing therein 0.2 mM of a dye solution (DMF/t-BuOH=1/1), to make the dye adsorb on the semiconductor layer in a given amount (0.20 mg/cm$^2$). The dye adsorption amount was calculated according to the Sauerbrey equation. The adsorption rate of the dye was determined from the time period until the dye adsorption amount became a predetermined value.

The adsorption rate is judged to be acceptable, if it is 15 μg/cm$^2$·hr or more.

These results are shown together, in the order of evaluation series, in Table 4.

TABLE 4

| Sample No. | Metal complex dye | Angle θ (degrees) | $N_R/N_{M-G1}$ | (1) Voc (mV) | Standard deviation of Voc | Voc rate of decrease (%) after heat-resistance test |
|---|---|---|---|---|---|---|
| 101 | D-1 | 143 | 0.57 | 561 | 0.015 | 8.0 |
| 102 | D-2 | 142 | 1.14 | 572 | 0.011 | 6.1 |
| 103 | D-32 | 69 | 0.50 | 560 | 0.015 | 7.9 |
| 104 | D-84 | 70 | 1.33 | 633 | 0.003 | 3.8 |
| 105 | D-23 | 88 | 1.17 | 643 | 0.003 | 3.8 |
| 106 | D-7 | 88 | 1.17 | 656 | 0.003 | 3.4 |
| 107 | D-8 | 85 | 0.88 | 651 | 0.003 | 3.6 |
| 108 | D-12 | 87 | 1.17 | 642 | 0.005 | 3.4 |
| 109 | D-13 | 88 | 1.17 | 641 | 0.004 | 3.6 |
| 110 | D-33 | 27 | 1.60 | 641 | 0.001 | 1.9 |
| 111 | D-77 | 48 | 2.20 | 641 | 0.002 | 2.0 |
| 112 | D-79 | 88 | 2.67 | 656 | 0.002 | 3.5 |
| 113 | D-26 | 70 | 1.00 | 650 | 0.004 | 2.9 |
| 114 | D-30 | 69 | 1.17 | 652 | 0.003 | 2.9 |
| 115 | D-15 | 87 | 1.17 | 677 | 0.002 | 2.2 |
| 116 | D-16 | 86 | 1.17 | 684 | 0.002 | 2.0 |
| 117 | D-17 | 69 | 1.33 | 691 | 0.002 | 2.1 |
| 118 | D-18 | 69 | 1.33 | 684 | 0.002 | 2.1 |
| 119 | D-82 | 88 | 2.67 | 691 | 0.002 | 2.0 |
| 120 | D-40 | 69 | 1.33 | 695 | 0.002 | 2.0 |
| 121 | D-9 | 87 | 1.17 | 674 | 0.003 | 2.2 |
| 122 | D-47 | 69 | 1.33 | 699 | 0.004 | 1.9 |
| 123 | D-60 | 69 | 1.33 | 681 | 0.002 | 2.4 |
| 124 | D-85 | 69 | 1.33 | 681 | 0.004 | 2.6 |
| 125 | D-86 | 69 | 1.33 | 683 | 0.005 | 2.0 |
| 126 | D-87 | 69 | 1.33 | 698 | 0.002 | 2.8 |
| 127 | D-88 | 69 | 1.33 | 684 | 0.004 | 2.0 |
| 128 | D-89 | 69 | 1.33 | 695 | 0.005 | 2.7 |
| 129 | D-57 | 69 | 1.33 | 698 | 0.002 | 2.4 |
| 130 | D-91 | 69 | 1.33 | 682 | 0.002 | 2.9 |
| 131 | D-61 | 69 | 1.33 | 697 | 0.002 | 2.1 |
| 132 | D-92 | 69 | 1.33 | 695 | 0.005 | 2.9 |
| 133 | D-64 | 69 | 1.33 | 694 | 0.002 | 1.9 |
| 134 | D-93 | 69 | 1.33 | 662 | 0.003 | 2.1 |
| 135 | D-94 | 69 | 1.33 | 685 | 0.002 | 1.9 |
| 136 | D-95 | 69 | 1.33 | 672 | 0.005 | 4.3 |
| 137 | D-96 | 69 | 1.33 | 691 | 0.003 | 2.9 |
| 138 | D-69 | 69 | 1.33 | 696 | 0.002 | 1.9 |
| 139 | D-97 | 69 | 1.33 | 694 | 0.005 | 1.9 |
| 140 | D-98 | 69 | 1.33 | 681 | 0.005 | 2.8 |
| 141 | D-99 | 69 | 1.33 | 674 | 0.006 | 2.3 |
| C11 | S-1 | 174 | 0.3 | 542 | 0.021 | 10.7 |
| C12 | S-2 | None | None | 547 | 0.022 | 17 |
| C13 | S-3 | 163 | 1.00 | 551 | 0.023 | 10.1 |
| C14 | S-4 | 164 | 1.00 | 551 | 0.024 | 10.2 |

| Sample No. | (2) Desorption rate μg/(cm² · hr) | (3) λmax shift λmax 2/λmax 1 | Jsc (mA/cm²) | (4) Dye residual rate after 200 hours | (5) Adsorption rate μg/(cm² · hr) |
|---|---|---|---|---|---|
| 101 | 10.1 | 0.90 | 18.1 | 73 | 16 |
| 102 | 9.5 | 0.91 | 18.3 | 79 | 22 |
| 103 | 14.2 | 0.90 | 18.0 | 72 | 15 |
| 104 | 1.9 | 0.93 | 19.0 | 88 | 43 |
| 105 | 1.6 | 0.94 | 19.1 | 87 | 45 |
| 106 | 1.2 | 0.93 | 19.0 | 89 | 45 |
| 107 | 1.3 | 0.93 | 19.0 | 88 | 46 |
| 108 | 1.2 | 0.94 | 19.2 | 89 | 44 |
| 109 | 1.1 | 0.93 | 19.6 | 87 | 42 |
| 110 | 0.5 | 0.93 | 19.0 | 89 | 46 |
| 111 | 1.2 | 0.94 | 19.0 | 88 | 44 |
| 112 | 1.2 | 0.94 | 19.0 | 88 | 45 |
| 113 | 1.0 | 0.94 | 19.2 | 89 | 44 |
| 114 | 1.0 | 0.93 | 19.0 | 87 | 44 |
| 115 | 0.4 | 0.96 | 19.7 | 92 | 51 |
| 116 | 0.3 | 0.96 | 19.6 | 91 | 56 |
| 117 | 0.4 | 0.96 | 19.7 | 92 | 50 |
| 118 | 0.5 | 0.96 | 19.6 | 92 | 54 |
| 119 | 0.5 | 0.96 | 19.7 | 91 | 51 |

TABLE 4-continued
| | | | | | |
|---|---|---|---|---|---|
| 120 | 6.9 | 1.0 | 20.6 | 89 | 58 |
| 121 | 7.4 | 1.0 | 20.4 | 87 | 50 |
| 122 | 7.2 | 0.94 | 19.4 | 99 | 51 |
| 123 | 7.6 | 0.95 | 19.2 | 98 | 53 |
| 124 | 7.4 | 0.96 | 19.4 | 95 | 56 |
| 125 | 7.3 | 0.95 | 19.4 | 97 | 51 |
| 126 | 7.5 | 0.95 | 19.2 | 98 | 56 |
| 127 | 7.4 | 0.96 | 19.3 | 97 | 54 |
| 128 | 7.6 | 0.94 | 19.4 | 97 | 51 |
| 129 | 7.5 | 0.95 | 19.2 | 98 | 56 |
| 130 | 7.5 | 0.92 | 19.1 | 98 | 55 |
| 131 | 7.6 | 0.95 | 19.4 | 87 | 210 |
| 132 | 7.6 | 0.94 | 19.4 | 89 | 205 |
| 133 | 7.4 | 0.95 | 19.5 | 89 | 195 |
| 134 | 6.8 | 0.96 | 17.2 | 87 | 187 |
| 135 | 7.5 | 0.95 | 19.5 | 85 | 187 |
| 136 | 8.5 | 0.92 | 18.2 | 88 | 203 |
| 137 | 7.6 | 0.95 | 19.2 | 85 | 195 |
| 138 | 6.9 | 0.94 | 19.5 | 87 | 193 |
| 139 | 7.4 | 0.92 | 18.4 | 86 | 185 |
| 140 | 7.5 | 0.95 | 17.8 | 87 | 192 |
| 141 | 6.8 | 0.96 | 17.2 | 84 | 184 |
| C11 | 20.5 | 0.87 | 17.5 | 68 | 7.8 |
| C12 | 42.9 | 0.82 | 15.2 | 42 | 8.4 |
| C13 | 19.8 | 0.87 | 17.5 | 65 | 7.0 |
| C14 | 18.9 | 0.88 | 17.7 | 67 | 9.5 |
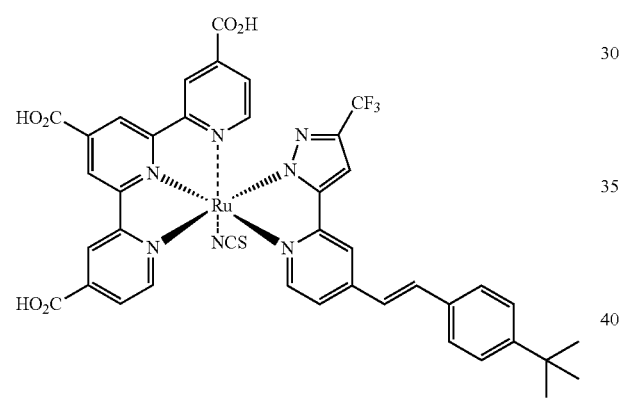
S-1
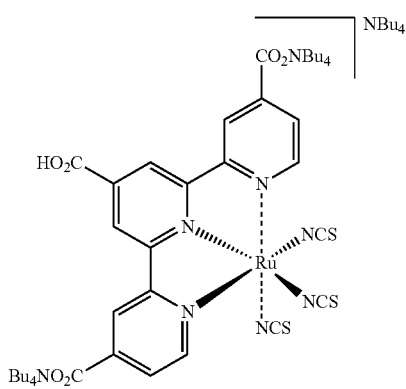
S-2
-continued
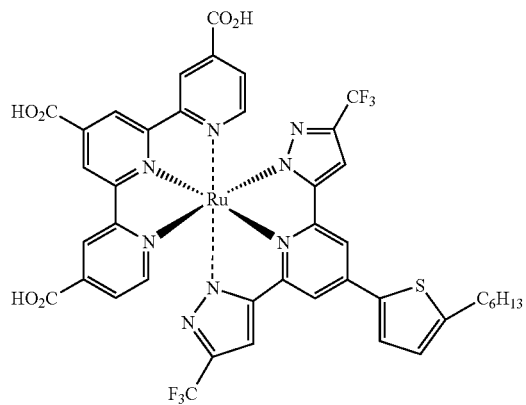
S-3
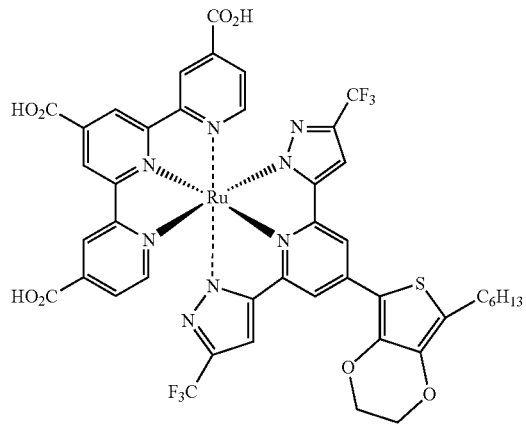
S-4
As is apparent from Table 4, it is understood that the metal complex dye of the present invention exhibits a high open-circuit voltage Voc (mV) and a high retention rate after the heat resistance test [the decreasing rate (%) of open-circuit voltage Voc (mV) after the heat resistance test]. Further, it is understood that the metal complex dye of the present invention exhibits a small standard deviation of the open-circuit voltage Voc (mV) and a less variation.

In terms of desorption rate, each of the metal complex dyes of the present invention is slower than metal complex dyes for comparison, and especially D-15 to D-18, D-33, and D-82, each of which is 0.5 μg/(cm²·hr) or less, are most preferred, and D-7, D-8, D-12, D-13, D-23, D-26, D-30, D-77, D-79, and D-84 within the range of from 1.0 to 2.0 μg/(cm²·hr), which is second-lowest, are preferred.

Further, in terms of adsorption rate, each of the metal complex dyes of the present invention is faster than metal complex dyes for comparison, and especially D-61, D-64, and D-92 to D-99 exhibited particularly good results.

Thus, by reason that the metal complex dye of the present invention has excellent adsorption power (adsorption rate) to the semiconductor fine-particle surface and also hardly desorbs, it appears that this aspect has influence to improvement of durability.

On the other hand, from the results of λmax shift, it is presumed that the metal complex dye of the present invention has a dye structure, which makes a little change of λmax even though an adsorption amount of the dye on semiconductor fine-particles increases, and which hardly causes inefficient association. Thus, it can be presumed that this efficiently makes a progress in electron injection into semiconductor fine-particles, to improve the short-circuit current density Jsc (mA/cm²). D-9 and D-4, in particular among the metal complex dyes of the present invention, caused little lowering in λmax.

The same tests were also carried out with the pastes 1, 3 to 14 in addition to the paste 2, and it was confirmed that good performances were also obtained by each of the metal complex dyes of the present invention, as in the case of the paste 2.

Example 3

According to the procedure described below, a dye-sensitized solar cell having the same configuration as that shown in FIG. 1 of JP-A-2010-218770 was produced. The specific configuration thereof was shown in FIG. 3 of the drawing attached to the present application. In FIG. 3 of the present application, 51 represents a transparent substrate, 52 represents a transparent conductive film, 53 represents a barrier layer, 54 represents an n-type semiconductor electrode, 55 represents a p-type semiconductor layer, 56 represents a p-type semiconductor film, and 57 represents a counter electrode (57a represents a protrusion of the counter electrode).

On a transparent glass plate as the transparent substrate 51 of 20 mm×20 mm×1 mm, SiO₂:F (fluorine-doped Tin oxide) as the transparent conductive film 52 was formed by CVD, to provide a transparent electrically-conductive (transparent conductive oxide: TCO) glass substrate.

Then, 5 ml of a solution in which Ti[OCH(CH$_3$)$_2$]$_4$ was mixed with water in the volume ratio of 4:1, was mixed with 40 ml of a ethyl alcohol solution of which pH was adjusted to 1 with a hydrochloride, to prepare a TiO$_2$ precursor solution. Then, this solution was spin-coated at 1,000 rpm on the TCO glass substrate, and after performing a sol-gel synthesis, it was heated at 78° C. for 45 minutes under vacuum, followed by annealing at 450° C. for 30 minutes, to form a barrier layer 53 composed of a titanium oxide thin film.

Separately, anatase-type titanium oxide particles having an average particle diameter of 18 nm (particle diameter: from 10 nm to 30 nm) were dispersed uniformly in an ethanol/methanol mixed solvent (ethanol:methanol=10:1 (volume ratio)), to prepare a slurry of titanium oxide. At this time, the titanium oxide particles were dispersed uniformly using a homogenizer in the proportion of 10% by mass to 100% by mass of the mixed solvent.

Then, a solution in which ethyl cellulose as a viscosity adjuster was dissolved in ethanol so that its concentration was 10% by mass, and an alcoholic organic solvent (terpineol), were added to the thus-prepared slurry of titanium oxide, and the mixture was dispersed uniformly, again, using a homogenizer. After that, alcohols other than terpineol were removed with an evaporator, followed by mixing with a mixer, to prepare a paste-like titanium oxide-particle-containing composition. The composition of the thus-prepared titanium oxide-particle-containing composition was that the titanium oxide particles was 20% by mass and the viscosity adjustor was 5% by mass, to 100% by mass of the titanium oxide-particle-containing composition.

The thus-prepared titanium oxide-particle-containing composition was coated, on the barrier layer 53 formed as above, by screen printing so that a predetermined pattern was formed, followed by drying at 150° C., and then heating at 450° C. in an electric furnace, to obtain a laminate in which the n-type semiconductor electrode 54 was laminated on the TCO glass substrate. Then, after soaking the laminate overnight in a zinc nitrate (ZnNO$_3$) solution, a surface treatment was conducted by heating at 450° C. for 45 minutes. After that, using any one of various kinds of metal complex dyes shown in Table 5, an ethanol solution of the dye (concentration of the metal complex dye: 1×10$^{-4}$ mol/L) was prepared, and the surface-treated laminate was soaked in the ethanol solution, and left at 25° C. for 24 hours, thereby making the metal complex dye adsorb on the interior of the n-type semiconductor electrode 54.

Then, CuI was added to acetonitrile, to prepare a saturated solution. From the saturated solution, 6 ml of the supernatant liquid was taken out, and 15 mg of 1-methyl-3-ethylimidazolium thiocyanate was added thereto, to prepare a p-type semiconductor solution. Further, on a hot plate having been heated at 80° C., the resultant laminate after the metal complex dye had been incorporated in the n-type semiconductor electrode 54 was disposed. Then, the p-type semiconductor solution was added dropwise with a pipette to coat on the n-type semiconductor electrode 54, to impregnate it therein, followed by drying by allowing it to stand for 1 minute, to prepare a p-type semiconductor layer 55.

Then, a 1 mm-thick copper plate was washed with a 1–M hydrochloric acid, followed by washing with dehydrated ethanol, and heating at 500° C. in the atmosphere for 4 hours, to prepare a copper plate on which CuO nanowires (protrusions 57a) with maximum diameter 100 nm and height 10 μm were grown. This copper plate was encapsulated with iodine crystals in an airtight container, followed by heating in a thermostatic chamber regulated at 60° C. for 1 hour, to prepare a counter electrode 57 on the surface of which a thin CuI layer (p-type semiconductor film 56) was coated. Then, this counter electrode 57 was laminated on the above-prepared laminate, by pressing the counter electrode 57 from the side of the p-type semiconductor layer 55.

The initial open-circuit voltage Voc (mV) of the dye-sensitized solar cells thus prepared was measured in the same manner as in Example 1. The results are shown in Table 5.

TABLE 5

| Sample No. | Metal complex dye | Voc (mV) | Remarks |
|---|---|---|---|
| 211 | D-17 | 651 | This invention |
| 212 | D-15 | 632 | This invention |
| 213 | D-18 | 653 | This invention |
| 214 | D-9 | 654 | This invention |
| 215 | D-40 | 662 | This invention |
| 216 | D-47 | 641 | This invention |
| 217 | D-60 | 632 | This invention |
| 218 | D-61 | 644 | This invention |
| 219 | D-64 | 651 | This invention |
| 220 | D-69 | 642 | This invention |
| C21 | S-1 | 572 | Comparative example |
| C22 | S-2 | 562 | Comparative example |

As is apparent from Table 5, it is confirmed that good performances and improved results are obtained by the metal complex dyes of the present invention.

Example 4

Figure 4:
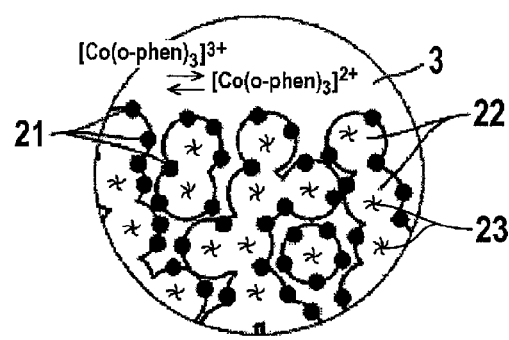
FIG. 4 is a cross-sectional view schematically showing a modification example of the photoelectric conversion element as shown in FIG. 1 in its enlarged portion (circle), with respect to the dye-sensitized solar cell prepared in Example 3 in which a cobalt complex was used in an electrolyte.

According to the following method, the dye-sensitized solar cell shown in FIG. 4 was prepared, by subjecting a photoelectrode to a CdSe quantum dot-making treatment, and employing an electrolyte with a cobalt complex.

An ethanol solution of titanium (IV) bis(acetylacetonato) diisopropoxide was sprayed 16 times onto the surface of FTO glass (1) (manufactured by Nippon Sheet Glass, surface resistance: 8 $\Omega sq^{-1}$), followed by calcining at 45° C. for 30 minutes or more. On this substrate, a transparent layer of about 2.1 μm composed of 20 nm-$TiO_2$ and a light-scattering layer of about 6.2 μm composed of 60 nm-$TiO_2$ (manufactured by Showa Titanium) were laminated by a screen printing, followed by subjecting to a post-treatment with a $TiCl_4$ aqueous solution, to prepare a FTO/$TiO_2$ film 2.

This FTO/$TiO_2$ film 2 was soaked in a 0.03-M $Cd(NO_3)_2$ ethanol solution for 30 seconds in a glove bag under an inert gas atmosphere, followed by successively soaking in a 0.03-M selenide ethanol solution for 30 seconds. After that, the film was washed in ethanol for 1 minute or more, to remove an excessive precursor, followed by drying. These steps of: soaking→washing→drying, were repeated 5 times, to make the CdSe quantum dots (23) grow in the titanium oxide layer (22). Then, the resultant film was subjected to a surface stabilization treatment with CdTe. In this manner, a CdSe-processed photoelectrode was prepared.

The selenide ($Se^{2-}$) was prepared in the system, by adding 0.068 g of $NaBH_4$ (so as to be 0.060 M concentration) to a 0.030 M $SeO_2$ ethanol solution, under Ar or $N_2$ atmosphere.

The CdSe-processed photoelectrode was soaked for 4 hours in the dye solution containing the metal complex dye as shown in Table 6 (ex. 1=0.3 mM Z907 Na acetonitrile/t-butanol (1:1) solution; and ex. 2=0.1 mM SQ1 ethanol solution), to adsorb the metal complex dye as shown in Table 4 onto the photoelectrode. After that, the photoelectrode and the counter electrode (4, a product obtained by chemically depositing Pt from a 2-propanol solution of hexachloroplatinate (0.05 M) on a FTO glass, at 400° C. for 20 minutes) were put together by sandwiching a 25 μm-thick Surlyn (manufactured by DuPont) ring between them, followed by sealing by thermal melting. An electrolyte using a cobalt complex (an acetonitrile/ethylene carbonate (4:6/v:v) solution of 0.75M Co (o-phen)$_3^{2+}$, 0.075M Co (o-phen)$_3^{3+}$, and 0.20M $LiClO_4$) was injected into the interspace 3 between the electrodes through an opening made in advance in the side of the counter electrode. After that, the opening was closed by heat with a BYNEL (manufactured by DuPont) sheet and a thin glass slide, to prepare a dye-sensitized solar cell (cell A).

Similarly, a dye-sensitized solar cell (cell B) was prepared, using the same iodine-based redox solution containing iodine and lithium iodide as in Example 1.

The cobalt complex added to the electrolyte was prepared according to a method described in Chemical Communications, Vol. 46, pages 8788 to 8790 (2010).

Initial performances of the dye-sensitized solar cells thus prepared were tested in the same manner as in Example 1. The results of an initial open-circuit Voc (mV) of these performances are shown in Table 6.

TABLE 6

| Sample No. | Cell | Dye | Voc (mV) | Remarks |
|---|---|---|---|---|
| 311 | A | D-4 | 734 | This invention |
| 312 | A | D-6 | 736 | This invention |
| 313 | A | D-7 | 753 | This invention |
| 314 | A | D-8 | 752 | This invention |
| 315 | A | D-17 | 760 | This invention |
| 316 | A | D-15 | 761 | This invention |
| 317 | A | D-18 | 772 | This invention |
| 318 | A | D-40 | 770 | This invention |
| 319 | A | D-47 | 771 | This invention |
| 320 | A | D-60 | 771 | This invention |
| 321 | A | D-61 | 773 | This invention |
| 322 | A | D-64 | 774 | This invention |
| 323 | A | D-69 | 772 | This invention |
| 324 | B | D-17 | 682 | This invention |
| C21 | A | S-1 | 667 | Comparative example |
| C22 | A | S-2 | 641 | Comparative example |

As is apparent from Table 6, it is confirmed that good performances and improved results are obtained by the metal complex dyes of the present invention.

Example 5

Photoelectric conversion elements were prepared in the same manner as in Example 1, except for utilizing a coexisting co-adsorbent shown in Table 7, and evaluation of performances was carried out in the same manner. The co-adsorbent was added in the proportion of 20 moles, to mole of a total of the metal complex dyes. A rate of increase in photoelectric conversion efficiency was obtained from a photoelectric conversion efficiency ($\eta$) in the case where the co-adsorbent existed and a photoelectric conversion efficiency ($\eta'$) in the case where no co-adsorbent was contained, according to: $[(\eta-\eta')/\eta' \times 100]$.

Effects of improvement due to the co-adsorbent were evaluated according to the following rank.

AA: An increase of 60% or more was observed.

A: An increase of 40% or more and less than 60% was observed.

B: An increase of 0% or more and less than 40% was observed.

C: A lowering in performance was observed.

The results are shown in Table 7.

TABLE 7

| Sample No. | Metal complex dye | Co-adsorbent | Rate of increase in photoelectric conversion efficiency | Remarks |
|---|---|---|---|---|
| 411 | D-17 | Chenodeoxycholic acid | AA | This invention |
|  | D-17 | Cholic acid | AA | This invention |
|  | D-17 | Deoxycholic acid | AA | This invention |
|  | D-17 | Butanoic acid | A | This invention |
|  | D-17 | Decanoic acid | A | This invention |
| 412 | D-15 | Chenodeoxycholic acid | AA | This invention |
|  | D-15 | Cholic acid | AA | This invention |
|  | D-15 | Deoxycholic acid | AA | This invention |
|  | D-15 | Butanoic acid | A | This invention |
|  | D-15 | Decanoic acid | A | This invention |
| 413 | D-1 | Chenodeoxycholic acid | B | This invention |
| 414 | D-2 | Chenodeoxycholic acid | A | This invention |
| 415 | D-3 | Chenodeoxycholic acid | AA | This invention |
| 416 | D-4 | Chenodeoxycholic acid | AA | This invention |
| 417 | D-6 | Chenodeoxycholic acid | AA | This invention |
| 418 | D-7 | Chenodeoxycholic acid | AA | This invention |
| 419 | D-8 | Chenodeoxycholic acid | AA | This invention |
| 420 | D-9 | Chenodeoxycholic acid | AA | This invention |
| 421 | D-12 | Chenodeoxycholic acid | AA | This invention |
| 422 | D-40 | Chenodeoxycholic acid | AA | This invention |
| 423 | D-47 | Chenodeoxycholic acid | AA | This invention |
| 424 | D-60 | Chenodeoxycholic acid | AA | This invention |
| 425 | D-61 | Chenodeoxycholic acid | AA | This invention |
| 426 | D-64 | Chenodeoxycholic acid | AA | This invention |
| 427 | D-69 | Chenodeoxycholic acid | AA | This invention |

As is apparent from the results of Table 7, in the photoelectric conversion element of the present invention, it is recognized a drastic increase in photoelectric conversion efficiency η (%), due to coexistence of a specific co-adsorbents.

Example 6

A solar cell using the cell shown in FIG. 2 of JP-A-2004-146425, a solar cell using the photoelectrode shown in FIG. 1 of JP-A-2004-152613, a solar cell using the tandem cell prepared in the same manner as in Example 1 of JP-A-2000-90989, and a dye-sensitized solar cell shown in FIG. 1 of JP-A-2003-217688, were prepared, and the same tests as above were conducted. As a result, it was confirmed that good performances were obtained by the metal complex dyes of the present invention.

Having described our invention as related to the present embodiments, it is our intention that the invention not be limited by any of the details of the description, unless otherwise specified, but rather be construed broadly within its spirit and scope as set out in the accompanying claims.

REFERENCE SIGNS LIST

1 Electrically-conductive support
2 Photosensitive layer
21 Dye
22 Semiconductor fine-particles
23 CdSe quantum dots
3 Charge transfer layer
4 Counter electrode
5 Light-receiving electrode
6 Circuit
10 Photoelectric conversion element
100 System utilizing a photoelectro-chemical cell
M Electric motor (electric fan)
20 Dye-sensitized solar cell
40 Photoelectrode
41 Transparent electrode
42 Semiconductor electrode
43 Transparent conductive film
44 Substrate
45 Semiconductor layer
46 Light-scattering layer
CE Counter electrode
E Electrolyte
S Spacer
50 Dye-sensitized solar cell
51 Transparent substrate
52 Transparent electrically-conductive film
53 Barrier layer
54 n-type semiconductor electrode
55 p-type semiconductor layer
56 p-type semiconductor film
57 Counter electrode
57a Protrusion
61 Metal complex dye of a octahedral structure having a 5-(2-pyridyl)pyrazole ligand and a terpyridyl ligand
61a Cyclic group
62 Surface of semiconductor fine-particles

The invention claimed is:

1. A photoelectric conversion element, having:
an electrically-conductive support;
a photoconductor layer having a layer of semiconductor fine-particles that have adsorbed a dye;
a charge transfer layer containing an electrolyte; and
a counter electrode;
which are provided on one side of the electrically-conductive support in this order, wherein the dye has at least one terdentate ligand having at least one acidic group; at least one ligand coordinating to a metal atom M has an sp2 carbon atom; a cyclic group binds to the sp2 carbon atom; in a circle position connecting through a carbon atom(s) from an atom of the cyclic group directly binding to the sp2 carbon atom, a substituent R is substituted at an atom of an α-position or β-position to the atom of the cyclic group directly binding to the sp2 carbon atom, with the substituent R being selected from a linear or branched alkyl group, a cycloalkyl group, an alkoxy group, a cycloalkoxy group, an aryloxy group, an alkylthio group, a cycloalkylthio group, an arylthio group, an amino group, an alkylamino group, a cycloalkylamino group, an arylamino group, a heterocyclic amino group, a silyl group, or a silyloxy group; and when the atom of the α-position or β-position to which the substituent R binds is defined as G1 and an atom of the substituent R which directly binds to the atom G1 is defined as G2, an angle θ (∠MG1G2) formed by the metal atom M, the atom G1 and the atom G2, which is centered on the atom G1, is 150° or less, wherein the metal complex dye is represented by formula (I):

M(LD)$_{m1}$(LA)$_{m2}$(X)$_{m3}$.CI     Formula (I)

wherein, in formula (I), M represents Ru or Os; LD represents a bidentate or terdentate ligand represented by formula (A-4) or (A-5); LA represents a terdentate ligand represented by formula (B1); X represents a monodentate ligand; CI represents a counter ion in the case where the counter ion is necessary to neutralize a charge in formula (I); m1 represents 1 or 2; m2 represents 1; and m3 represents 0 or 1;

Formula (A-4)

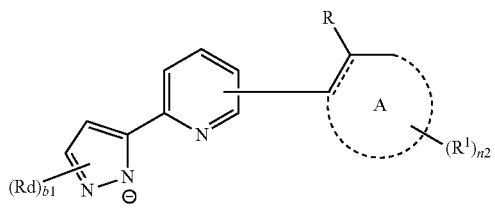

Formula (A-5)

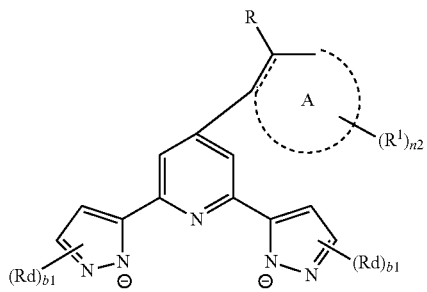

wherein, in Formulae (A-4) and (A-5), the ring A represents a thiophene ring or a benzene ring; when the ring A is a thiophene ring, R and R$^1$ each represent a linear alkyl group in which R and R$^1$ do not bind together to form a ring, n2 is 0 or 1, b1 is 1, and Rd represents a trifluoromethyl group; when the ring A is a benzene ring, R and R$^1$ each represent an alkoxy group in which R and R$^1$ do not bind together to form a ring, n2 is 0 or 1, b1 is 1, and Rd represents a trifluoromethyl group; and in Formula (A-4), ring A bonds to the pyridine ring at the meta or para position but not at the ortho position;

Formula (B1)

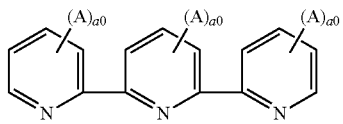

wherein, in formula (B1)
A represents a carboxylic acid; and
a0 is 1.

2. The photoelectric conversion element according to claim 1, wherein a maximum linking chain number N$_R$ of linking chain numbers (bond numbers) of a linking chain linking the atom G1 with an atom located at the furthest position through a linkage of the substituent R is more than ½ times of a minimum linking chain number N$_{M-G1}$ of linking chain numbers (bond numbers) of a linking chain linking from the metal atom M to the atom G1.

3. The photoelectric conversion element according to claim 2, wherein the maximum linking chain number N$_R$ is more than 1 time of the minimum linking chain number N$_{M-G1}$.

4. The photoelectric conversion element according to claim 1, wherein a co-adsorbent having one or more acidic groups is carried on the semiconductor fine-particles.

5. The photoelectric conversion element according to claim 4, wherein the co-adsorbent is represented by formula (CA):

Formula (CA)

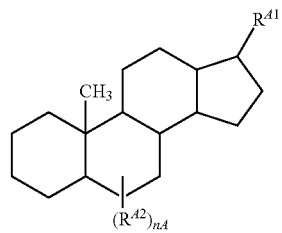

wherein, in formula (CA), R$^{A1}$ represents a substituent having an acidic group; R$^{A2}$ represents a substituent of any of the cyclohexane rings constituting the co-adsorbent represented by formula (CA); and nA represents an integer of 0 or more, and when nA is an integer of 2 or more, a plurality of R$^{A2}$'s may be the same or different from one another.

6. The photoelectric conversion element according to claim 1, wherein a redox-based compound contained in the electrolyte is a cobalt complex.

7. A dye-sensitized solar cell, comprising the photoelectric conversion element according to claim 1.

8. A dye solution for a photoelectric conversion element, having dissolved therein the metal complex dye according to claim 1.

9. The dye solution according to claim 8, wherein, in an organic solvent, the metal complex dye is contained in an amount of from 0.001 to 0.1% by mass, and water is limited to 0.1% by mass or less.

10. The dye solution according to claim 8, further containing a co-adsorbent.

11. The dye solution according to claim 10, wherein the co-adsorbent is represented by formula (CA):

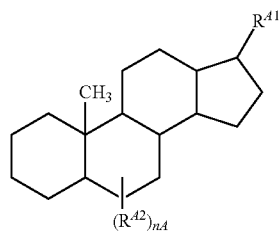
Formula (CA)
wherein, in formula (CA), $R^{A1}$ represents a substituent having an acidic group; $R^{A2}$ represents a substituent of any of the cyclohexane rings constituting the co-adsorbent represented by formula (CA); and nA represents an integer of 0 or more, and when nA is an integer of 2 or more, a plurality of $R^{A2}$'s may be the same or different from one another.
\* \* \* \* \*